United States Patent
Shin et al.

(10) Patent No.: US 9,314,567 B2
(45) Date of Patent: Apr. 19, 2016

(54) ELECTRO-OSMOTIC PUMPS, SYSTEMS, METHODS, AND COMPOSITIONS

(75) Inventors: Woonsup Shin, Kyunggi (KR); Adam Heller, Austin, TX (US); Rajaram Nagarale, Austin, TX (US)

(73) Assignee: BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 675 days.

(21) Appl. No.: 13/583,583

(22) PCT Filed: Mar. 9, 2011

(86) PCT No.: PCT/US2011/027760
§ 371 (c)(1),
(2), (4) Date: Sep. 7, 2012

(87) PCT Pub. No.: WO2011/112723
PCT Pub. Date: Sep. 15, 2011

(65) Prior Publication Data
US 2013/0041353 A1    Feb. 14, 2013

Related U.S. Application Data

(60) Provisional application No. 61/370,139, filed on Aug. 3, 2010, provisional application No. 61/312,233, filed on Mar. 9, 2010.

(51) Int. Cl.
*A61M 5/142*    (2006.01)
*F04B 19/00*    (2006.01)
(Continued)

(52) U.S. Cl.
CPC .......... *A61M 5/14248* (2013.01); *A61K 9/0004* (2013.01); *F04B 19/006* (2013.01); *A61M 2005/14513* (2013.01); *Y10T 29/49236* (2015.01)

(58) Field of Classification Search
CPC ................... H01M 8/04; C07K 1/26
See application file for complete search history.

(56) References Cited

U.S. PATENT DOCUMENTS 4,158,085 A  *  6/1979  Bilhorn .................. 429/130
5,405,614 A  *  4/1995  D'Angelo et al. ............ 424/449
(Continued)

FOREIGN PATENT DOCUMENTS

EP    1811257 A1    7/2007
EP    2065353 A1    6/2009
(Continued)

OTHER PUBLICATIONS

Brask et al. (Lab Chip, 2006, 6, 280-288).*
(Continued)

*Primary Examiner* — Jennifer Dieterle
(74) *Attorney, Agent, or Firm* — Baker & McKenzie LLP

(57) ABSTRACT

The present disclosure relates, according to some embodiments, to compositions, methods, devices, and systems for delivering a composition (e.g., a fluid composition) to a subject. For example, the present disclosure relates to non-gassing, direct current (DC), electro-osmotic pumps in some embodiments. A pump may comprise an anode (e.g., a porous silver/silver oxide anode), a cathode (e.g., a porous silver/silver oxide cathode), and a membrane (e.g., a porous ceramic membrane) positioned at least partially between the anode and the cathode in some embodiments. A pump system may comprise an electro-osmotic pump, a reservoir comprising a pump fluid chamber in fluid communication with the electro-osmotic pump and a delivery fluid chamber in fluid communication with the electro-osmotic pump; a controller assembly in electrical communication with the anode and the cathode; and a cannula and/or a needle in fluid communication with the delivery fluid chamber. A pump fluid may comprise water and/or a delivery fluid may comprise a drug, in some embodiments.

9 Claims, 29 Drawing Sheets

(51) Int. Cl.
*A61K 9/00* (2006.01)
*A61M 5/145* (2006.01)

(56) References Cited

U.S. PATENT DOCUMENTS

| | | | |
|---|---|---|---|
| 5,628,890 | A | 5/1997 | Carter et al. |
| 5,820,551 | A | 10/1998 | Hill et al. |
| 6,143,164 | A | 11/2000 | Heller et al. |
| 6,592,745 | B1 | 7/2003 | Feldman et al. |
| 7,086,839 | B2 | 8/2006 | Kenny et al. |
| 7,231,839 | B2* | 6/2007 | Huber et al. ............... 73/864.11 |
| 7,235,164 | B2 | 6/2007 | Anex et al. |
| 7,559,356 | B2 | 7/2009 | Paul et al. |
| 2004/0101421 | A1 | 5/2004 | Kenny et al. |
| 2004/0229222 | A1* | 11/2004 | Chui et al. .......................... 435/6 |
| 2004/0234378 | A1 | 11/2004 | Lovette et al. |
| 2005/0016853 | A1* | 1/2005 | Paul et al. ...................... 204/600 |
| 2006/0275138 | A1* | 12/2006 | Sheng et al. ..................... 417/48 |
| 2007/0021734 | A1 | 1/2007 | Bhavaraju |
| 2008/0033338 | A1 | 2/2008 | Smith |
| 2008/0076002 | A1* | 3/2008 | Sunako et al. ................... 429/34 |
| 2008/0260542 | A1* | 10/2008 | Nishikawa et al. ............. 417/48 |
| 2009/0041590 | A1 | 2/2009 | Fuetes et al. |
| 2009/0126813 | A1* | 5/2009 | Yanagisawa et al. ......... 137/831 |
| 2009/0260990 | A1 | 10/2009 | Yanagisawa et al. |
| 2011/0052431 | A1 | 3/2011 | Heldal et al. |
| 2012/0312384 | A1* | 12/2012 | Robinson et al. ............... 137/13 |
| 2013/0153425 | A1 | 6/2013 | Puleo et al. |
| 2013/0153797 | A1 | 6/2013 | Puleo et al. |
| 2013/0156615 | A1 | 6/2013 | Puleo et al. |

FOREIGN PATENT DOCUMENTS

| | | |
|---|---|---|
| JP | 2008-74677 A | 4/2008 |
| JP | 2009-501573 A | 1/2009 |
| KR | 10-1305149 B1 | 9/2013 |
| KR | 10-1420360 B1 | 7/2014 |
| KR | 10-1457629 | 11/2014 |
| WO | 2007/011922 A2 | 1/2007 |
| WO | 2011/112723 | 9/2011 |
| WO | 2014/112726 A1 | 7/2014 |

OTHER PUBLICATIONS

Berrouche et al. (IEEE Transactions on Industry Applications, vol. 45, No. 6, Nov./Dec. 2009).*

Torikai et al. (Journal of the Australian Ceramic Society vol. 49[1], 2013, 9-14).*

Extended European Search Report, EP Application No. 14197748.8, dated Jan. 22, 2015, 5 pages.

Shin, W., et al., "Nafion-Coating of the Electrodes Improves the Flow-Stability of the Ag/SiO2/Ag2O Electroosmotic Pump," Analytical Chemistry, Technical Note, (2011), vol. 83, pp. 5023-5025.

Australian Examination Report, Application No. 2011224634, dated Apr. 9, 2014, 5 pages.

P.G. Erlandsson and N. D. Robinson, "Electrolysis-reducing electrodes for electokinetic devices," Electrophoresis, vol. 32, (2011) pp. 784-790.

F. Heuck, P. Van der Ploeg and U. Staufer, "Deposition and structuring of Ag/AgCl electrodes inside a closed polymeric microfluidic system for electroosmotic pumping," Microelectronic Engineering, vol. 88, (2011), pp. 1887-1890.

W. Shin, S. J. Shin, J. M. Lee, R. K. Nagarale and A. Heller, "A miniature, single use, skin-adhered, low-voltage, electroosmotic pumping-based subcutaneous infusion system," Drug Delivery and Translational Research, vol. 1, (2011), pp. 342-347.

R. K. Nagarale, A. Heller and W. Shin, "A Stable Ag/Ceramic-Membrane/$Ag_2O$ Electroosmotic Pump Built with a Mesoporous Phosphosilicate-on-Silica Frit Membrane," Journal of The Electrochemical Society, vol. 159, No. 1, (2012), p. 14-17.

J. F. Evans and T. Kuwana, "Radiofrequency Oxygen Plasma Treatment of Pyrolytic Graphite Electrode Surfaces," Analytical Chemistry, vol. 49, No. 11 (1977), pp. 1632-1635.

L. Y. Yuan, S. S. Shyu and J. Y. Lai, "Plasma surface treatments of carbon fibers. Part 2: Interfacial adhesion with poly(phenylene sulfide)," Composites Science and Technology, vol. 45, (1995), pp. 9-16.

C. U. Pittman Jr, W. Jiang, G. R. HE and S. D. Gardner, "Oxygen Plasma and Isobutylene Plasma Treatments of Carbon Fibers: Determination of Surface Functionality and Effects on Composite Properties," Carbon, vol. 36, Nos. 1-2 ,(1998), pp. 25-37.

E. D. Perakslis, S. D. Gardner and C. U. Pittman Jr., "Surface composition of carbon fibers subjected to oxidation in nitric acid followed by oxygen plasma," Journal of Adhesion Science and Technology, vol. 11, No. 4, (1997), pp. 531-551.

S. Erden, K. K. C. Ho, S. Lamoriniere, A. F. Lee, H. Yildiz and A. Bismarck, "Continuous Atmospheric Plasma Oxidation of Carbon Fibres: Influence on the Fibre Surface and Bulk Properties and Adhesion to Polyamide 12," Plasma Chem. Plasma Process., vol. 30, (2010), pp. 471-487.

K. Okajima, K. Ohta and M. Sudoh, "Capacitance behavior of activated carbon fibers with oxygen-plasma treatment," Electrochimica Acta, vol. 50, (2005), pp. 2227-2231.

W. Shin, E. Zhu, R.K. Nagarale, C.H. Kim, J.M. Lee, S.J. Shin and A. Heller, "Nafion-Coating of the Electrodes Improves the Flow-Stability of the Ag/$SiO_2$/$Ag_2O$ Electroosmotic Pump," Analytical Chemistry, vol. 83, (2011), pp. 5023-5025.

"A Miniature, Nongassing Electroosmotic Pump Operating at 0.5 V," by Woonsup Shin, et al., Journal of the American Chemical Society, Nov. 13, 2010.

Japanese Office Action, JP Application No. 2012-557218, dated Oct. 2, 2014, 10 pages.

Extended European Search Report issued on Oct. 18, 2013, is corresponding EP Application No. 11754015.3, six pages.

* cited by examiner

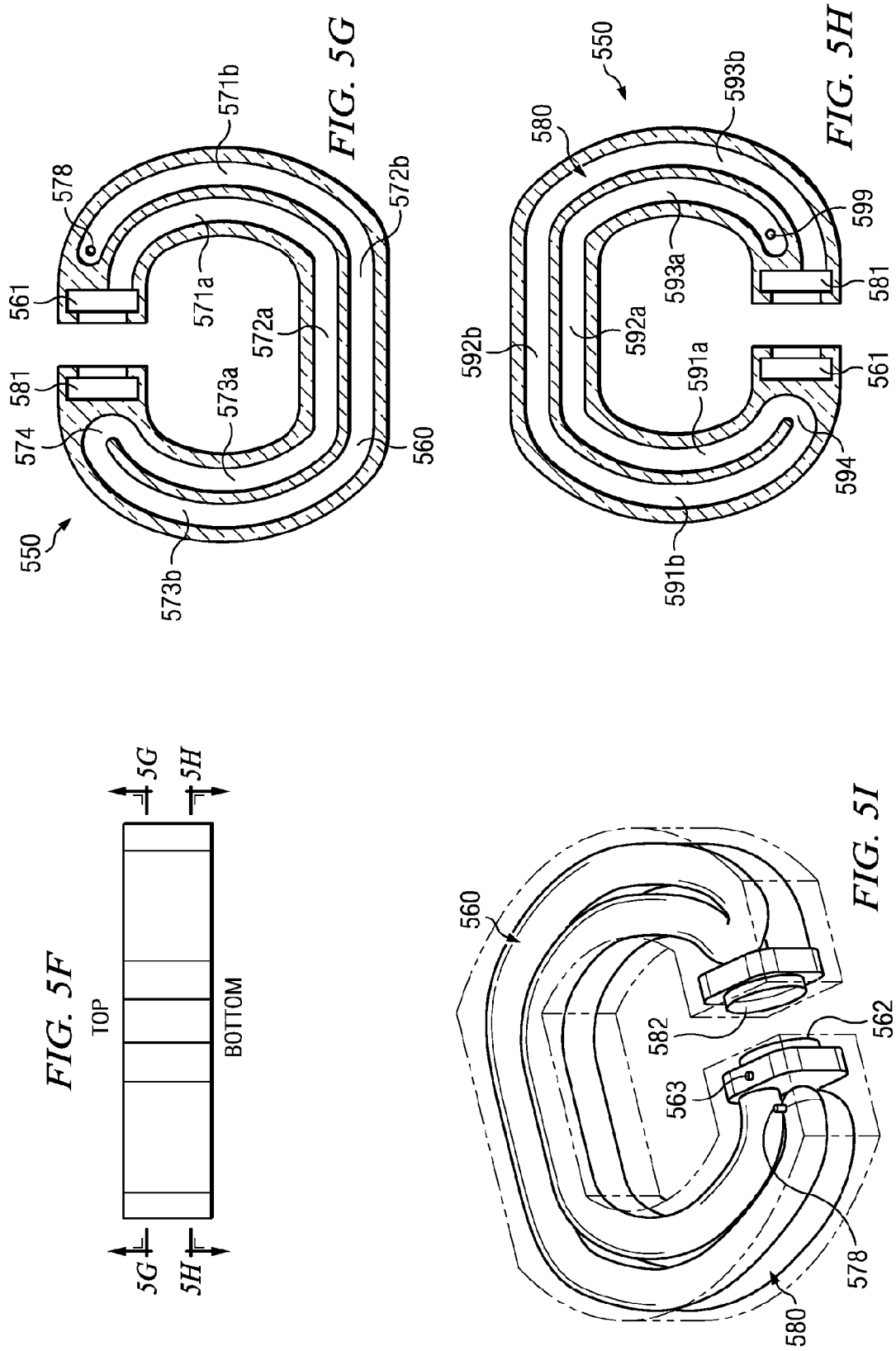

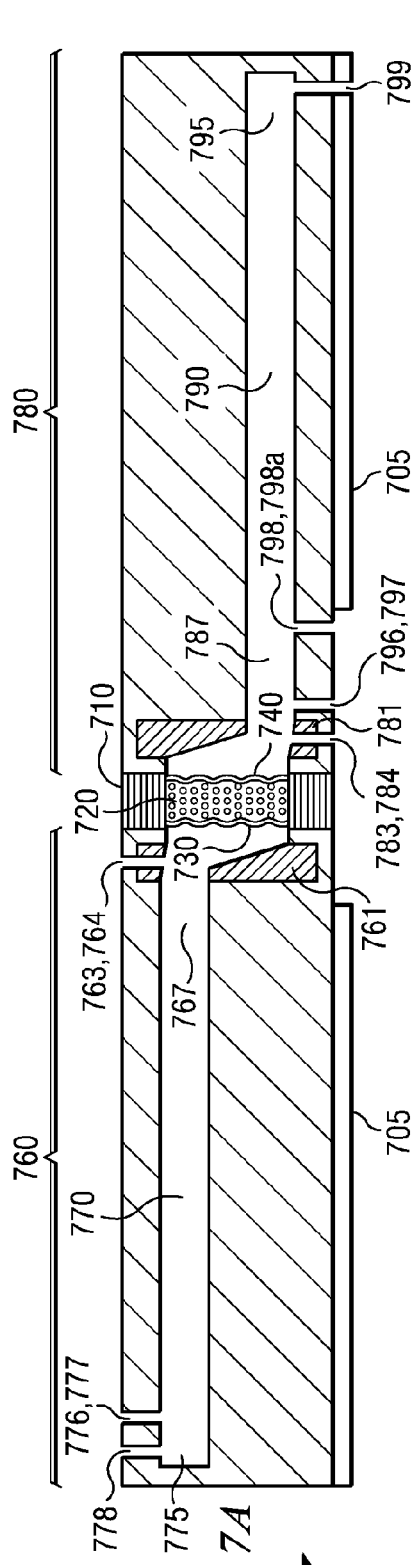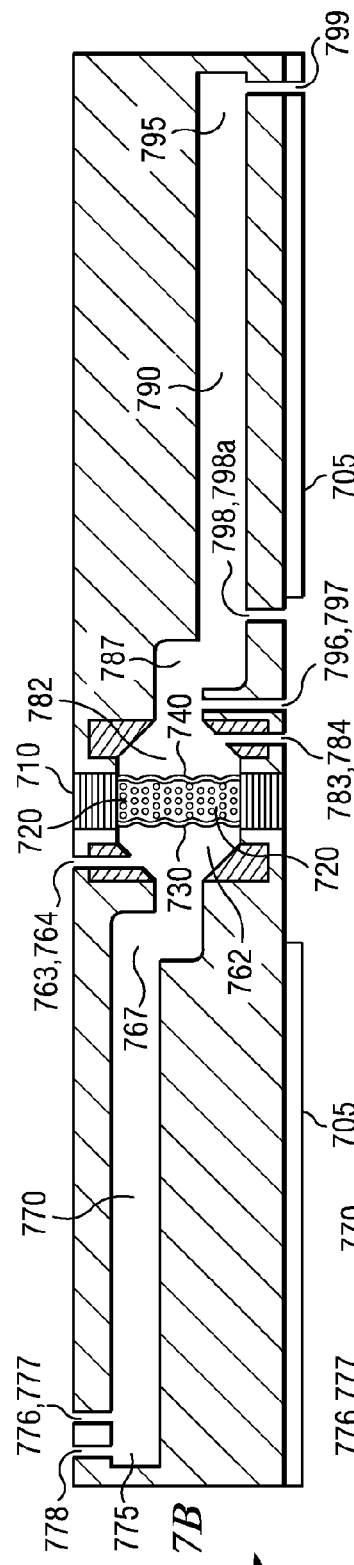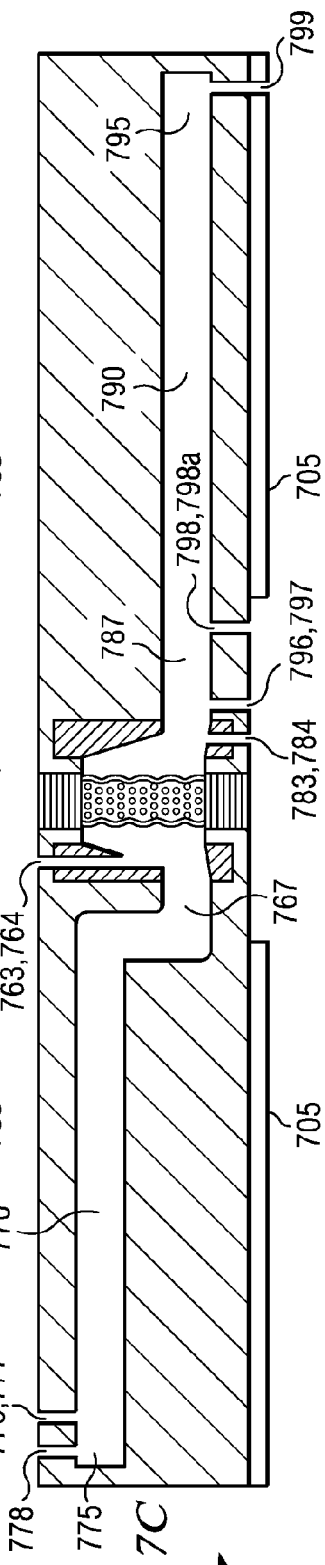

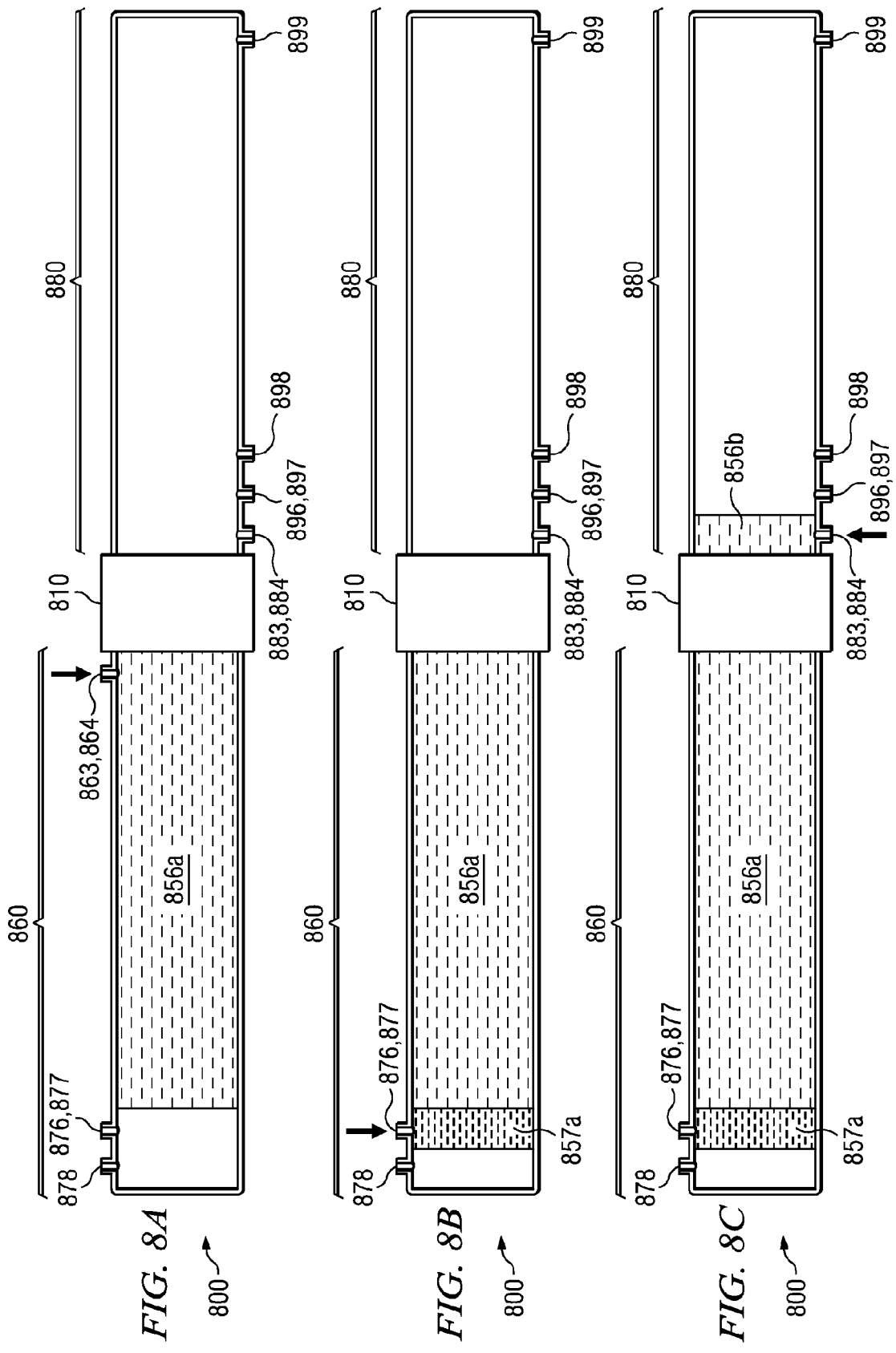

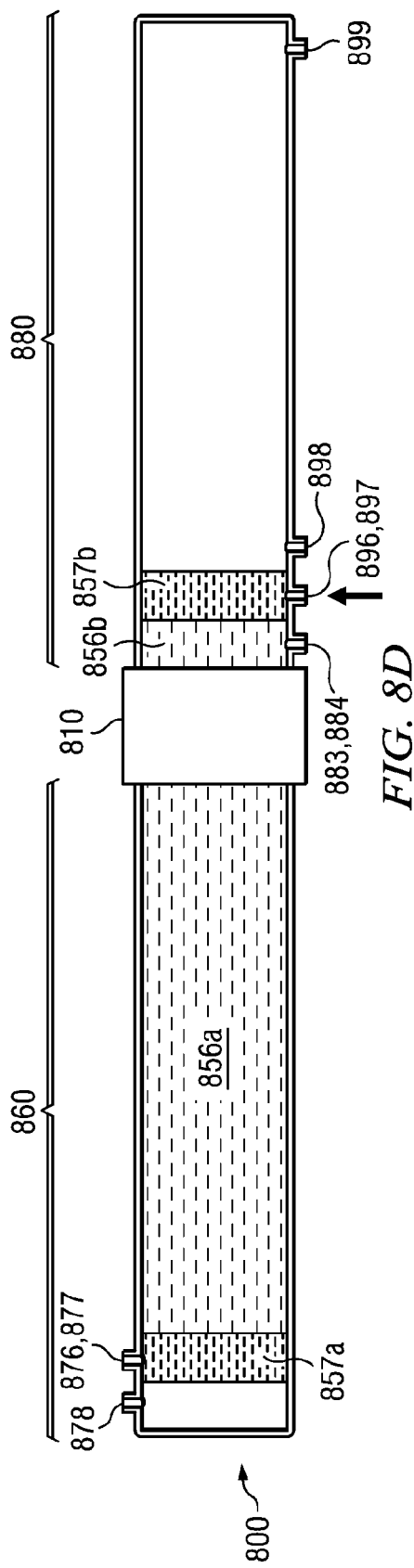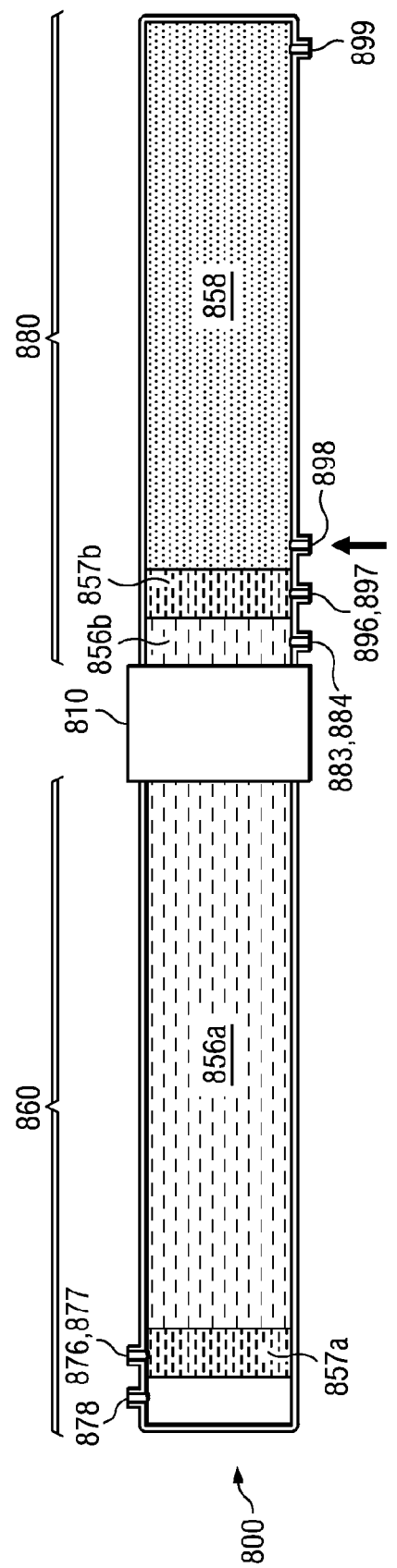

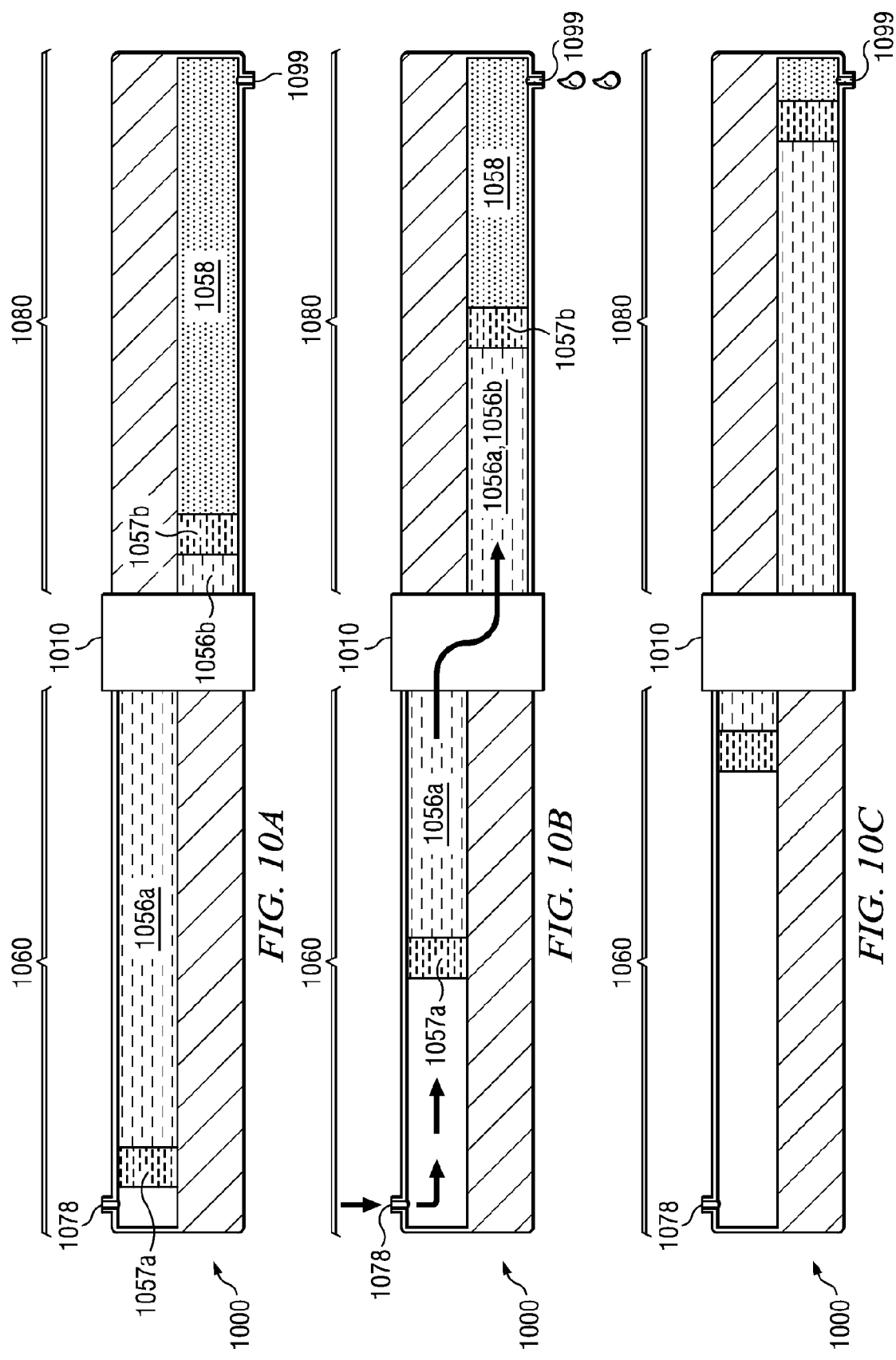

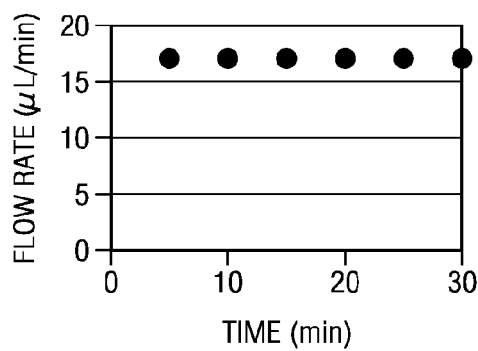
*FIG. 19E*
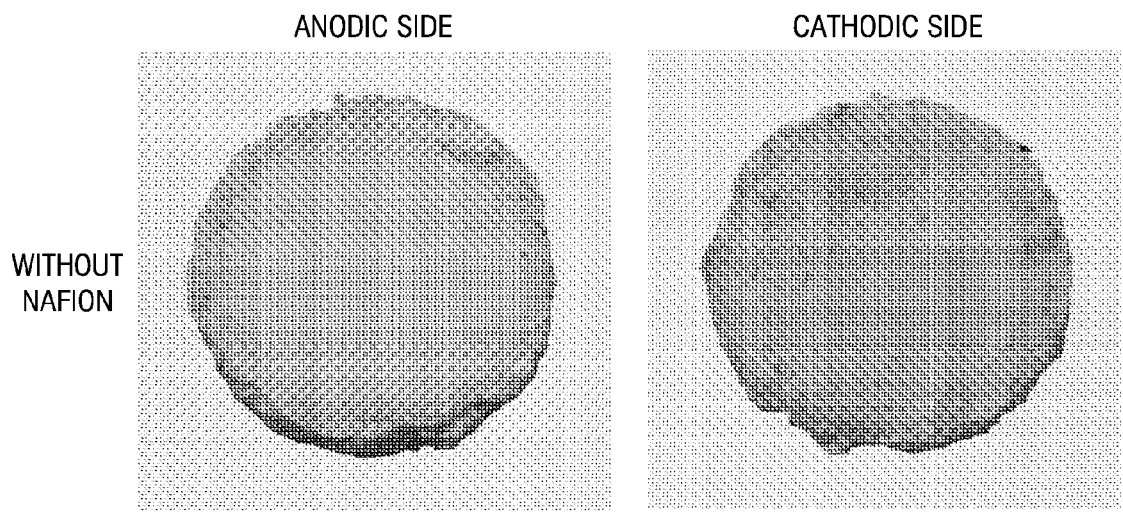
*FIG. 20A*          *FIG. 20B*
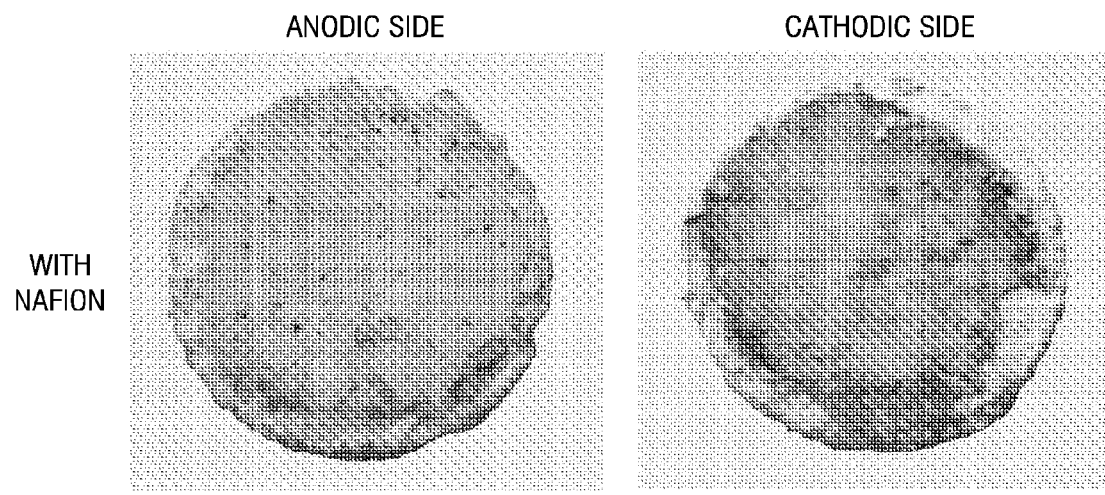
*FIG. 20C*          *FIG. 20D*

ANODIC SIDE 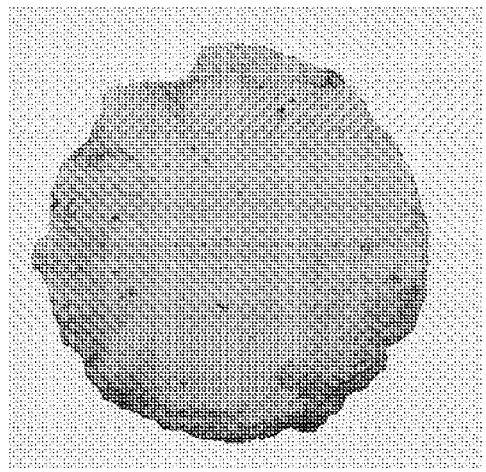 CATHODIC SIDE 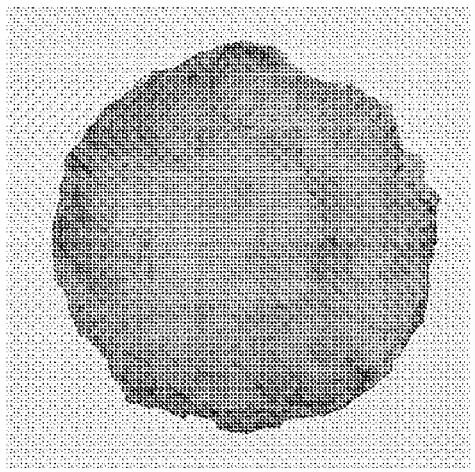
FIG. 22A    FIG. 22B
ANODIC SIDE 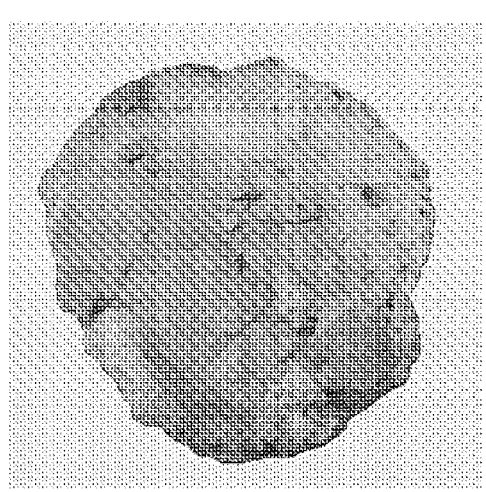 CATHODIC SIDE 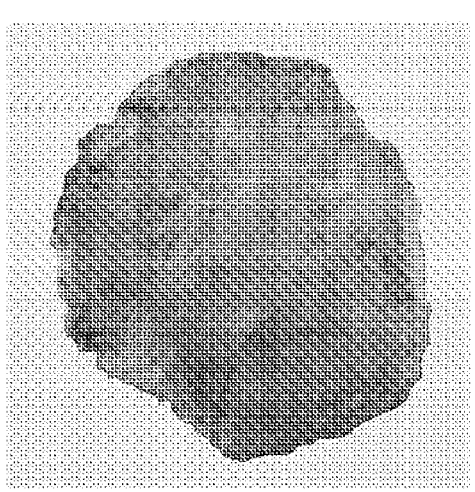
FIG. 22C    FIG. 22D

ELECTRO-OSMOTIC PUMPS, SYSTEMS, METHODS, AND COMPOSITIONS

CROSS-REFERENCE TO RELATED APPLICATIONS

This application is a national phase application under 35. U.S.C. §371 of PCT International Application No. PCT/US2001/027760, filed Mar. 9, 2011. This application claims priority to U.S. Provisional Application No. 61/370,139 filed Aug. 3, 2010. This application also claims priority to U.S. Provisional Application No. 61/312,233 filed Mar. 9, 2010. The contents of all of the above are hereby incorporated in their entirety by reference.

FIELD OF THE DISCLOSURE

The present disclosure relates, in some embodiments, to methods, devices, and systems for drug delivery using pumps, for example, non-gassing, direct current (DC), electro-osmotic pumps.

BACKGROUND OF THE DISCLOSURE

Electro-osmotic pumps for drug release were considered since 1977 when Luft, Kuehl, and Richter (LKR) working at the Siemens Research Laboratory in Erlangen reported an electro-osmotic-pump-based insulin delivering system designed for long-term implantation in diabetic people. To avoid passage of the insulin through the pump, which would have fouled the pump, saline water was pumped. The saline water solution pushed a mobile separator, which, in turn, drove the insulin solution. The LKR pump was elegant in its simplicity, comprising merely an ion-exchange membrane sandwiched between two electrodes. It had no moving parts and its flow rate was current-controlled. Although the LKR pump was considered for use in insulin delivery, it has yet to reach the diabetic people for whom it was intended.

Electro-osmotic pumps have found applications in compact bioanalytical systems and in heat pumps. In some of these, the pumps now drive liquids through long and narrow long on-chip and off-chip capillaries and through miniature packed chromatographic columns Pumps have been integrated in silicon chips and are part of lab-on-chip devices. While polymeric ion exchange membranes were used in the early pumps, the more recent pumps have ceramic membranes, particularly of porous silica, although porous silicon and aluminum oxide have also been used. Platinum electrodes, on which water is electrolyzed at the applied high voltages ranging from 3V to 400V are usually used. Gas bubbles resulting from electrolysis, however, may interfere with the operation of the pumps Electro-osmotic pumps having ceramic membranes and gas-evolving electrodes are now sold, for example, by NFT (Nano Fusion Technologies, Tokyo).

SUMMARY

Accordingly, a need has arisen for inexpensive, reliable pumps for delivery of fluids to a subject. For example, a need has arisen for pumps capable of delivering a fluid (e.g., comprising a drug, allergen, and/or other physiologically relevant compound) to a subject at desired intervals and/or rates (substantially) without fouling.

The present disclosure relates, according to some embodiments, to devices, systems, and methods for delivering a composition to a subject (e.g., human and/or non-human animal). According to some embodiments, an improved electro-osmotic pump system is disclosed that is suitable for use in drug delivery systems. A low-cost, replaceable, small, on-the-skin drug-delivering system is achieved.

In some embodiments, the present disclosure relates, to a pump (e.g., an electro-osmotic pump). For example, a direct current (DC) electro-osmotic pump may comprise (i) a porous cathode comprising $Ag_2O$, (ii) a porous anode comprising Ag, and (iii) a porous ceramic membrane between the cathode and the anode. A pump may further comprise, in some embodiments, (a) an aqueous liquid to be pumped (e.g., in contact with the cathode, anode, and/or membrane), (b) a separator in fluid communication with the aqueous liquid to be pumped and/or (c) a second liquid (e.g., comprising a drug and/or an allergen) in fluid communication with the separator and separated from the aqueous fluid and configured and arranged such that movement of the aqueous liquid (e.g., by the action of the pump) moves the separator, which in turn moves the second liquid. In some embodiments, at least a part of the surface of the membrane may be in physical contact with the anode and/or at least a part of the opposite side of the membrane may be in physical contact with the cathode. A porous ceramic membrane may comprise, according to some embodiments, silica spheres from about 0.1 µm to about 10 µm in diameter (e.g., from about 0.5 µm in diameter to about 3 µm in diameter). In some embodiments, silica spheres may be selected from uncoated silica spheres, phosphosilicic-acid-coated silica spheres, borosilicic acid-coated silica spheres, and combinations thereof. A silica microsphere may optionally be microporous in some embodiments. A silica may comprise, according to some embodiments, metal ions (e.g., metal ions that may lower the glass transition temperature including, without limitation, calcium and/or sodium). For example, a silica may comprise a total concentration of sodium ions and calcium ions of less than about 10 mole percent.

In some embodiments, a porous ceramic membrane may be from about 0.1 mm to about 3 mm thick and/or from about 1 mm to about 30 mm wide. In some embodiments, an electro-osmotic pump may comprise a layered composition. According to some embodiments a layered composition may comprise: (i) a first layer comprising a porous substrate and a coating contacting at least a portion of the substrate; (ii) a second layer comprising a porous silica matrix; (ii) a third layer comprising a porous substrate and a coating contacting at least a portion of the substrate. In some embodiments, the coating may comprise a silver, silver oxide or a combination of silver and silver oxide. In some embodiments, at least a portion of the first layer may be in contact with the second layer and at least a portion of the third layer may be in contact with the second layer. In some embodiments, a porous substrate of a composition layer may comprise carbon (e.g., non-woven carbon paper or cloth). In some embodiments, a layered composition may be free of silver halide and/or free of silver pseudohalide. A layered composition may comprise, in some embodiments, a coating with less than about 2% by weight silver halide, less than about 2% by weight pseudohalide, and/or a total concentration of silver halide and silver pseudohalide of less than 25 by weight. A layered composition may comprise (e.g., have a coating comprising) a polyanionic membrane (e.g., perfluorosulfonic acid/polytetrafluoroethylene copolymer or a perfluorosulfonic acid/polytetrafluoroethylene copolymer).

The potential difference (V) between the anode and the cathode may be 0.1 volts<$V$≤3 volts (e.g., 0.1 volts<$V$≤1.23 volts) at about 25° C. and/or the flow rate per $cm^2$ of liquid-contacted area of the electro-osmotic pump may be at least 10

μL min$^{-1}$ cm$^{-2}$ (e.g., at least 20 μL min$^{-1}$ cm$^{-2}$), according to some embodiments. The potential difference between an anode and a cathode may be, in some embodiments, 1.23 V. The flow rate of an electro-osmotic pump may vary, in some embodiments, about linearly (e.g., linearly) with applied current and/or applied voltage. According to some embodiments, the volume of liquid pumped may be monitored, for example, coulometrically monitored. An anode, a cathode, or both an anode and a cathode may comprise porous carbon (e.g., non-woven carbon, woven carbon paper, or cloth), in some embodiments. An anode may be and/or may comprise a silver mesh according to some embodiments.

The present disclosure also relates, in some embodiments, to methods of producing a pump (e.g., an electro-osmotic pump). For example, a method may comprise adding an aqueous solution of $H_3PO_4$ and/or boric acid to a suspension of silica microspheres (e.g., from about 1 μm to about 3 μm in diameter), evaporating the water from the resulting suspension to form a powder, pressing the power to form a pellet having at least two opposite surfaces, firing the pellet (e.g., for about 4 hours at from about 700° C. to about 900° C.) to form the ceramic membrane, and/or pressing two Ag/Ag$_2$O coated carbon paper electrodes onto opposite surfaces of the ceramic membrane to form an electrode-membrane-electrode sandwich. In some embodiments, a method may further comprise washing and/or drying the ceramic membrane (e.g., after firing the pellet). A suspension of microspheres may comprise one of mono-disperse microspheres and poly-disperse microspheres according to some embodiments. A method may further comprise, in some embodiments, encapsulating the sandwich (e.g., encapsulating the sandwich in epoxy).

The present disclosure also relates, in some embodiments, to methods of pumping a liquid (e.g., an aqueous liquid). For example, a method may comprise contacting the liquid with an electro-osmotic pump comprising a cathode (i) comprising Ag/Ag$_2$O coated carbon paper, (ii) an anode comprising Ag/Ag$_2$O coated carbon paper, and (iii) a ceramic membrane formed by fusing uncoated or phosphosilicic-acid-coated fused ceramic (e.g., silica) spheres (e.g., randomly packed between the cathode and the anode) and/or applying constant current to cause a potential difference between the anode and the cathode of from about 0.1 V to about 3 V such that the aqueous liquid is pumped. According to some embodiments, an aqueous liquid may be water (e.g., deionized water). A liquid (e.g., an aqueous liquid) may comprise water containing a total solute (e.g., electrolyte) concentration of less than about 50 mM, less than about 10 mM, less than about 5 mM, less than about 1 mM, less than about 0.1 mM. A pump may further comprise, in some embodiments, a separator (e.g., a fluid separator comprising air and/or an oil) in fluid communication with an aqueous liquid to be pumped and a second liquid in fluid communication with the separator and separated from the aqueous fluid. A method may further comprise moving the aqueous liquid such that the separator moves, which in turn moves the second liquid. A second liquid may comprise, for example, a drug (e.g., insulin, an antibiotic, and/or a biologic drug) and/or an allergen. In some embodiments, applying current comprises applying a current density from about 0.01 mA cm$^{-2}$ to about 2 mA cm$^{-2}$. The flow rate may vary, in some embodiments, about linearly (e.g., linearly) with applied current and/or applied voltage. For example, the flow rate of an aqueous liquid may vary about linearly (e.g., linearly) with applied current density from about 10 mL min$^{-1}$ A$^{-1}$ cm$^{-2}$ to about 700 mL min$^{-1}$ A$^{-1}$ cm$^{-2}$. At any instant, the flow rate of the aqueous liquid per unit cross sectional aqueous liquid contacted area may be, in some embodiments, between about 10 μL min$^{-1}$ cm$^{-2}$ and about 100 μl min$^{-1}$ cm$^{-2}$. In some embodiments, applying constant current may produce substantially no bubbles (e.g., no bubbles comprising hydrogen and/or oxygen). Application of constant current may comprise applying, according to some embodiments, two or more pulses. For example, in some embodiments the pulses may occur at an interval of less than 10 minutes, 5 minutes, 2 minutes, 1 minute, and/or 30 seconds.

According to some embodiments, a method of pumping a liquid (e.g., aqueous liquid) may comprise contacting the liquid with an electro-osmotic pump comprising a cathode (i) comprising Ag/Ag$_2$O coated carbon paper, (ii) an anode comprising Ag/Ag$_2$O coated carbon paper, and (iii) a ceramic membrane formed by fusing uncoated or phosphosilicic-acid-coated fused ceramic (e.g., silica) spheres (e.g., randomly packed between the cathode and the anode) and/or applying a constant potential difference or voltage between the anode and the cathode of from about 0.1 V to about 3 V such that the aqueous liquid is pumped. According to some embodiments, an aqueous liquid may be water (e.g., deionized water). A liquid (e.g., an aqueous liquid) may comprise a solute at a concentration of less than about 10$^{-2}$ moles per liter in some embodiments. A pump may further comprise, in some embodiments, a separator (e.g., a fluid separator comprising air and/or an oil) in fluid communication with an aqueous liquid to be pumped and a second liquid in fluid communication with the separator and separated from the aqueous fluid. A method may further comprise moving the aqueous liquid such that the separator moves, which in turn moves the second liquid. A second liquid may comprise, for example, a drug (e.g., insulin, an antibiotic, and/or a biologic drug) and/or an allergen. In some embodiments a voltage from about 0.01 V to about 1.2 V, preferably from about 0.02 V and about 1.2 V, is applied. In some embodiments, applying constant potential difference or voltage may produce substantially no bubbles (e.g., no bubbles comprising hydrogen and/or or oxygen). Application of constant current may comprise applying, according to some embodiments, two or more pulses. For example, in some embodiments the pulses may occur at an interval of less than 10 minutes, 5 minutes, 2 minutes, 1 minute, and/or 30 seconds.

The present disclosure also relates, in some embodiments, to a device delivering fluids (e.g., drugs). For example, a device may comprise a reservoir, a controller and one or more sensors. According to some embodiments, an electro-osmotic pump fluid reservoir may comprise two generally tubular fluid chambers from about 2 mm to about 10 mm in inside diameter. According to some embodiments, the interior surface of first, second or both of the fluid chambers may comprise a hydrophobic coating. In some embodiments, the two generally tubular fluid chambers may comprise a first opening and at least one curvature having a concave edge. According to some embodiments, the first opening of the first fluid chamber may face and be spaced apart from the first opening of the second fluid chamber. In some embodiments, an electro-osmotic pump fluid reservoir may comprise at least one curvature having a concave edge of the second fluid chamber that may be coplanar with and proximal to the concave edge of the curvature of the first fluid chamber. In some embodiments, the first fluid chamber may be substantially in a first plane and the second fluid chamber may be substantially in a second plane. In some embodiments, the first plane and second plane may be substantially parallel to each other and the first fluid chamber may be substantially overlaying the second fluid chamber. According to some embodiments, the volume in the first chamber may be smaller, greater or the same as the volume in the second chamber. In some embodiments, a concave edge of the at least one curvature of the first fluid chamber and the concave edge of the at least one curvature of the second fluid chamber of an electro-osmotic pump fluid reservoir may partially define a well configured to receive a controller assembly.

According to some embodiments, a first generally tubular fluid chamber of an electro-osmotic pump fluid reservoir may comprise one or more additional curvatures oriented in substantially the same plane as and concentrically with the first curvature and additional curvatures of the first fluid chamber, and one or more hairpin turns positioned between and in fluid communication with the curvatures of the first fluid chamber. In some embodiments, second generally tubular fluid chamber of an electro-osmotic pump fluid reservoir may comprise one or more additional curvatures oriented in substantially the same plane as and concentrically with the first curvature of the second fluid chamber, and one or more hairpin turns positioned between and in fluid communication with the curvatures of the second fluid chamber. According to some embodiments, an electro-osmotic pump fluid reservoir may comprise two generally tubular fluid chambers with a chamber volume of from about 0.2 mL to about 5 mL. The present disclosure also relates to an electro-osmotic fluid delivery system. In some embodiments, an electro-osmotic fluid delivery system may comprise an electro-osmotic pump, an electro-osmotic pump reservoir, a removable controller assembly and a cannula and/or a needle in fluid communication with a delivery fluid chamber. According to some embodiments an electro-osmotic pump may comprise (i) a porous cathode comprising $Ag_2O$, (ii) a porous anode comprising Ag, and (iii) a porous ceramic membrane between the cathode and the anode. In some embodiments, an electro-osmotic pump reservoir may comprise a pump fluid chamber in fluid communication with the electro-osmotic pump and a delivery fluid chamber in fluid communication with the electro-osmotic pump. In some embodiments, a removable controller assembly may be in electrical communication with the anode and the cathode. In some embodiments an electro-osmotic fluid delivery system may comprise a pump fluid chamber comprising pump fluid proximal to a pump. In some embodiments, the delivery fluid chamber may comprise pump fluid proximal to an electro-osmotic pump, a delivery fluid distal to the electro-osmotic pump and proximal to a needle, and a separator positioned between the pump fluid and the delivery fluid. In some embodiments, an electro-osmotic fluid delivery system may comprise pump fluid consisting essentially of water and a delivery fluid may comprise a pharmaceutically active ingredient, an allergen, an antibody, and/or a nutrient. In some embodiments, an electro-osmotic fluid delivery system may comprise a removable controller assembly comprising a user interface, a processor, memory in electrical signal communication with the processor, and a power source in electrical communication with the processor, and/or the memory. According to some embodiments, an electro-osmotic fluid delivery system controller assembly may comprise a user interface configured to permit the magnitude and/or duration of the current to be applied to a pump, the magnitude and/or duration of the potential difference or voltage to be applied to a pump, or both to be set and/or changed by a user. In some embodiments, a user interface may comprise at least one input key. According to some embodiments, an electro-osmotic fluid delivery system may further comprise a transmitter and/or receiver in signal communication with a controller, a pump, or a controller and a pump. In some embodiments, an electro-osmotic fluid delivery system may comprise an adhesive pad and/or an elastic band fixed to the reservoir. According to some embodiments, an electro-osmotic fluid delivery system may comprise a pump fluid chamber comprising an outer pump fluid chamber curvature comprising a concave edge, an inner pump fluid chamber curvature having a concave edge concentric to and coplanar with the concave edge of the outer pump fluid chamber curvature, and a hairpin turn in fluid communication with the outer and inner pump fluid chamber curvatures. In some embodiments, the delivery fluid chamber may comprise an outer delivery fluid chamber curvature having a concave edge, an inner delivery fluid chamber curvature having a concave edge concentric to and coplanar with the concave edge of the outer delivery fluid chamber curvature, and a hairpin turn in fluid communication with the outer and inner delivery fluid chamber curvatures. According to some embodiments, a pump fluid chamber and a delivery fluid chamber at least partially encircle a removable controller assembly.

The present disclosure also relates to a method of delivering a fluid to a subject. For example, a method may comprise (i) providing an electro-osmotic drug delivery system comprising a reservoir, a removable controller and a needle and/or a cannula in fluid communication with the delivery fluid chamber, (ii) inserting the needle and/or cannula into a subject; and (iii) applying a constant potential difference or constant current between the anode and cathode.

In some embodiments, an electro-osmotic pump may comprise (i) a porous cathode comprising $Ag_2O$, (ii) a porous anode comprising Ag, and (iii) a porous ceramic membrane between and in at physical contact with the cathode and the anode. In some embodiments, an electro-osmotic reservoir may comprise a pump fluid chamber and a delivery fluid chamber in fluid communication with the electro-osmotic pump. In some embodiments, a pump fluid chamber may comprise a first aliquot of pump fluid proximal to the electro-osmotic pump. In some embodiments, a delivery fluid chamber may comprise a second aliquot of pump fluid proximal to a pump, a delivery fluid positioned distal to the electro-osmotic pump, and a separator positioned between the second aliquot of pump fluid and the delivery fluid. In some embodiments, a removable controller may be in electrical communication with an anode and a cathode. In some embodiments, application of a constant potential difference or a constant voltage may comprise moving a volume of a first aliquot of pump fluid from a pump fluid chamber across a porous membrane to a delivery fluid chamber to commensurately increase the volume of the second aliquot of pump fluid in the delivery fluid chamber and through a needle and/or cannula into a subject. In some embodiments, the volume of delivery fluid passing through a needle into a subject may be substantially the same as the increased volume of the second aliquot of pump fluid in the delivery fluid chamber. In some embodiments, a pump fluid may consist essentially of deionized water. In some embodiments, a delivery fluid may comprise insulin, an antibiotic, a biologic drug, and/or allergen. According to some embodiments, the flow rate of a pump fluid may vary linearly with voltage. At any instant the flow rate of a pump fluid per unit cross sectional pump fluid-contacted area may be between about $10\ \mu L\ min^{-1}\ cm^{-2}$ and about $100\ \mu L\ min^{-1}\ cm^{-2}$. Applying constant potential difference or constant voltage may produce substantially no bubbles according to some embodiments.

BRIEF DESCRIPTION OF THE DRAWINGS

Some embodiments of the disclosure may be understood by referring, in part, to the present disclosure and the accompanying drawings, wherein:

FIG. 5F illustrates an elevation view of the reservoir system shown in FIG. 5B according to a specific example embodiment of the disclosure;

FIG. 5G is a sectional view of a reservoir system according to a specific example embodiment of the disclosure along section lines 5G-5G shown in FIG. 5F;

FIG. 5H is a sectional view of a reservoir system according to a specific example embodiment of the disclosure along section lines 5H-5H shown in FIG. 5F;

FIG. 5I illustrates a generally isometric view of the reservoir system shown in FIGS. 5B-5H;

FIG. 7A illustrates a sectional view of a pump system according to a specific example embodiment of the disclosure;

FIG. 7B illustrates a sectional view of a pump system according to a specific example embodiment of the disclosure;

FIG. 7C illustrates a sectional view of a pump system according to a specific example embodiment of the disclosure;

FIG. 8A illustrates a sectional view of a pump system according to a specific example embodiment of the disclosure in which the water chamber is being filled with water;

FIG. 8B illustrates a sectional view of the pump system shown in FIG. 8A in which the water-filled water chamber is being capped with oil according to a specific example embodiment of the disclosure;

FIG. 8C illustrates a sectional view of the pump system shown in FIG. 8B in which the drug chamber is being filled with a water primer according to a specific example embodiment of the disclosure;

FIG. 8D illustrates a sectional view of the pump system shown in FIG. 8C in which the drug chamber is being filled with an oil separator according to a specific example embodiment of the disclosure;

FIG. 8E illustrates a sectional view of the pump system shown in FIG. 8D in which the drug chamber is being filled with a drug-containing fluid according to a specific example embodiment of the disclosure;

FIG. 10A illustrates a sectional view of a pump system in which the water chamber and the drug chambers are loaded and ready for use according to a specific example embodiment of the disclosure;

FIG. 10B illustrates a sectional view of the pump system shown in FIG. 10A during operation according to a specific example embodiment of the disclosure;

FIG. 10C illustrates a sectional view of the pump shown in FIGS. 10A and 10B following operation according to a specific example embodiment of the disclosure;

FIG. 19E illustrates variation of flow rate with time according to a specific example embodiment of the disclosure;

FIG. 20A illustrates the silver precipitation in the ceramic membrane of the pump on the uncoated electrodes of anodic side of membrane, according to a specific example embodiment of the disclosure;

FIG. 20B illustrates the silver precipitation in the ceramic membrane of the pump on the coated NAFION®-electrodes of anodic side of membrane, according to a specific example embodiment of the disclosure;

FIG. 20C illustrates the silver precipitation in the ceramic membrane of the pump on the uncoated electrodes of cathodic side of membrane, according to a specific example embodiment of the disclosure;

FIG. 20D illustrates the silver precipitation in the ceramic membrane of the pump on the coated NAFION®-electrodes of cathodic side of membrane, according to a specific example embodiment of the disclosure;

FIG. 22A illustrates the silver precipitation in the ceramic membrane from the pumps intermittently operated 5 times for 5 minutes at 1.0 V during 38 hours on the electrodes of the anodic side of the membrane, according to a specific example embodiment of the disclosure;

FIG. 22B illustrates the silver precipitation in the ceramic membrane from the pumps intermittently operated 5 times for 5 minutes at 1.0 V during 38 hours on the coated NAFION®-electrodes of anodic side of membrane, according to a specific example embodiment of the disclosure;

FIG. 22C illustrates the silver precipitation in the ceramic membrane from the pumps intermittently operated 5 times for 5 minutes at 1.0 V during 38 hours on the uncoated electrodes of cathodic side of membrane, according to a specific example embodiment of the disclosure;

FIG. 22D illustrates the silver precipitation in the ceramic membrane from the pumps intermittently operated 5 times for 5 minutes at 1.0 V during 38 hours on the coated NAFION-electrodes of cathodic side of membrane, according to a specific example embodiment of the disclosure;

DETAILED DESCRIPTION

Figure 1:
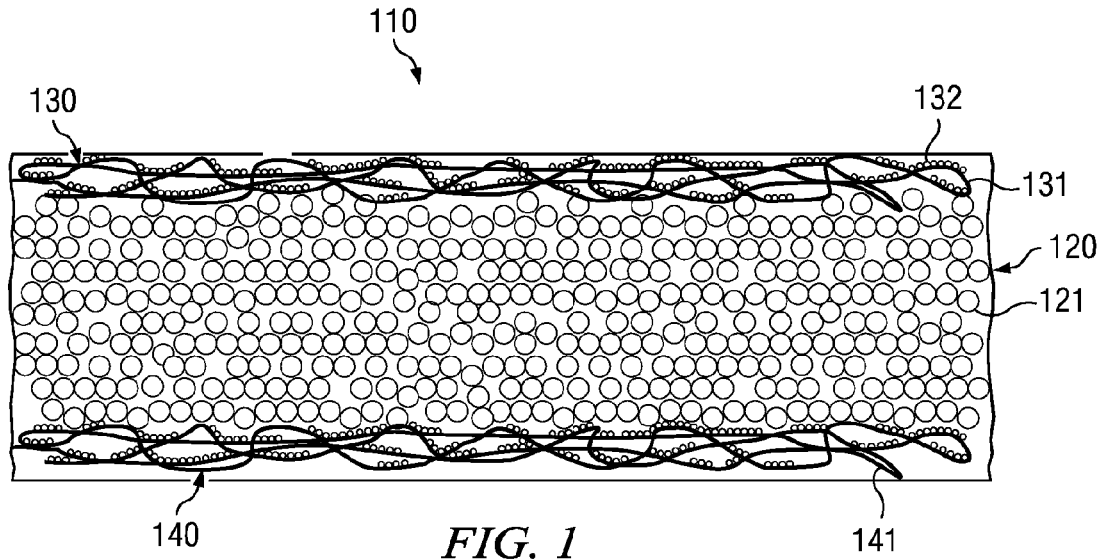
FIG. 1 illustrates a sectional view of the structure of a pump according to a specific example embodiment of the disclosure.

The present disclosure relates, according to some embodiments, to methods, devices, and systems for delivering a composition (e.g., a fluid composition) to a subject (e.g., human and/or non-human animal). For example, delivering a composition (e.g., a fluid composition) to a subject may comprise subcutaneous or other in-tissue delivering (e.g., pumping) of dissolved or solution-dispersed therapeutic drugs. Some pumps of the present disclosure may be of the type that deliver insulin stored in a remote reservoir fluidically connected (e.g., by tubing) to a cannula. Delivery may be accomplished by putting a pump in fluid communication with one or more tissues in a subject. For example, a pump may be in a system that is skin mounted or attached with its cannula connected by a short tubing. In some embodiments, the volume of the unit may be smaller than about 15 $cm^3$, for example, smaller than about 10 $cm^3$, and for example, smaller than about 5 $cm^3$. In some embodiments of the present disclosure, the reservoir may contain a sufficient volume of a fluid (e.g., drug solution or dispersion) for delivery over about a 1-10-day period (e.g., about a 2-3 day period).

Pump Membranes

According to some embodiments a pump may comprise a membrane (e.g., a porous membrane) and two or more electrodes. For example, a pump may be configured as an electro-osmotic pump and comprise a membrane (e.g., a porous membrane), a cathode at least a portion of which is in contact with the membrane, and an anode at least a portion of which is in contact with the membrane. A membrane (e.g., a porous membrane) may have any desired or required shape and/or size. According to some embodiments, a membrane (e.g., a porous membrane) may have a generally circular shape with a circumference and two opposing surfaces. A membrane (e.g., a porous membrane) may have a diameter less than, 8 mm, for example less than 6 mm, for example less than 1.3 mm. A membrane may have a thickness less than 3 mm, for example less than 2 mm, for example, less than 1.3 mm. A membrane (e.g., a porous membrane) may comprise monodisperse or polydisperse silica microparticles with diameters of less than about 10 μm, for example, less than about 10 μm, for example, less than about 5 μm, for example, less than about 2 μm, for example, less than about 1 μm, for example, less than about 0.5 μm, for example, less than about 0.2 μm.

A membrane (e.g., a porous membrane) may comprise, in some embodiments, a porous ceramic or a polymeric organic material having anionic or cationic functions. A membrane may have a polyanionic surface. Examples of useful porous ceramic materials include silica, zirconia, titania, alumina, zirconium phosphate, zirconium silicate, phosphosilicate glass, borosilicate glass. Optionally, a membrane may be formed by heating microspheres of a ceramic, for example, heating fused silica microspheres with phosphoric or polyphosphoric acid. Examples of polymeric-organic membranes include cation exchangers like NAFION® (a perfluorosulfonic acid/polytetrafluoroethylene copolymer), sulfonated polystyrene and its co-polymers.

In some embodiments, a membrane may be formed by pelletizing at 300 psi then firing phosphosilic acid coated 1 μm mono-disperse silica microspheres at 700° C. for 4 h. A membrane may be sandwiched between an anode and a cathode, each of which are coated with 2.6 C equivalents of Ag and $Ag_2O$.

According to some embodiments, a membrane may be made of porous silica that has an optional phoshosilicic acid and/or borosilicic acid shell. Optionally, a silica may be microporous. A microporous silica may have pores with a diameter of, for example, less than about 5 μm or less than about 100 nm. A silica may, in some embodiments, comprise a metal oxide (e.g., $Na_2O$, CaO). For example, a silica may comprise a mole percent of $Na_2O$, CaO, or $Na_2O$+CaO of from about 1 mole percent to about 5 mole percent, from about 5 mole percent to about 10 mole percent, and/or from about 10 mole percent to about 20 mole percent. A membrane may be formed, according to some embodiments, by fusing a phosphosilicic acid coating or a borosilicic acid coating onto fused silica spheres of 1 μm diameter. In some embodiments, a membrane may comprise zirconia ($ZrO_2$) reacted with a phosphorus and oxygen containing compound, such as phosphoric acid or a polyphosphoric acid or phosphorus pentoxide, optionally to form a phosphated zirconia surface, such as a $Zr_3(PO_4)_4$ enriched surface. The zirconia may be stabilized, for example, with yttria, calcium ("calcia"), or other suitable stabilizers. A membrane may comprise, according to some embodiments, alumina ($Al_2O_3$) reacted with a phosphorus and oxygen containing compound, such as phosphoric acid or a polyphosphoric acid or phosphorus pentoxide, optionally to form a phosphated alumina surface. In some embodiments, a membrane may comprise glass, such as soda lime glass or borosilicate glass or lead glass, reacted with a phosphorus and oxygen containing compound, such as phosphoric acid or a polyphosphoric acid or phosphorus pentoxide, optionally to form a phosphated glass surface. In some embodiments, a membrane may comprise a polyvinyl phosphonate polymer or co-polymer membranes, that may be made water-insoluble by crosslinking or according to other known methods.

In some embodiments, a porous membrane may comprise vitreous and/or crystalline ceramics, or mixed vitreous and crystalline oxides comprising, at least in their water or other fluid contacting surface, phosphorus (e.g., in the five-valent oxidation state) and/or boron (e.g., in the five-valent oxidation state). Examples of membrane materials include phosphosilicic acid and/or phosphosilicate glass on fused silica; borosilicic acid on fused silica; zirconia ($ZrO_2$) reacted with a phosphorus and oxygen containing compound, such as phosphoric acid or a polyphosphoric acid or phosphorus pentoxide, optionally to form a phosphated zirconia surface, such as a $Zr_3(PO_4)_4$ enriched surface, with the zirconia optionally phase-stabilized, for example, with yttria or with calcium oxide; or alumina ($Al_2O_3$) reacted with a phosphorus and oxygen containing compound, such as phosphoric acid or a polyphosphoric acid or phosphorus pentoxide, optionally to form a phosphated alumina surface; or a glass such as soda lime glass, or a borosilicate glass or a lead glass, reacted with a phosphorus and oxygen containing compound, such as phosphoric acid or a polyphosphoric acid or phosphorus pentoxide, optionally to form a phosphated glass surface. A phosphosilicate glass and/or a borosilicate glass may be used, the surface of which may be optionally phosphorous-oxide enriched and/or boron oxide enriched. Porous metal phosphates such as $AlPO_4$, $Zr_3(PO_4)_4$, $Zn_3(PO_4)_4$ or $FePO_4$ or $Fe_3(PO_4)_2$ may be used in some embodiments. Packing of fused spheres, according to some embodiments, may be random, haphazard, and/or incompletely ordered.

According to some embodiments, a microsphere may have a diameter (e.g., an average diameter) of less than about 10 μm (e.g., less than about 10 μm, less than about 5 μm, less than about 2 μm, less than about 1 μm, less than about 0.5 μm, less than about 0.2 μm, and/or less than about 0.1 μm).

In accordance with exemplary embodiments and to remove any unbound phosphoric acid resulting from the above process, the about 0.8 cm outer diameter ceramic membranes may be washed with copious amounts of water. After assembly of the membranes in the sandwiches shown in FIG. 5, they may be washed again for about 25 min at about 10 μL $min^{-1}$ flow rate. The washing-water may come from a commercially-available syringe pump or other suitable apparatus.

Pump Electrodes

A potential difference (i.e., a voltage) and/or a current may be applied across the membrane through electrically conductive materials (e.g., electrodes) positioned on opposite sides. The composition of electrically conductive materials may be selected such that the application of a potential difference results in a reaction by which one or more ions (e.g., Ag+, H+, OH⁻ or the like) move across and/or through a membrane according to some embodiments. For example, it may be desirable to select a composition such that protons (H+) move across and/or through a membrane. Electrodes, (e.g., the anode and cathode), according to some embodiments, may be porous. In some embodiments an anode may comprise carbon, for example, woven or non-woven carbon cloth or paper, or carbon foam. One example of a carbon cloth electrode is TGP-H-030, made by Toray Industries Inc., 2-1, Nihonbashi-Muromachi 2 Chome, Chuo-ku, Tokyo, Japan. A porous carbon anode may be coated (e.g., advantageously coated) with, for example, tin oxide, sold, for example, as a NYACOL® SN15 dispersion by Nyacol Nano Technologies Inc., Ashland, Mass. For example, an anode may be, for example, dip-coated, and/or spray-coated with a NYACOL® SN15 dispersion.

In some embodiments, a porous cathode may be carbon-based. For example, a cathode may be woven or non-woven carbon cloth or paper, or carbon foam. A carbon-based, porous cathode, according to some embodiments, may be made hydrophilic. For example, it may be desirable or necessary to make a carbon-based, porous cathode (e.g., a woven or non-woven carbon cloth or paper or a carbon foam) hydrophilic by exposure to a plasma (e.g., an about 20 torr oxygen plasma for about an hour).

According to some embodiments, it may be desirable, preferred, and/or required to use electrodes comprising silver and/or silver oxide. An electrode (e.g., an anode) may comprise enough silver to have a coulombic capacity of at least 10 coulombs, at least 10 coulombs, at least 5 coulombs, at least 3 coulombs, at least 2 coulombs, at least 1 coulomb, and/or at least 0.5 coulombs. An electrode (e.g., a cathode) may comprise enough silver to have a coulombic capacity of at least 10 coulombs, at least 10 coulombs, at least 5 coulombs, at least 3 coulombs, at least 2 coulombs, at least 1 coulomb, and/or at least 0.5 coulombs.

Flow rate at constant applied current may decline, according to some embodiments. For example, flow rate at constant current may decline in the presence of ions at a concentration in excess of $10^{-5}$ M in the water. In a pump comprising a $Ag/Ag_2O$ electrode, a ceramic membrane, and a $Ag/Ag_2O$ electrode, $Ag^+$ ions released from the electrodes may lower current efficiency (i.e., flow rate at a particular constant current). Release of $Ag^+$ ions may be retarded and current efficiency may be better sustained by NAFION®-coating the electrodes. Without being limited to any particular mechanism of action, a NAFION® coating may retain $Ag^+$ ions.

In some embodiments, an electrode may comprise an electrocatalyst (e.g., polyaniline and/or a substituted polyaniline, with or without a second catalyst, such as a platinum group metal, like platinum). Polyanilines may be electrodeposited and/or electropolymerized on the anode from their respective acidic aniline or aniline-derivative solutions and the platinum group metals are electrodeposited and/or chemically deposited on the polyaniline films.

In some embodiments, a cathode may made hydrophilic and then coated with a hydrogen evolution catalyst, such as nickel, palladium, or platinum. One or more electrocatalysts may be electrodeposited on a cathode (e.g., a porous carbon cathode). In some embodiments, polyaniline-coated and platinized carbon cloth electrodes may be used. In some embodiments, a silver-silver halide, for example silver-silver chloride (Ag/AgCl) cathode may be used. Because in Ag/AgCl cathodes, AgCl is reduced to Ag and chloride anions, no hydrogen is evolved. Such cathodes may be made, for example, by cold or hot pressing silver particles to form, preferably, discs of less than 1 cm Outer Diamer (OD), then forming a reactive AgCl surface layer, for example by soaking in a ferric chloride containing acidic solution or electrooxidizing in chloride containing solution, for example, 0.1 M HCl solution. In some embodiments, a cathode may be made by cutting fine silver mesh into a desired shape, for example, into discs, then reacting the mesh with acidic ferric chloride by soaking it in its solution or electrooxidizing in chloride containing solution, for example, 0.1 M HCl solution. Multiple layers of silver chloride coated mesh may be pressed together and used as a cathode. In some embodiments, electrodes comprising platinum may catalyze the evolution of hydrogen and/or oxygen (e.g., in the form of undesirable gas bubbles). Electroosmotic pumping efficiency may be reduced (e.g., undesirably reduced) in pumps comprising silver chloride. Without being limited to any particular mechanism of action, silver chloride may only be stable in chloride-containing aqueous solutions and added chlorides may reduce (e.g., undesirably reduce) the efficiency of electroosmotic pumping.

The desired porosity of an electrode may be achieved, for example, by using a porous substrate (e.g., a porous, conductive, and optionally non-corroding substrate), that need not be electrochemically reactive. Some useful electrode materials, according to some embodiments, include forms of porous carbon, gold and silver, for example woven or non-woven carbon cloth or carbon paper or gold mesh or silver mesh. An electrochemically reactive component of a porous anode or cathode may be applied by any available method. While some impact on flow may be tolerable, it may be desirable to choose/adjust the method as needed to ensure that pores are not occluded to the point of blocking flow. For example, silver can be electrodeposited on the fibers of the carbon paper of the anode; the same material, in which part of the silver is chemically or electrochemically oxidized to silver oxide, can serve as the cathode. Anodes may generate, in some embodiments, protons/and or silver cations in their operation. According to some embodiments, cathodes may generate in their reaction hydroxide anions and/or may consume protons and/or silver cations in their operations.

In some embodiments, an electrode may comprise a silver compound (e.g., silver oxide), but not a silver halide (e.g., silver chloride or silver bromide) or a silver pseudohalide (e.g., silver thiocyanate). For example, an electrode may comprise at least about 30, at least about 20, at least about 10, and/or at least about 5 weight % of a silver oxide in its reactive matter. An electrode may comprise less than about 10%, less than about 5%, less than about 2%, less than about 1%, and/or less than about 0.1% by weight halide+pseudohalide in some embodiments. An electrode may be free (e.g., electrochemically free) of halide, free (e.g., electrochemically free) of pseudohalide, or free (e.g., electrochemically free) of both halide and pseudohalide in some embodiments.

In some embodiments, an electrode may comprise a silver compound (e.g., silver oxide), but not platinum. For example, an electrode may comprise less than about 10%, less than about 5%, less than about 2%, less than about 1%, and/or less than about 0.1% by weight platinum in some embodiments. An electrode may be free (e.g., electrochemically free) of platinum in some embodiments.

An electrode may have any desired or required shape and/or size. According to some embodiments, an electrode (e.g., a porous electrode) may have a generally circular shape with a circumference and two opposing surfaces. In some embodiments, an electrode (e.g., a porous electrode) may have a similar or the same size and shape as its adjacent membrane. An electrode (e.g., a porous electrode) may have a diameter less than about 8 mm, less than about 6 mm, and/or less than about 1.3 mm. An electrode (e.g., a porous electrode) may have a diameter about 5 cm or less, about 2 cm or less, about 1 cm or less, and/or about 6 mm or less. An electrode (e.g., a porous electrode) may have a thickness less than about 3 mm, for example less than about 2 mm, for example, less than about 1.3 mm. In some embodiments, the outer diameter of an electrode-membrane-electrode sandwich may be less than about 5 cm and more than about 0.1 cm; for example, less than about 3 cm and more than about 0.3 cm; for example, less than 1 cm and more than 0.4 cm.

In some embodiments, electrodes may be formed of materials that satisfy the following conditions: (1) non-gassing electrode reactions (e.g., no hydrogen evolved at cathode and no oxygen evolved at anode); and/or (2) anode reaction generates protons and/or silver cations and cathode reaction consumes protons and/or silver cations. An electrode may be formed, according to some embodiments, of materials that satisfy the following conditions (a) non-gassing electrode reactions (e.g., no hydrogen evolved at cathode and no oxygen evolved at anode); and/or (b) anode reaction generates protons and/or copper cations and cathode reaction consumes protons and/or copper cations. Accordingly, the electrodes may be formed in certain embodiments, for example, by $MnOOH/MnO_2$; $Cu/CuO_x$; $Pb/PbO_2$, in addition to $Ag/Ag_2O$.

According to some embodiments, DC electroosmotic pumps with anodes that do not evolve gaseous oxygen and/or cathodes that do not evolve gaseous hydrogen may be desired and/or preferred. Anodes (e.g., preferred anodes) may generate, in some embodiments, protons and/or silver cations in their operation. In some embodiments, anodes may generate protons and/or silver cations in their operation. According to some embodiments, cathodes may generate in their reaction hydroxide anions and/or may consume protons and/or silver cations in their operations. In some embodiments, anodes may comprise silver (Ag); MnOOH; Cu; and/or Pb. In some embodiments, cathodes may comprise $Ag_2O$; CuO and/or $Cu_2O$; an oxide of manganese (Mn) of a valence greater than 3 such as $MnO_2$ and/or an oxide of lead (Pb) of a valence greater than 2 such as $PbO_2$. In some embodiments, anode and cathode materials may match (e.g., complement), such that they comprise the same metal atom, for example to match an Ag-containing anode with an $Ag_2O$-containing cathode, or an MnOOH containing anode with an $MnO_2$ containing cathode, the anode and the cathode may also comprise different metal atoms. For example, an anode may comprise copper (Cu) and the cathode may comprise silver oxide ($Ag_2O$) or the anode may comprise silver (Ag) and the cathode may comprise an oxide of copper. Optionally, anode and cathode materials may comprise both the anodic and the cathodic reactants, for example both Ag and $Ag_2O$, or both Cu and an oxide of copper. Accordingly, in some embodiments, the electrodes may be formed for example, by $MnOOH/MnO_2$; $Cu/CuO_x$; $Pb/PbO_2$, and/or $Ag/Ag_2O$.

Pumps

In some embodiments components of a pump may be simple and inexpensive.

In some embodiments, total cost of pump components may be less than $2.00, for example $1.00 (in 2011 USD). Components of a pump may comprise, a pair of PVC receptacles, a pair of contact strips (e.g., gold, silver), a pair of coated carbon paper electrodes, a ceramic membrane, and silicon tubing. The components of a pump may be assembled by sandwiching a membrane between electrodes. In some embodiments, the diameter of the membrane and electrodes is 8 mm. In some embodiments, the covered rim is less than about 0.3 cm and more than about 0.03 cm, for example, greater than about 0.05 cm and less than about 0.2 cm; the water exposed area may be about 25 $cm^2$ or less, for example, about 10 $cm^2$ or less, for example, about 4 $cm^2$ or less, for example, about 1 $cm^2$ or less, for example, 0.5 $cm^2$ or less, for example, about 0.3 $cm^2$ or less, for example, about 0.1 $cm^2$ or less, for example, about 0.05 $cm^2$ or less. After assembly of the membranes in the sandwiches (e.g., shown in FIG. 1), they may be washed again for about 25 min at about 10 µL $min^{-1}$ flow rate. The washing-water may come from a commercially-available syringe pump or other suitable apparatus.

In some embodiments an electrode may be in close physical contact with the membrane, meaning that there is little or no aqueous liquid (e.g., free-flowing aqueous liquid) separating either electrode from the membrane. In some embodiments, means for good physical contact may include an electrochemically non-reactive thin film (e.g., a thin film of an electron and/or hole conductor) deposited on both sides of the membrane. A non-reactive conductive film may comprise, for example, carbon, gold, and/or platinum. The film may be preferably thin enough to be porous in some embodiments. The film may be deposited, for example, by sputtering or evaporation or it could be painted or sprayed. Available carbon pastes such as SPI carbon #5065 may be used. An electrochemically reactive component containing carbon paper, for example, $Ag/Ag_2O$ containing paper may then be pressed onto the carbon or platinum film on either or both sides of the membrane. In some embodiments, physical contact may be improved by polishing flat a ceramic membrane before pressing onto it the electrochemically reactive component containing carbon paper electrodes. In some embodiments, carbon paper may be hot-pressed onto the two sides of a ceramic membrane at a temperature typically exceeding about 500° C., for example, exceeding about 600° C., for example, exceeding about 700° C., for example, exceeding about 800° C., for example, exceeding about 900° C., for example, exceeding about 1000° C., at a pressure typically exceeding about 0.1 MPa, for example, exceeding about 0.2 MPa, for example, exceeding about 0.5 MPa, for example, exceeding about 1.0 MPa, for example, exceeding about 2 MPa.

In some embodiments, silver or a silver compound (e.g., like silver phosphate or silver borate or silver silicate) may be deposited on one or both sides of the ceramic membrane. The deposition could be, for example, by precipitation silver ions diffusing from the anode and permeating the membrane. In some embodiments, deposition may be by treating the membrane with a metal ion comprising compound, such as a ammoniacal silver, and precipitating on one or both sides of the membrane the metal and/or its compound, for example, by chemical reduction, such as reduction of the ammoniacal silver with a sugar like glucose. In some embodiments, a ceramic membrane may be sequentially dipped in an ammonical silver solution, then in a glucose solution and the process could be optionally repeated, for example, until the desired contacting film is formed. Similarly the membrane could be dipped in a solution containing a gold complex like $AuCl_4^-$ or $Au(CN)_2^-$ or a chloroplatinate salt, of which gold or platinum could be precipitated by a reductant such as a reductant used in electroless plating of gold and/or platinum. In some embodiments, examples of reductants include borohydrides and hypophosphites.

In some embodiments, a ceramic membrane may be coated by an electrode-forming paste on its two sides. In some embodiments, a ground mixture of 300 mg $Ag_2O$ of about 10-20 µm particle size, 300 mg Ag of about of about 1-3 µm particle size, 200 mg $NH_4HCO_3$ may be mixed with 200 mg SPI #5065 carbon paste; this mixture may then be mixed with 600 µL isopropanol; the resulting mixture may then be mixed with 100 μL of 15.5 weight % Nyacol tin oxide colloidal solution containing 1 weight % Triton X100. 20 μL of the resulting mixture may be spin coated at about 10000 rpm on each side of the 8 mm diameter phosphosilicate coated silica sphere membrane, dried then pyrolyzed at about 275° C. for about 2 h. In some embodiments, the electrode may be made porous by the thermal decomposition of $NH_4HCO_3$ whereby gas is formed According to some embodiments, a compartment containing a pump fluid (e.g., pumped water or aqueous solution), and also a compartment containing a delivery fluid (e.g., a drug solution or suspension) may be made, for example, by molding a plastic. Either or both compartments may have a port or septum, such as a septum made of an elastomer, to allow their filling with water or aqueous solution or with a drug solution or suspension. Filling could be done, for example, with a syringe. Either or both compartments may have a hydrophobic vent allowing air or other gases to escape, for example during filling. A vent may optionally comprise a hydrophobic porous material, to allow the escape of gases without allowing leakage of the water or aqueous solution or of the drug suspension or solution. Examples of hydrophobic porous vent materials include but are not limited to hydrophobic gas diffusion membranes optionally made of woven and non-woven fibrous perfluorinated polymers, exemplified by materials used in zinc air batteries, such as the Excellerator™ PTFE Gas Diffusion Membrane of W. L. Gore & Associates of Newark, Del.

Optionally, a drug-containing compartment may contain a drug concentrate in a non-aqueous solution or dispersion, or a solid comprising the drug (e.g., for longer shelf life). In this case the drug solution or suspension is prepared prior to use, for example by adding water or an aqueous solution to the drug containing compartment prior to use. This may be preferred, for example, when the delivered drug is glucagon, available from Eli Lilly & Co. Indianapolis, Ind., because the shelf life of its typically injected solution is usually only of about a day.

In the operation of some electrodes, such as MnOOH/$MnO_2$, in de-ionized water could result in static charge accumulation. This static charge may cause the flow of a transient current in the external circuit in the direction opposite to that in normal operation of a pump and may transiently reverse the flow. Such undesired reversal of the flow may be prevented mechanically, by preventing reverse flow of the pumped water, for example by inserting a check-valve, using for example a PP miniature check valve, ⅛" (EW-98553-10) available from Cole-Parmer. Alternatively it may be prevented electronically, by preventing the reverse flow of the current, for example by incorporating in the external circuit a Schottky diode, such as diode 1N5711 from STMicroelectronics.

In some embodiments, a $Ag/Ag_2O$ anode and a cathode may be reversible and identical except for their local pH difference. Little, if any, oxygen may be evolved as the Ag is electrooxidized to $Ag_2O$ at the anode, and no little, if any, hydrogen is evolved as the $Ag_2O$ is electroreduced to Ag at the cathode.

FIG. 1 illustrates a sectional view of the structure of pump 110 according to a specific example embodiment of the disclosure. Pump 110 comprises a $SiO_2$ membrane 120, comprising silica spheres 121, sandwiched between electrodes 130 and 140. Electrodes 130 and 140 each comprise a carbon paper substrate (131 and 141, respectively) covered with a reactive $Ag/Ag_2O$-coating (132 and 142, respectively). The 1.3 mm thick 8 mm diameter membrane may be formed by fusing phosphosilicic acid coated silica microspheres. These $Ag/Ag_2O$ electrodes may be consumed in a pumping process. Flow-through $Ag/Ag_2O$ anode 130 and cathode 140 may be formed of 280 μm thick 78% porosity carbon paper, on which silver is plated, followed by anodizing ½ of the silver.

Figure 2:
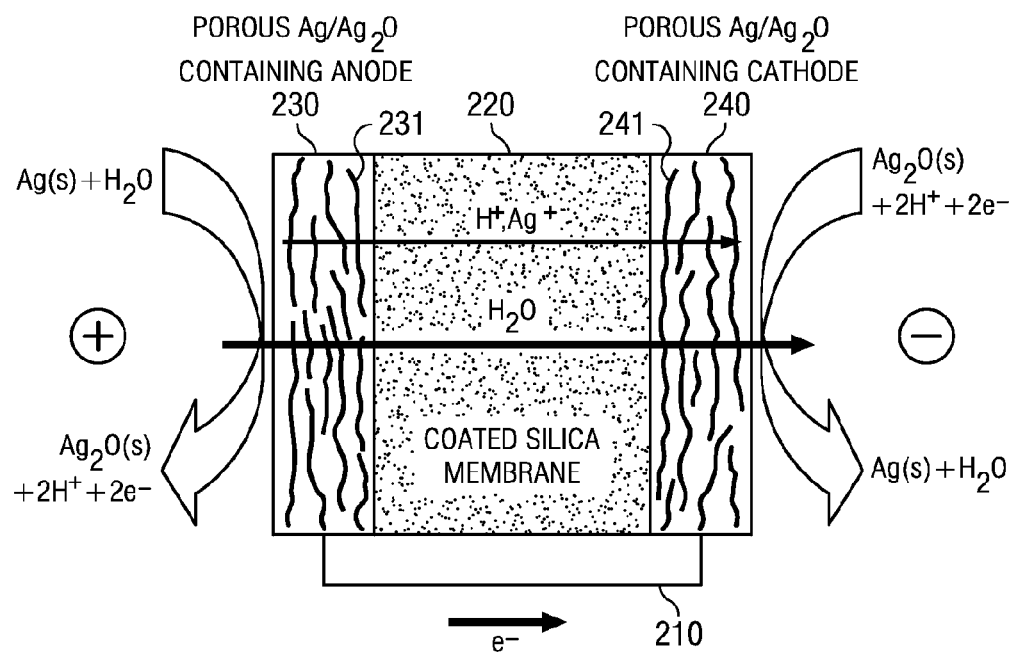
FIG. 2 illustrates a sectional view of a pump with electrode reactions and transport processes according to a specific example embodiment of the disclosure.

FIG. 2 illustrates a sectional view of pump 210, with electrode reactions, and transport processes according to a specific example embodiment of the disclosure. Pump 210 includes a pair of identical, porous $Ag/Ag_2O$-plated electrodes 230 and 240, each of which comprises a carbon paper substrate (231 and 241, respectively) covered with a $Ag/A_2O$ coating (232 and 242, respectively), sandwiching ceramic membrane 220. The electrochemically reactive component of porous anode 230 or cathode 240 may be applied by any method. For example, silver may be electrodeposited on the fibers of the carbon paper of the anode; the same material, in which part of the silver is chemically or electrochemically oxidized to silver oxide, may serve as the cathode. FIG. 2 illustrates that application of current (or voltage) across the anode 230 and cathode 240 may drive protons, produced in the anodic reaction $2Ag(s)+H_2O \rightarrow Ag_2O(s)+2H^++2e^-$, to the cathode, where they are consumed by the cathodic reaction $Ag_2O(s)+2H^++2e^- \rightarrow 2Ag(s)+H_2O$.

Figure 3A:
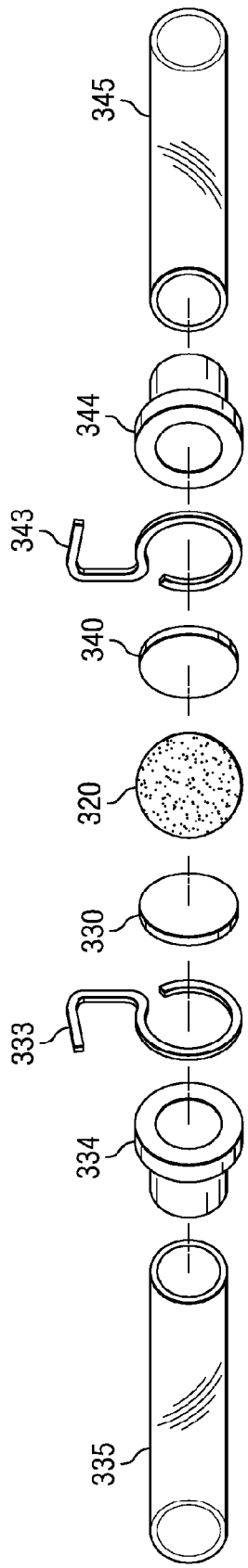
FIG. 3A illustrates an exploded view of the pump shown in FIG. 3B according to a specific example embodiment of the disclosure.

FIG. 3A illustrates an exploded view of a pump according to a specific example embodiment of the disclosure. FIG. 3A depicts the low-cost components of a pump. From left to right, the components are: silicon tubing 335, Pvc Frame 334, silver strip 333, $Ag/Ag_2O$-coated carbon paper anode 330, ceramic membrane 320, $Ag/Ag_2O$-coated carbon paper cathode 340, silver strip 343, PVC Frame 344, silicon tubing 345. The estimated cost of the depicted pump is $1.00 (in 2011 USD).

Figure 3B:
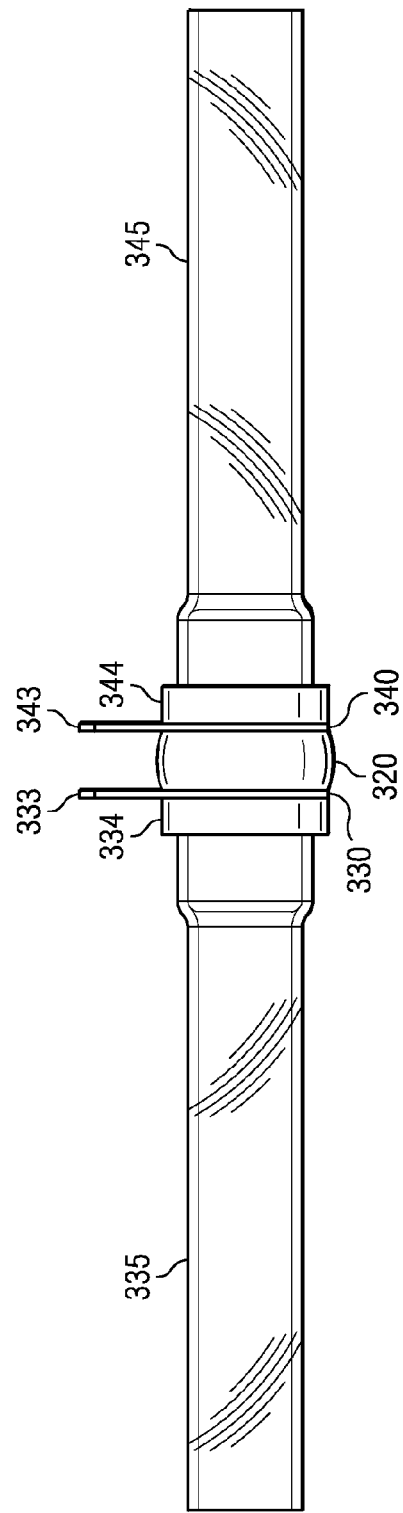
FIG. 3B illustrates an assembled pump according to a specific example embodiment of the disclosure.

FIG. 3B illustrates an assembled pump according to a specific example embodiment of the disclosure. From left to right, the components are: silicon tubing 335, PVC Frame 334, silver strip 333, $Ag/Ag_2O$-coated carbon paper anode 330, ceramic membrane 320, $Ag/Ag_2O$-coated carbon paper cathode 340, silver strip 343, PVC Frame 344, silicon tubing 345. The sandwiches may be encapsulated in an epoxy, with foil lips (e.g., silver foil lips) (333, 343) inserted between the membrane 320 and the electrodes 330, 340 for electrical contacting. An assembled electrode-membrane-electrode sandwiche may be washed with water from a syringe pump (e.g., Cole Parmer 780100C, Vernon Hills, Ill.) for 25 min at 10 μL $min^{-1}$ flow rate before use.

Reservoirs

An assembled pump may be inserted into a gap of a reservoir assembly. According to some embodiments, a reservoir assembly may comprise two compartments. In some embodiments, one compartment may contain pumped water or aqueous solution, and a second compartment may contain a drug solution or of a solution containing multiple drugs, stored in a reservoir suspension. In some embodiments, a reservoir may be made, for example, by molding a plastic. In some embodiments, either or both compartments may have a port or septum, such as a septum made of an elastomer, to allow their filling with the water or aqueous solution or with the drug solution or suspension. According to some embodiments, a reservoir assembly may have any desirable geometric configuration. Similarly, fluid chambers in a reservoir assembly may have, in some embodiments, any desired configuration. A reservoir assembly, for example, may have an annular shape. In some embodiments, an annular reservoir assembly may comprise a gap (e.g., for insertion of a pump) occupying a portion (e.g., less than about 20%, less than about 10%, less than about 5%, and/or less than about 3%) of the annular circumference. A reservoir assembly may be filled, for example, with a syringe. In some embodiments, either or both compartments may also have a hydrophobic vent allowing air or other gases to escape, for example during loading and/or operation. A vent may optionally comprise a hydrophobic porous material, to allow the escape of gases without allowing leakage of the water or aqueous solution or of a drug suspension or solution. Examples of hydrophobic porous vent materials include, but are not limited to, hydrophobic gas diffusion membranes optionally made of woven and non-woven fibrous perfluorinated polymers, exemplified by materials used in zinc air batteries, such as the Excellerator™ PTFE Gas Diffusion Membrane of W. L. Gore & Associates of Newark, DE. Venting air and/or other gases may reduce and/or prevent an undesirable pressure change in one or more chambers according to some embodiments. For example, heat (e.g., body heat, sunlight, and/or others) may lead to an increase in pressure that, if unchecked, may lead to an unplanned change in flow rate. This, in turn, may lead to under-dosing or over-dosing of a drug or other material in a delivery fluid.

One or more reservoir surfaces (e.g., surfaces that contact a pump fluid, a separator, and/or a delivery fluid) may be hydrophobic according to some embodiments. For example, a reservoir surface may be hydrophobic due to its intrinsic composition, chemical treatment, and/or application of a hydrophobic coating (e.g., a long-chain alkyl trialkoxysilane).

In some embodiments, a delivery fluid-containing compartment may contain an active pharmaceutical ingredient (e.g., a drug) concentrate in a non-aqueous solution or dispersion, or a solid comprising the active pharmaceutical ingredient (e.g., for longer shelf life). In some embodiments, an active pharmaceutical ingredient solution or suspension may be prepared prior to use, for example by adding water or an aqueous solution to the drug containing compartment prior to use. This may be desirable, for example, when the delivered active pharmaceutical ingredient is glucagon, available from Eli Lilly & Co. Indianapolis, Ind., because the shelf life of its typically injected solution is usually only about a day.

According to some embodiments, a pump may comprise means for metering (e.g., accurately metering) a fluid, means for pumping a fluid, and/or an implanted cannula. An implanted cannula may be connected, for example, through plastic tubing to a flow-causing pump, which pumps or delivers a defined volume of a drug containing solution, or of a solution containing multiple drugs, stored in a reservoir. In some embodiments, drug reservoir volumes may be varied by increasing the thickness and/or length of the reservoir. It may be desirable to increase reservoir volume by increasing chamber length, for example, in reservoirs that may be used in skin-adhered embodiments. In some embodiments, reservoir volumes scale with the cube of their linear dimensions. In some embodiments, a skin adhered system may be less than 12 mm OD. In some embodiments, dimensions and drug solution reservoir volumes for a system of 8 mm thickness are 36×30×8 mm, 1.0 mL; 53×47×8 mm, 2.7 mL; 78×72×8 mm, 7.0 mL. In some embodiments, dimensions and drug solution reservoir volumes for a system of 12 mm thickness may have a volume of 20 mL for a 78×72×12 mm system.

Figure 4A:
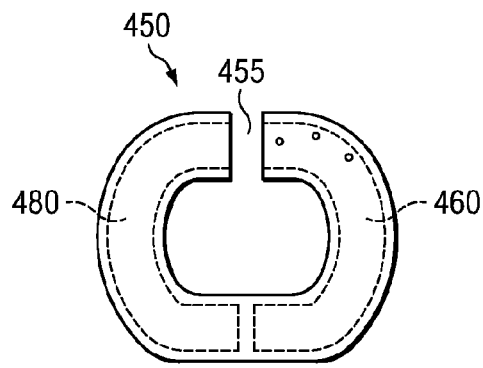
FIG. 4A illustrates a plan view of a reservoir system according to a specific example embodiment of the disclosure.
Figure 4B:
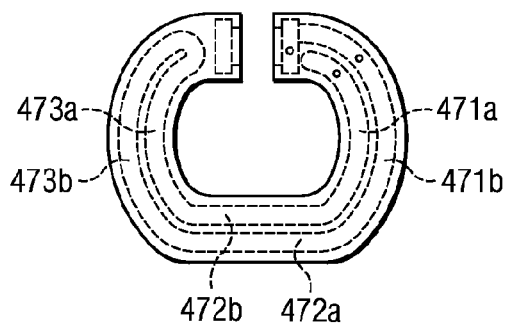
FIG. 4B illustrates a plan view of a 0.9 mL volume reservoir system according to a specific example embodiment of the disclosure.

FIG. 4A illustrates reservoir assembly 450 gap 455, pump fluid chamber 460 and delivery fluid chamber 480. An assembled pump (e.g., as shown in FIG. 3B) may be inserted into gap 455. FIG. 4B illustrates a plan view of reservoir assembly 451 having a delivery fluid volume of 0.9 mL. Reservoir assembly 451 comprises pump fluid chamber 460 and delivery fluid chamber 480. Pump fluid chamber comprises curvature 471a fluidly connected to straight section 472a, fluidly connected to curvature 473a, fluidly connected by hairpin 474a to curvature 473b, fluidly connected to straight section 472b, fluidly connected to curvature 471b.

Figure 4C:
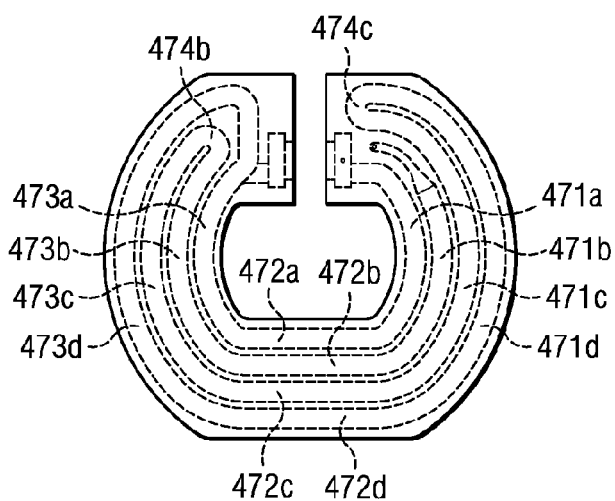
FIG. 4C illustrates a plan view of a 2.7 mL reservoir system according to a specific example embodiment of the disclosure.

FIG. 4C illustrates reservoir assembly 452 having a delivery volume of 2.7 mL. Pump fluid chamber 460 comprises curvature 471a, fluidly connected to straight section 472a, fluidly connected to a curvature 473a, fluidly connected to straight section 472a, fluidly connected to a curvature 473d, fluidly connected to a straight section 472d, fluidly connected to a curvature 471d, fluidly connected to hairpin 474c, fluidly connected to a curvature 471c, fluidly connected to straight section 472c, fluidly connected to hairpin 474b, fluidly connected to curvature 473b, fluidly connected to straight section 472b, fluidly connected to curvature 471b, fluidly connected to air vent 478.

Figure 4D:
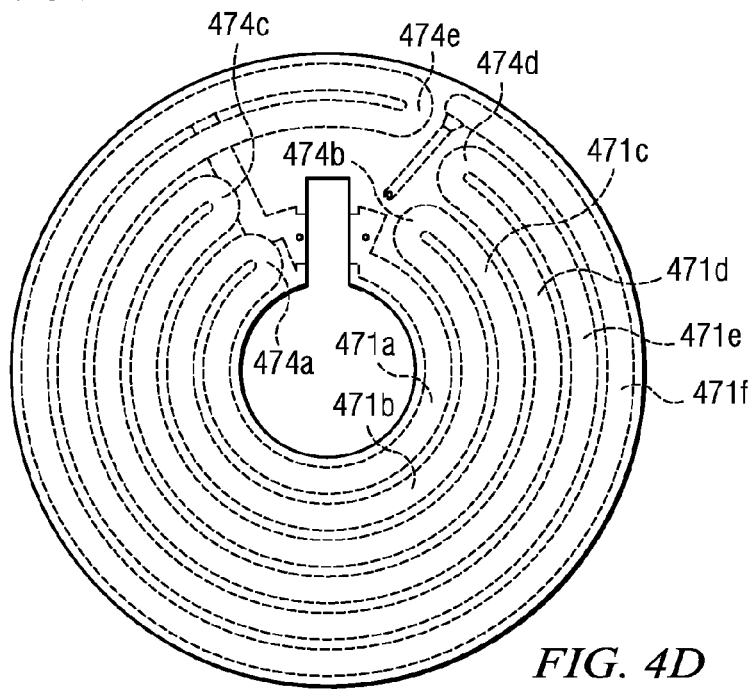
FIG. 4D illustrates a plan view of a 7.3 mL reservoir system according to a specific example embodiment of the disclosure.

FIG. 4D illustrates reservoir assembly 453 having a delivery volume of 7.3 mL. Pump fluid chamber 460 comprises curvature 471a, fluidly connected to hairpin 474a, fluidly connected to curvature 471b, fluidly connected to hairpin 474b, fluidly connected to a curvature 471c, fluidly connected to hairpin 474c, fluidly connected to curvature 471d, fluidly connected to hairpin 474d, fluidly connected to curvature 471e, fluidly connected to hairpin 474e, fluidly connected to curvature 471f, fluidly connected to air vent 478.

Figure 5A:
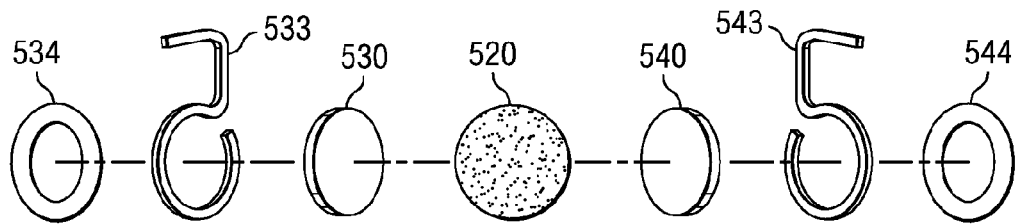
FIG. 5A illustrates an exploded view of a pump according to a specific example embodiment of the disclosure.

In some embodiments, components of a pump system may be manufactured at a low cost. FIG. 5A illustrates an exploded view of pump 510 according to a specific example embodiment of the disclosure. From left to right, the components are: PVC O-ring 534, silver strip 533, Ag/Ag$_2$O-coated carbon paper anode 530, ceramic membrane 520, Ag/Ag$_2$O-coated carbon paper cathode 540, silver strip 543 and PVC O-ring 544.

In some embodiments, assembled components of a pump system may be inserted into a reservoir gap. In some embodiments, a reservoir may contain a chamber for pumped water and a chamber for a delivery fluid. As displayed in FIGS. 4A-D, delivery fluid reservoir volumes may vary for use with a pump and a system described herein. In some embodiments, a system may comprise a reservoir with one or more hairpins.

Figure 5B:
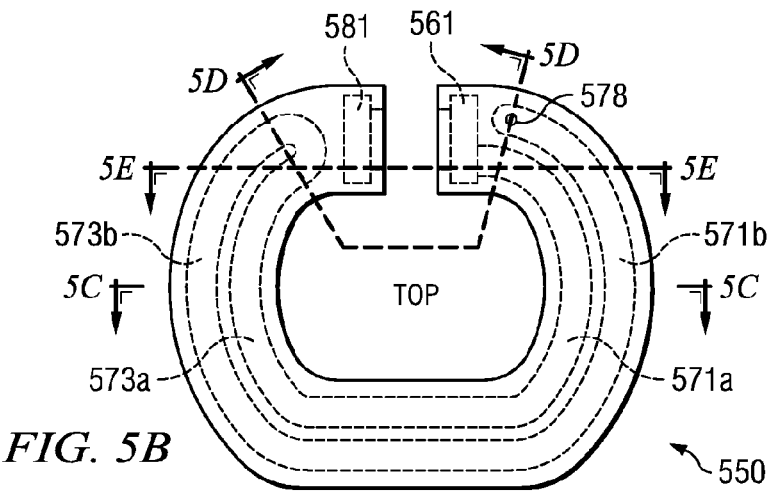
FIG. 5B illustrates a plan view of a reservoir system according to a specific example embodiment of the disclosure.

FIG. 5B illustrates a plan view of the reservoir system according to a specific example embodiment of the disclosure. FIG. 5B depicts a reservoir 550 for pumped water and drug chambers and a pump gap 555.

In some embodiments, a pump system (e.g., a functional drug infusion system) may comprise a reservoir with two chambers. In some embodiments, a reservoir may comprise a pump fluid chamber and a delivery fluid chamber. In some embodiments, each chamber may comprise an opening, a curved section, fluidly linked to a straight section, fluidly connected to a curved section, fluidly connected to a hairpin, fluidly connected to a curved section fluidly connected to a straight section and fluidly connected to a curved section. In some embodiments, a pump fluid chamber may comprise of a proximal end, medial end, and distal end. In some embodiments, a pump fluid chamber may comprise of a pump coupling. In some embodiments, a reservoir may comprise a pump fluid chamber assembly comprising an air inlet. In some embodiments, a reservoir may comprise a pump fluid chamber assembly comprising a pump fluid chamber fill inlet and septum. In some embodiments, a reservoir may comprise a pump fluid chamber assembly comprising pump fluid chamber distal fill inlet. In some embodiments, a pump fluid chamber may comprise of a proximal end, medial end, and distal end. In some embodiments, a pump fluid chamber may comprise a pump coupling. In some embodiments, a reservoir may comprise a delivery fluid chamber assembly comprising an air inlet. In some embodiments, a reservoir may comprise a delivery fluid chamber assembly comprising a delivery fluid chamber fill inlet and septum. In some embodiments, a reservoir may comprise a delivery fluid chamber assembly comprising a pump fluid fill inlet and septum. In some embodiments, a reservoir may comprise a delivery fluid chamber assembly comprising a delivery fluid outlet. In some embodiments, a delivery fluid chamber may comprise a proximal end, medial end, and distal end. In some embodiments, a delivery fluid chamber may comprise a pump coupling. A reservoir assembly may comprise, in some embodiments, a housing. A housing (e.g., a rigid and/or semi-rigid housing) may, for example, comprise any suitable plastics, polymers, acrylics, and/or other materials. A housing may be transparent and/or or opaque in some embodiments.

Figure 5C:
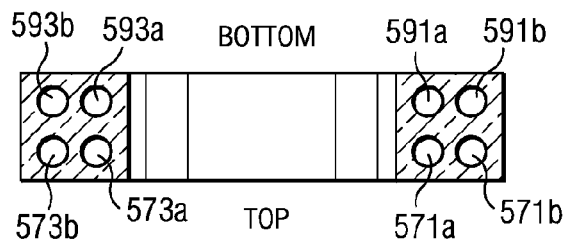
FIG. 5C is a sectional view of a reservoir system according to a specific example embodiment of the disclosure along section lines 5C-5C shown in FIG. 5B.

FIG. 5C is a sectional view of a reservoir system according to a specific example embodiment of the disclosure along section lines 5C-5C shown in FIG. 5B. FIG. 5C illustrates a sectional view of the top and bottom layer inlets and outlets of the reservoir system according to a specific example embodiment of the disclosure. The left side of FIG. 5C depicts the tubular hosing of curvatures 573a, 573b, 593a, 593b. Curvatures 573a and 573b are stacked directly over curvatures 593a and 593b. The right side of FIG. 5C depicts the tubular hosing of curvature 571a, 571b, 591a, 591b. Curvatures 571a and 571b are stacked directly over curvatures 591a and 591b.

Figure 5D:
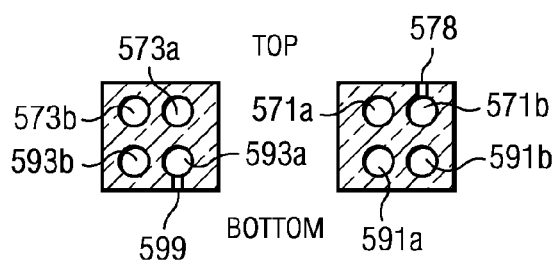
FIG. 5D is a sectional view of a reservoir system according to a specific example embodiment of the disclosure along section lines 5D-5D shown in FIG. 5B.

FIG. 5D is a sectional view of a reservoir system according to a specific example embodiment of the disclosure along section lines 5D-5D shown in FIG. 5B. The left side of FIG. 5D depicts the left side of reservoir 550, including delivery fluid outlet 599 of delivery fluid chamber 580. The left side of FIG. 5D depicts the tubular hosing of curvature 573a, 573b, 593a, 593b. Curvatures 573a and 573b are stacked directly over curvatures 593a and 593b, respectively. Curvature 593a also connects to delivery fluid outlet 599. The right side of FIG. 5D depicts the right side of reservoir 550, including air inlet 578 of the water chamber 560. The right side of FIG. 5D depicts the tubular hosing of curvatures 571a, 571b, 591a, 591b. Curvatures 571a and 571b are stacked directly over curvatures 591a and 591b.

Figure 5E:
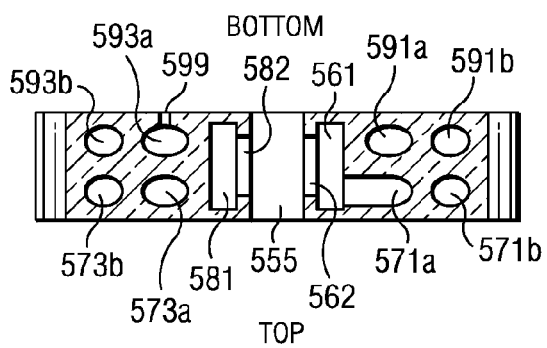
FIG. 5E is a sectional view of a reservoir system according to a specific example embodiment of the disclosure along section lines 5E-5E shown in FIG. 5B.

FIG. 5E is a sectional view of a reservoir system according to a specific example embodiment of the disclosure along section lines 5E-5E shown in FIG. 5B. This view illustrates gap 555, into which a pump may be inserted, and couplings 561 and 581 to which a pump may be fluidly coupled. It also illustrates delivery fluid outlet 599.

FIG. 5F illustrates an elevation view of the reservoir system shown in FIG. 5B according to a specific example embodiment of the disclosure. FIG. 5F depicts the delivery fluid outlet 599.

FIG. 5G is a sectional view of a reservoir system according to a specific example embodiment of the disclosure along section lines 5G-5G shown in FIG. 5F. FIG. 5G depicts a water chamber 560 of the reservoir system according to a specific example embodiment of the disclosure. opening 562 of water chamber 560 is fluidly connected to first curvature 571a, fluidly connected to straight section 572a, fluidly connected to second curvature 573a, fluidly connected to hairpin 574, fluidly connected to first curvature 573b, fluidly connected to straight section 572b, fluidly connected to second curvature 571b. FIG. 5G also depicts water chamber air inlet 578.

FIG. 5H illustrates a sectional view of a reservoir system according to a specific example embodiment of the disclosure along section lines 5H-5H shown in FIG. 5F. FIG. 5H depicts delivery fluid chamber 580 of a reservoir system, in which the opening of delivery fluid chamber 580 is fluidly connected to first curvature 593b, fluidly connected to straight section 592b, fluidly connected to second curvature 573b, fluidly connected to hairpin 594, fluidly connected to first curvature 591a, fluidly connected to straight section 592a, fluidly connected to second curvature 593a.

In some embodiments, a top chamber may comprise pumped water. In some embodiments, a bottom chamber may comprise a delivery fluid solution. In some embodiments, a diameter channel for a chamber may be less than 3 mm. In some embodiments, a channel diameter (e.g., ID and/or OD) may be vary along its length.

FIG. 5I illustrates a generally isometric view of the reservoir system shown in FIGS. 5B-5H. FIG. 5I depicts the water chamber proximal fill inlet 563. FIG. 5I depicts the opening on the left top layer of the water chamber which comprises a cone or funnel 562.

Figure 5J:
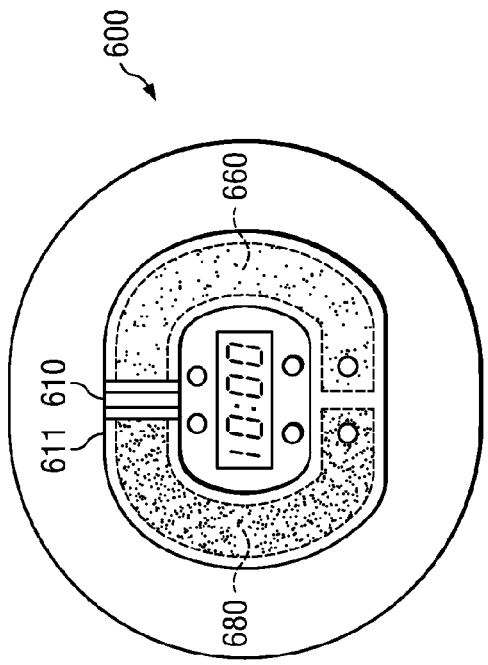
FIG. 5J illustrates a generally isometric view of the reservoir system shown in FIGS. 5B-5I.

FIG. 5J illustrates a generally isometric view of the reservoir system shown in FIGS. 5B-5I. FIG. 5J depicts the opening on the right bottom layer of the delivery fluid chamber, which comprises a cone or funnel 582.

Pump Systems

Pumps may be configured to deliver medications continuously and/or intermittently according to some embodiments. For example, insulin pumps used by patients with diabetes, particularly Type 1 diabetes, may be programmed to deliver insulin continuously at a basal delivery rate, in accordance with a programmed or programmable delivery profile(s), and also may be programmed to deliver insulin boluses (e.g., specific doses of a drug delivered in a predetermined time period, for example, less than 1 hour, less than 30 minutes, less than 10 min, and/or less than 5 min.), usually in conjunction or anticipation of carbohydrate intake (e.g., meals) or anticipated or onset of glycemic excursions. While insulin increases the consumption of glucose by cells of the body, glucagon induces conversion of stored glycogen to glucose, increasing the concentration of glucose in body fluids. In the management of diabetes, a pump system may deliver glucagon and/or insulin. A two-pump system comprising both an insulin pump and a glucagon pump may be of particular value in diabetes management because it may allow both up and down adjustment of the glycemia and may decrease the duration and/or likelihood of the unwanted hyperglycemic and/or hypoglycemic periods.

Fluid pumps (e.g., drug pumps) may also be used to deliver a material (e.g., a biological and/or chemical) having a short half-life in the body of a subject. Examples of short-lived chemicals may include, in some embodiments, short-lived antibiotics, like gentamicin, tobramycin and cefotaxime. Gentamicin is not well absorbed when orally administered, but is well absorbed when subcutaneously and intramuscularly delivered. Its elimination half-life in patients with normal renal function may be as short as 2 hours, making its continuous and/or frequent delivery potentially advantageous. Gentamicin may be used, for example, in the treatment of severe infections by Gram-negative bacteria like *Streptococus aureus* and is used, for example, in treating septicaemia, neonatal sepsis, neonatal meningitis, biliary tract infection, pyelonephritis, prostatitis and endocarditis. Tobramycin may have a serum half life in normal individuals of about 2 hours. It may be effective, for example, against pneumonia, particularly when caused by *Pseudomonas aeruginosa*. Cefotaxime has an elimination half life of merely 1.1 hours, making its continuous and/or frequent pumping potentially of particular interest. It may be effective in treatment of infections of the respiratory tract, skin, bones, joints, urogenital system, meningitis, and septicemia caused by many Gram-negative bacteria. It is, for example, active against penicillin-resistant strains of *Streptococcus pneumoniae*.

In some embodiments, active pharmaceutical ingredients that may be pumped include, heparin (e.g., used to control blood coagulation), interferon (e.g., used in the therapy of C-type hepatitis) or ketamine (e.g., used in pain management, for example, in conjunction with opioid drugs like morphine and its derivatives). Pumping in accordance with some embodiments of the disclosure may also be desirable (e.g., advantageous) when therapy is better achieved by maintaining a substantially constant concentration of a drug or substance in a body fluid, such as serum, and/or when therapy requires selective drug delivery to targeted organ or tissue (e.g., as is the case in chemotherapy of most cancers).

In some embodiments, a device delivering fluids (e.g., drugs) may include a pump (e.g., drug pump, insulin pump), a reservoir, a controller, one or more sensors, or combinations thereof. A fluid pump system (e.g., a medication pump system) may comprise, in some embodiments, flow-causing components, metering components (e.g., accurate drug dosing components), and/or an implanted needle or cannula, the needle or cannula connected through a plastic tubing to a flow-causing pump. A fluid delivery system may pump- and/or deliver a defined volume of a fluid (e.g., drug containing solution and/or a solution containing multiple drugs), stored in a reservoir. A needle may be optionally short, its length between about 0.3 cm and about 1 cm, and its gauge may be, for example, between about 22 and about 32 and/or between about 26 and about 29. A needle (e.g., a narrow gauge needle), may be optionally inserted in order to reduce the extent to which its presence is felt by the wearer of the skin-attached drug pumping system in the skin of the belly, the tip of the needle residing in the fatty tissue may often be found below the skin of the belly. A needle may be inserted in an intravenous port in some embodiments. A delivery fluid, according to some embodiments, may comprise a pharmaceutical agent used to treat a condition requiring treatment in humans or in animals, a nutrient, a nutrient supplement, and/or a vaccine. Insulin may be an example of a drug in some embodiments. A delivery fluid comprising a drug may further include a solution in which the drug may be dissolved and/or dispersed.

A pump system, in some embodiments, may comprise a reference electrode. For example, a reference electrode may be included to monitor potentials relative to an anode and/or a cathode. A reference electrode may be desired, in some embodiments, to monitor the presence of reactant. For example, the potential between an anode and a reference electrode or between a cathode and a reference electrode may rise when reactant at the anode or cathode, respectively, has been depleted. A controller may be configured to terminate flow upon detecting a potential relative to a reference electrode within a range (e.g., a predetermined range) and/or above a threshold (e.g., a preset threshold).

In some embodiments, a volume and/or delivery rate of a drug or drug solution, described herein, may be controlled by a pump system. In some embodiments, a pump system may comprise a pump connected to a computer (e.g., a personal computer, microcontroller, or the like) via an external interface. In some embodiments, a system may be controlled, for example by an external interface comprising an interface cable for an external interface option to an external controller comprising a 3V lithium battery, and one or more control buttons. In some embodiments, control buttons may allow, for example, programming of a current to be applied to a pump, and time duration of such application. In some embodiments, a system may comprise a transmitter and/or receiver. In some embodiments, a system may comprise an alarm. In some embodiments, a system may comprise a reusable, removable ("pop-out") electronic package in its center. In some embodiments, an electronic package may comprise a constant current supply and an LCD or an electrophoretic (e.g., E-sink) or another display. In some embodiments, a removable electronic package may comprise an electrically coupled processor, memory, user interface, (i.e., one or more control buttons) and a power source. In some embodiments, an electronic system may comprise a wireless controller. In some embodiments, an electronic system may comprise RF communication. In some embodiments, an electronic system may comprise blue-tooth technology. A controller may be contained within the unit that is physically connected to a pump (e.g., a catheter) or it may be spaced away and/or operate remotely in some embodiments. A controller may be contained, for example in a wrist watch and/or a mobile communication device (e.g., a cell phone).

Figure 6B:
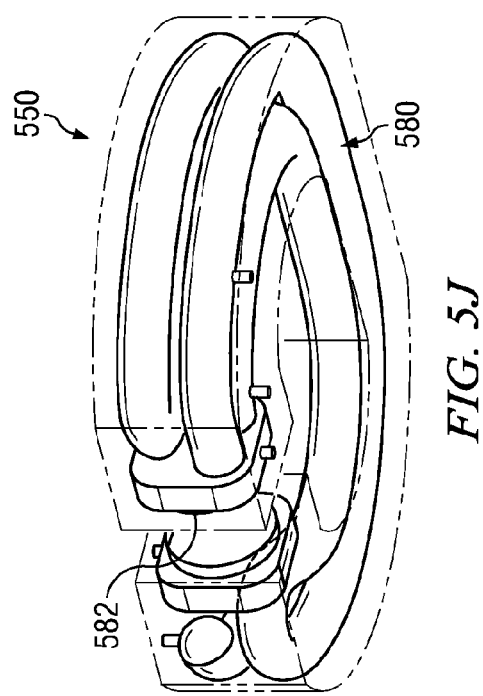
FIG. 6B illustrates a plan view of a pump system according to a specific example embodiment of the disclosure.
Figure 6A:
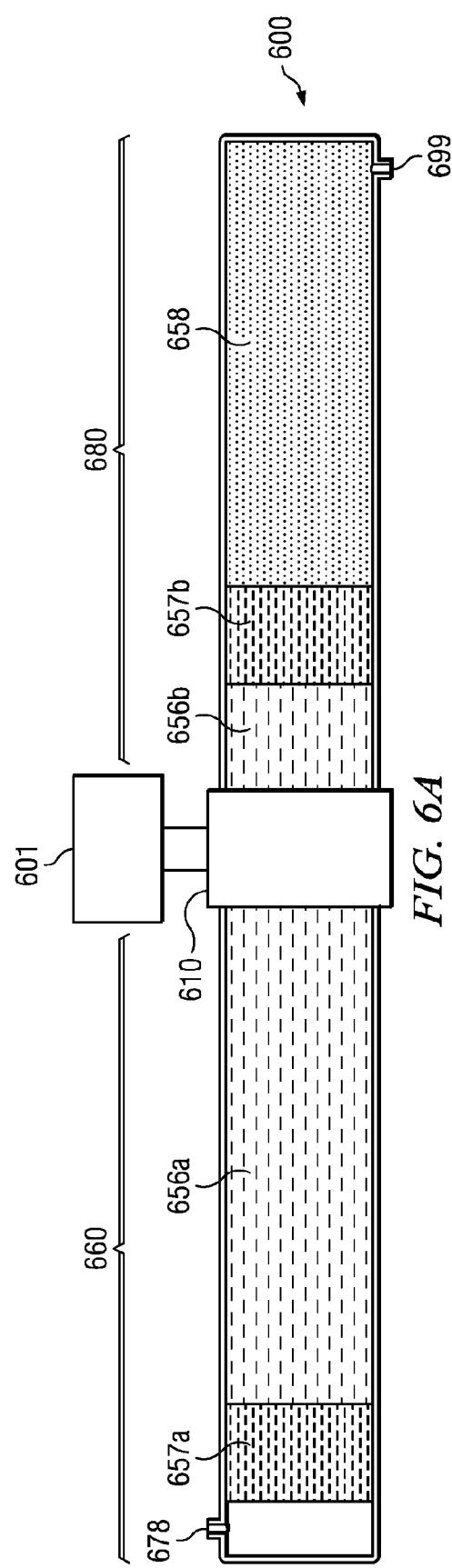
FIG. 6A illustrates an elevation view of a pump system according to a specific example embodiment of the disclosure.

FIG. 6A illustrates an elevation view of pump system 600 comprising pump 610, pump fluid chamber 660, delivery fluid chamber 680, air-inlet 678, delivery fluid outlet 699, and controller 601, according to a specific example embodiment of the disclosure. Compared to FIG. 6B, pump fluid chamber 660 and delivery fluid chamber have been straightened, for illustration purposes, to be collinear with pump 610. FIG. 6A depicts a pump fluid chamber 660 filled with a separator 657*a* in fluid communication with a first aliquot of pump fluid 656*a* and delivery fluid chamber 680 is filled with a second aliquot of pump fluid 656*b*, in fluid communication with separator 657*b* and fluidly connected to delivery fluid 658. A separator may be a liquid or a solid. Examples of a liquid separator may include, for example, silicone oil or a glycerol mono or di-ester of a fatty acid. Solid separators may be plastic, ceramic or metallic in some embodiments. Once pumping begins pump fluid 656*a* from pump fluid chamber 660 passes through pump 610 and begins to accumulate in delivery fluid chamber 680 and push separator 657*b*, which pushes delivery fluid 658 to outlet 699.

Figure 6C:
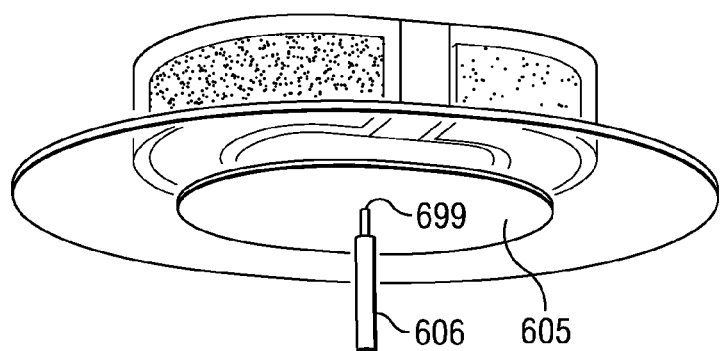
FIG. 6C illustrates an isometric view of a pump system according to a specific example embodiment of the disclosure.
Figure 6D:
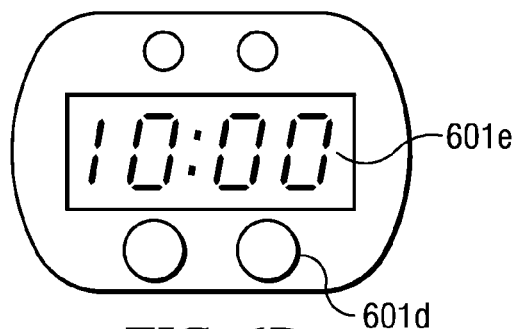
FIG. 6D illustrates a plan view of a constant current/voltage controller and timer according to a specific example embodiment of the disclosure.

FIG. 6B illustrates miniature skin-adhered fluid-delivery system 600 shown in FIG. 6A in accordance with certain exemplary embodiments. FIG. 6B depicts a delivery fluid chamber 680, pump 610, controller 601, and pump fluid chamber 660. Delivery fluid 658 (e.g., a drug-containing solution) is densely speckled and pump fluid 656 is lightly speckled. The structure at the top-center of FIG. 6B (i.e., separating pump fluid compartment 660 from delivery fluid compartment 680) depicts electro-osmotic pump 610 disclosed herein. Its outer diameter is 8 mm. The large transparent plastic disc mimics the skin. It is penetrated by a 5 mm long 29 gauge syringe needle 606 as shown in FIG. 6C. System 600 is adhered to the transparent plate that mimics the skin with two-sided adhesive tape 605. As depicted, system 600 has reusable, removable ("pop-out") electronic package 601 in its center (FIG. 6D-5G). As depicted in the embodiment of FIG. 6B, pump fluid chamber 660 of system 600 may contain pump fluid 656*a* and delivery fluid chamber 680 may contain delivery fluid 658 (e.g., insulin mimic), which does not pass through pump 610. According to this embodiment, a pump's active area may be about 0.3 cm$^2$. Delivery fluid chamber 680 may also include separator 657*b* separating pump fluid 656*b* and delivery fluid 658. During operation, separator 657*b* moves as pump fluid 656*b*, shown colorless, displaces delivery fluid 658.

The large transparent plastic disc to which system 600 is attached, mimics skin for illustration purposes and may be replaced in actual use by human or animal skin. This plastic disc is penetrated by syringe needle 606 as shown in FIG. 6C. FIG. 6C illustrates an isometric view of a pump system according to a specific example embodiment of the disclosure. When delivery fluid 658 is pushed out of the drug outlet 699 it reaches needle 606, which is inserted into a subject. FIG. 6C depicts an embodiment comprising an adhesive patch 605 for attachment of the system to a subject. In some embodiments, the needle may be an about 5 mm long, about 29 gauge syringe needle 606. According to the depicted embodiment, the system is adhered to the transparent plate that mimics the skin with two-sided adhesive tape 605. In other embodiments, the system may be attached to a subject using an elastic band. Optionally, a needle may be longer than Optionally, a needle may be longer than about 5 mm (e.g., longer than about 7 mm), and/or shorter than 9 mm. In some embodiments, a needle may be inserted in a subject (e.g., the skin). The angle of insertion (e.g., relative to the plane of the skin) may be from 15° to about 45° versus the plane of the skin. The angle of insertion (e.g., relative to a line normal to the skin) may be from about 75° to about 45°. A needle may have a diameter from about 31 gauge to about 23 gauge.

FIG. 6D illustrates a plan view of a constant current/voltage controller and timer according to a specific example embodiment of the disclosure. FIG. 6D depicts a controller 601, comprising a user interface 601d, LCD display 601e, an electrically coupled processor 601a, memory 601b, and power source 601c. As depicted controller 601 of FIG. 6D further comprises two control buttons 601d for programming of the current to be applied to pump 610, and the time (e.g., duration and/or interval) of such application. These two settings (i.e., the combination of current and time) may define the delivered volume and/or the delivery rate (i.e., the flow rate). According to the depicted embodiment, the dimensions of the system are 36 mm×30 mm×8 mm.

Figure 6E:
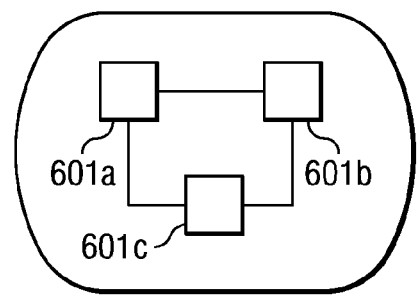
FIG. 6E illustrates a plan view of a constant current/voltage controller and timer according to a specific example embodiment of the disclosure.

FIG. 6E illustrates a plan view of a constant current/voltage controller and timer according to a specific example embodiment of the disclosure. FIG. 6E depicts an electrically coupled processor 601a, memory 601b, and power source 601c.

Figure 6F:
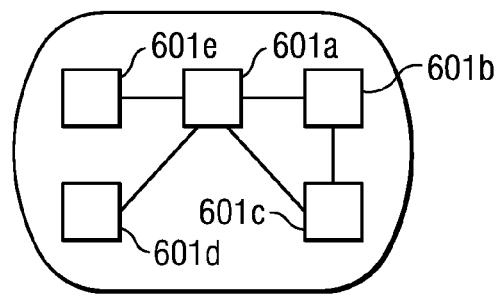
FIG. 6F illustrates a plan view of a constant current/voltage controller and timer according to a specific example embodiment of the disclosure.

FIG. 6F illustrates an exploded view of the controller shown in FIG. 6E according to a specific example embodiment of the disclosure. FIG. 6F depicts a processor 601a, memory 601b, and power source 601c electrically coupled, and a LCD display 601e and user interface 601d.

FIGS. 7A-7C illustrate embodiments of system 700 comprising reservoir assembly 750 in which pump fluid chamber 760 and delivery fluid chamber 780 have been rendered, for illustration purposes, as coplanar with each other and with pump 710 similar to the collinear arrangement shown in FIG. 6A. Pump fluid chamber 760 and delivery fluid chamber 780 may be configured as illustrated or may be configured such that pump fluid chamber 760 substantially overlays delivery fluid chamber 780 and the two together define, at least partially, an oval and/or a circle (e.g., as shown in FIGS. 4B-4D).

FIG. 7A illustrates a sectional view of pump system 750 according to a specific example embodiment of the disclosure. Pump 710 comprises membrane 720, anode 730, and cathode 740. Pump fluid chamber assembly 760 depicted in FIG. 7A, is located to the left of pump 710 and pump fluid chamber opening 765 is coupled with pump coupling 761, which is fluidly coupled to pump 710. Coupling 761 includes cone 762, the diameter of which expands (from left to right) from the insider diameter of pump fluid chamber 760 to the diameter of membrane 720. FIG. 7A depicts a proximal end 767, a medial portion 770 and a distal end 775 of pump fluid chamber 760. Pump fluid chamber 760 comprises 3 external fluid connections, namely air inlet 778 for admitting air into pump fluid chamber 760 during pump operation; separator distal fill inlet 776 and septum 777 for installing a volume (e.g., a small volume) of a separator fluid in pump fluid chamber 760; and pump fluid inlet 763 and septum 764 for loading a volume (e.g., a small volume) of pump fluid in pump fluid chamber 760 in contact with pump 710.

Pump 710 is fluidly connected to delivery fluid chamber assembly 780 via pump coupling 781 through delivery fluid chamber opening 785 of the delivery fluid chamber 780. Coupling 781 includes cone 782, the diameter of which narrows (from left to right) from the diameter of membrane 720 to the insider diameter of delivery fluid chamber 780. Delivery fluid chamber 780 comprises a proximal end 787, medial portion 790 and distal end 795. Medial portions 770 and 790 may include various curvatures, straight sections, and/or hairpins according to some embodiments (e.g., FIGS. 4B-4D). Proximal end 767 and 787 and distal ends may 775 and 795 may independently include various curvatures, straight sections, and/or hairpins according to some embodiments. Delivery fluid chamber 780 also comprises 4 external fluid connections, namely pump fluid inlet 783 and septum 784 for loading a volume (e.g., a small volume) of pump fluid in delivery fluid chamber 780 in contact with pump 710; separator fluid inlet 796 and septum 797 for installing a volume (e.g., a small volume) of a separator fluid in delivery fluid chamber 780; delivery fluid inlet 798 and septum 798a for installing a volume of a delivery fluid in delivery fluid chamber 780 (e.g., filling chamber 780); and delivery fluid outlet 799.

FIG. 7B illustrates a sectional view of pump system 750 according to a specific example embodiment of the disclosure. FIG. 7B depicts the same components depicted in FIG. 7A. FIG. 7C illustrates a sectional view of pump system 750 according to a specific example embodiment of the disclosure. FIG. 7C depicts the same components depicted in FIG. 7A. In some embodiments, the shape and/or relative location of coupling 761, cone 762, opening 765, coupling 781, cone 782, and/or opening 785 may impact the flow of fluids through pump 710. It may be desired and/or required to arrange coupling 761, cone 762, opening 765, coupling 781, cone 782, and/or opening 785 in an oblique configuration (e.g., FIG. 7A), a linear, centered configuration (e.g., FIG. 7B), a linear, off-center configuration (e.g., FIG. 7C).

In some embodiments, an outer diameter of an electro-osmotic pump may be about 1 cm or less, for example, about 0.8 cm or less. Thus the cross-sectional area of a pump may be less than 1 cm$^2$, less than 0.8 cm$^2$, and/or about 0.5 cm$^2$ or less. In some embodiments, a pump may be powered by a small cylindrical, optionally coin-type, battery with an OD of, for example, less than 13 mm, less than 8 mm, and/or less than 6 mm. A battery may be a nominally about 1.4 V open circuit voltage (OCV) alkaline Zn-air battery. Alternatively, a pump may be powered by a nominally about 1.4 V OCV alkaline Zn-manganese dioxide battery, or by a nominally about 1.6 V OCV Zn-silver oxide battery, or by a nominally about 2.8 V or higher OCV lithium anode battery, such as the 3.2 V OCV Li-manganese dioxide battery. A pump in some embodiments may provide a flow rates of about 1-40 µL/min. In some embodiments, with an about 3 V OCV lithium anode battery, a flow rate of between about at least 20 µL/min and about 40 µL/min may be sustained. In some embodiments, a typical flow rate may be sustained with a 1.6 V zinc-silver oxide battery between about at least 5 µL/min and about 18 µL/min. In some embodiments, a 1.4 V zinc-manganese dioxide alkaline battery may sustain a flow rate between about 3 µL/min and about 15 µL/min. In some embodiments, a flow rate of about 3 µL/min may be sustained at about 100 µA applied current; about 6 µL/min at 300 µA; about 10 µL/min at 500 µA; about 16 µL/min at 700 µA. Some examples of small batteries that can be used are shown in Table 1. All have sufficient capacity for electro-osmotically pumping at least about 16 mL of the solutions disclosed here, containing enough insulin for at least about a month or about 100 meals.

According to some embodiments, a pump system may comprise one or more sensors. For example, a pump may contain a sensor for detection of the volume of delivery fluid administered to a subject. Delivery fluid volume may be assessed by, for example, monitoring the position of a separator. In some embodiments, a separator may be colored (e.g., using a visible ink or dye, a luminescent agent, a phosphorescent agent, or the like). A sensor (e.g., a photosensitive film) may be positioned sufficiently close to the marked separator to permit the film to detect separator movement (e.g., adhered to a pump system housing). A sensor may be arranged in communication with a controller, according to some embodiments. A controller in communication with a sensor may adjust the potential difference and/or a current across a membrane (e.g., to adjust delivery to a desired flow rate, dose, volume, duration, or the like).

TABLE 1

Exemplary Useful Batteries

| Battery | Stock number | Thickness | OD | Weight | Voltage | Capacity |
|---|---|---|---|---|---|---|
| Zinc Air | L10ZA | 3.6 mm | 5.8 mm | 0.31 g | 1.4 V | 84 mW·h |
| Silver Oxide | Energ.364/363 | 2.15 mm | 6.80 mm | 0.37 g | 1.55 V | 28 mW·h |
| Silver Oxide | Energ.377/376 | 2.60 mm | 6.80 mm | 0.42 g | 1.55 V | 32 mW·h |
| Lithium | Energ.CR1025 | 2.50 mm | 10.00 mm | 0.70 g | 3.0 V | 60 mW·h |
| Lithium | Energ.CR1220 | 2.00 mm | 12.50 mm | 0.78 g | 3.0 V | 80 mW·h |

Loading Methods for Pump Systems

FIGS. 8A-8E illustrate steps for loading reservoir assembly 850 in which pump fluid chamber 860 and delivery fluid chamber 880 have been rendered, for illustration purposes, as coplanar with each other and with pump 810 similar to the collinear arrangement shown in FIG. 6A and FIGS. 7A-7C. Pump fluid chamber 860 and delivery fluid chamber 880 may be configured as illustrated or may be configured such that pump fluid chamber 860 substantially overlays delivery fluid chamber 880 and the two together define, at least partially, an oval and/or a circle (e.g., as shown in FIGS. 4B-4D).

FIG. 8A illustrates a sectional view of pump system 800 in which pump fluid chamber 860 is loaded with pump fluid 856a through pump fluid inlet 863 (arrow) according to a specific example embodiment of the disclosure. FIG. 8B illustrates a sectional view of pump system 800 in which pump fluid chamber 860 is loaded with separator fluid 857a through separator fluid inlet 876 (arrow) according to a specific example embodiment of the disclosure. FIG. 8C illustrates a sectional view of pump system 800 in which delivery fluid chamber 880 is loaded with pump fluid 856b through pump fluid inlet 883 (arrow) according to a specific example embodiment of the disclosure. FIG. 8D illustrates a sectional view of pump system 800 in which delivery fluid chamber 880 is loaded with separator fluid 857b through separator fluid inlet 896 (arrow) according to a specific example embodiment of the disclosure. FIG. 8E illustrates a sectional view of pump system 800 in which delivery fluid chamber 880 is loaded with delivery fluid 858 through delivery fluid inlet 898 (arrow) according to a specific example embodiment of the disclosure.

Figure 9C:
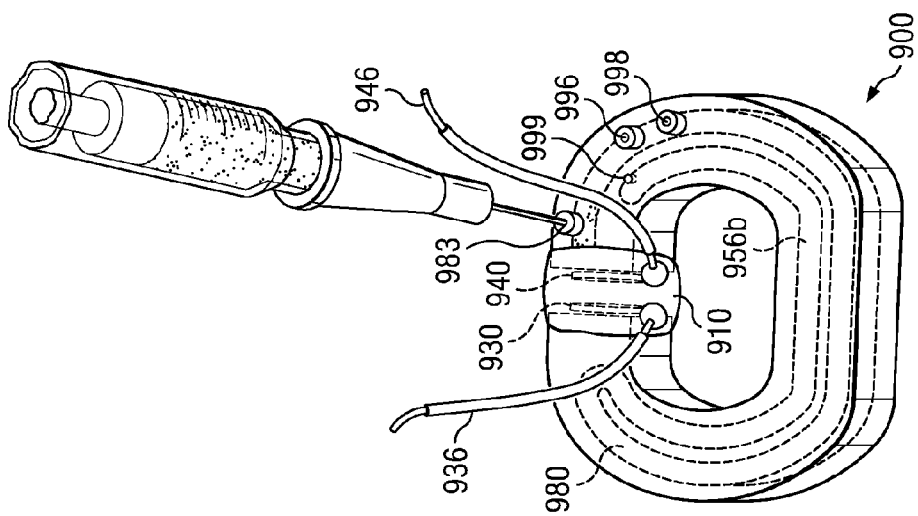
FIG. 9C illustrates an isometric view of the pump system shown in FIG. 9B (flipped over relative to FIG. 9B) in which the drug chamber is being filled with a water primer according to a specific example embodiment of the disclosure.
Figure 9B:
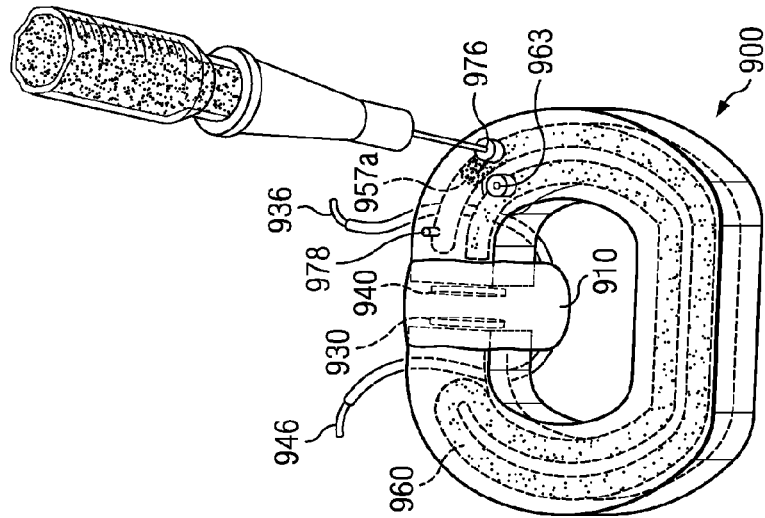
FIG. 9B illustrates an isometric view of the pump system shown in FIG. 9A in which the water-filled water chamber is being capped with oil according to a specific example embodiment of the disclosure.
Figure 9A:
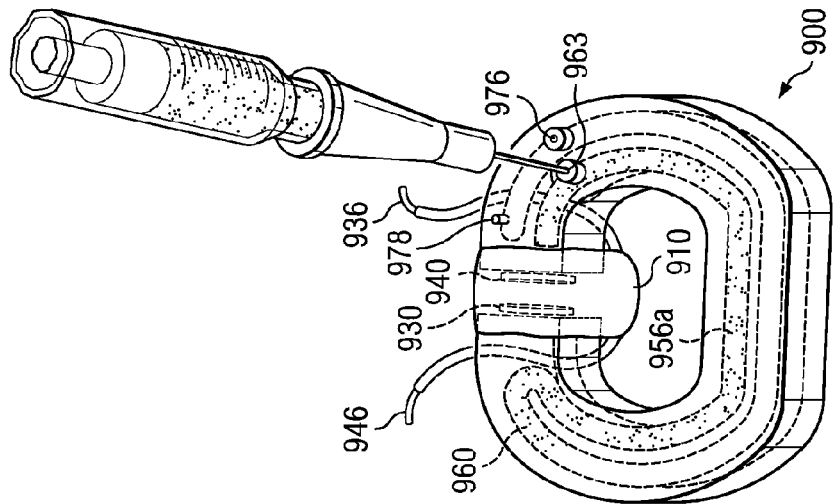
FIG. 9A illustrates an isometric view of a pump system according to a specific example embodiment of the disclosure in which the water chamber is being filled with water.
Figure 9D:
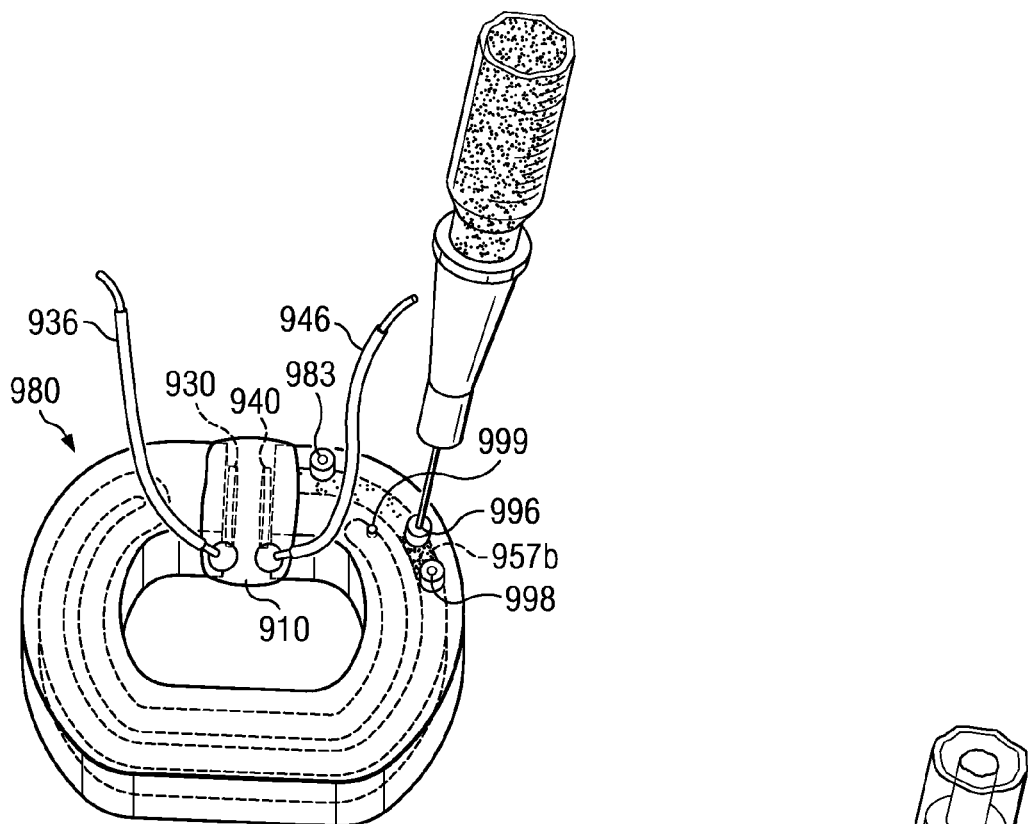
FIG. 9D illustrates an isometric view of the pump system shown in FIG. 9C in which the drug chamber is being filled with an oil divider according to a specific example embodiment of the disclosure.
Figure 9E:
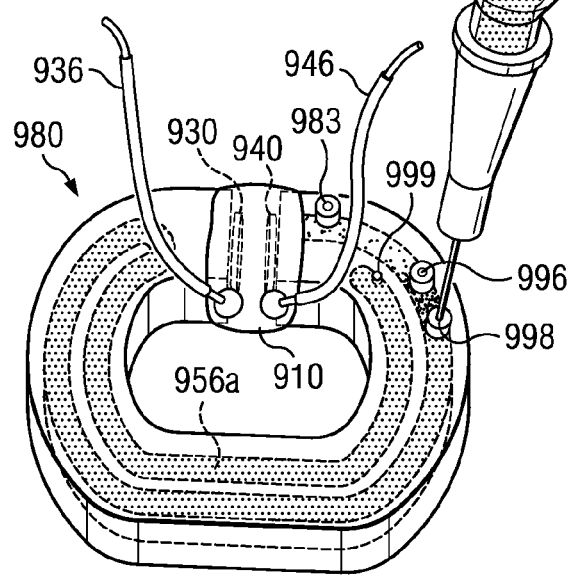
FIG. 9E illustrates an isometric view of the pump system shown in FIG. 9D in which the drug chamber is being filled with a drug-containing fluid according to a specific example embodiment of the disclosure.

FIGS. 9A-9E illustrate steps for loading pump system 900, which comprises pump 910, water chamber 960, and drug solution chamber 980 and parallel FIGS. 8A-8E. Wires 936 and 946 are in electrical communication with anode 930 and cathode 940, respectively, of pump 910. FIG. 9A illustrates an isometric view of pump system 900 in which water chamber 960 is loaded with water 956a through water inlet 963 according to a specific example embodiment of the disclosure. FIG. 9B illustrates an isometric view of pump system 900 in which water chamber 960 is loaded with oil 957a (black) through oil inlet 976 according to a specific example embodiment of the disclosure. FIG. 9C illustrates an isometric view of pump system 900 (flipped over relative to FIG. 9B-note wires 935 and 945) in which drug solution chamber 980 is loaded with drug solution 956b through drug solution inlet 983 according to a specific example embodiment of the disclosure. FIG. 9D illustrates an isometric view of pump system 900 in which drug solution chamber 980 is loaded with oil 957b (black) through oil inlet 996 according to a specific example embodiment of the disclosure. FIG. 9E illustrates an isometric view of pump system 900 in which drug solution chamber 980 is loaded with drug solution 958 (speckled) through drug solution inlet 998 according to a specific example embodiment of the disclosure. In some embodiments, drug outlet 999 may be fluidly connected to a catheter or needle inserted into a subject (e.g., when used). It may be desirable and/or required, according to some embodiments, to complete one or more of the loading steps shown in FIGS. 9A, 9B, 9C, 9D, and/or 9E in a one or more facilities (e.g., manufacturing facilities). In some embodiments, an end user may optionally complete one or more of the loading steps shown in FIGS. 9A, 9B, 9C, 9D, and/or 9E. For example, an end user may complete the loading step shown in FIG. 9E (e.g., immediately prior to use).

Pump System Operation

According to some embodiments, a fluid pump system (e.g., a medication pump system) may deliver a fluid (e.g., an insulin solution and/or suspension) stored in a reservoir connected by a tubing to a cannula implanted in a body tissue. A fluid may be delivered, for example, subcutaneously, optionally into fatty tissue; or intramuscularly. According to some embodiments, a cannula, (e.g., a plastic cannula) and/or a small gauge hollow needle (e.g., a stainless steel needle) may be implanted in the body of a subject for fluid delivery. A cannula and/or needle may be connected through a plastic tubing to the source of a pumped fluid (e.g., drug). For the intravenous delivery a hollow needle (e.g., connected to a fluid pump through a tubing) may be inserted in a septum of an intravenous port, connected by a catheter to a vein (e.g., a portacath). Ports may be used, for example, to treat hematology and oncology patients.

In some embodiments, a dissolved or solution-dispersed chemical (e.g., an active pharmaceutical ingredient) may be delivered to a tissue of a subject (e.g., subcutaneously, intravenously, intramuscularaly, intraperitoneally, and/or intrathecally). In some embodiments, a medication delivery system may be of a type that delivers insulin stored in a remote reservoir connected by the tubing to a cannula, or in a unit that is skin mounted or attached with its cannula connected by a short tubing. In some embodiments, the volume of a fluid delivery system (e.g., a medication infusion system) may be smaller than about 100 cm$^3$, for example, smaller than about 20 cm³, and, for example, smaller than about 10 cm³, for example, smaller than about 5 cm³. In some embodiments, a reservoir may contain a sufficient volume of drug solution or dispersion for about 1-10 day therapy, in some cases about 2-3 day therapy, and often about 1 day therapy.

A delivery fluid may comprise, according to some embodiments, a biological and/or chemical material. For example, a delivery fluid may comprise an active pharmaceutical ingredient (API) (e.g., a drug). A delivery fluid may be or may comprise an API as or in a solution, a suspension, and/or an emulsion in some embodiments. A delivery fluid may comprise one or more excipients (e.g., pharmaceutically acceptable excipients). For example, a delivery fluid may comprise any pharmaceutically acceptable vehicle for an API. A non-aqueous vehicle may comprise, in some embodiments, vegetable oils, polyethylene glycols, esters (e.g., ethyl oleate) and the like. A vehicle may comprise, in some embodiments, one or more antibacterial preservatives, antioxidants, tonicity agents, buffers, stabilizers, and/or other components.

An API may be and/or may comprise, according to some embodiments, an opioid narcotic (e.g., fentanyl, remifentanyl, sufentanil, morphine, hydromorphone, oxycodiene and salts thereof); a non-steroidal antinflamatory (NSAID) (e.g., diclofenac, naproxen, ibuprofin, and celecoxib); a local anesthetic (e.g., lidocaine, tetracaine, and bupivicaine); a dopamine antagonist (e.g., apomorphine, rotigotine, and ropinerole); drugs used for the treatment and/or prevention of allergies (e.g., an antihistamine, an antileukotriene, an anticholinergic, and an immunotherapeutic agent); an antispastic (e.g., tizanidine and baclofin); a vitamin (e.g., niacin); Selegiline; rasagiline; and any combination thereof. A biological material may be or may comprise a protein, a peptide, a nucleic acid (e.g., an oligonucleotide), a lipid, and/or a carbohydrate.

In some embodiments, a pump system may administer a combination of two or more APIs. For example, a pump system may be configured to include a single delivery fluid chamber filled with the combination. A pump system may be configured, for example, to include two or more delivery fluid chambers that feed into a common catheter/needle or separate catheters/needles. In some embodiments, a pump system may be configured to deliver two or more APIs at a fixed ratio and/or a variable ratio. A pump system may be configured to delivery each API subject to independent delivery modulation in some embodiments. For example, two or more drugs may be administered simultaneously and/or sequentially (e.g., overlapping).

A fluid delivery system may operate, in some embodiments, by indirect pumping. For example, a pump fluid (e.g., a solution containing little or no drug to be delivered, such as deionized water) may pass through a pump, whereas a delivery fluid does not, but instead is pushed by a pump fluid. In some embodiments, a separator may be a displaceable and/or deformable water insoluble solid, a water-immiscible liquid, and/or a water-immiscible gas (e.g., air) preventing the mixing of a pump fluid and a delivery fluid.

In some embodiments, control (e.g., strict control) of a dosage and dose-rate (i.e., delivered volume and flow rate) may be desired and/or required. In some embodiments, a flow rate may be controlled by a constant voltage supply. In some embodiments, a flow rate may be controlled by a constant pressure. In some embodiments, flow rate may be controlled by an applied current. In some embodiments, flow rate may be controlled by an applied voltage. In some embodiments, a flow rate may be continuous. In some embodiments, electrode mass and/or consumption of an anode and/or cathode may allow for 7 hours of continuous operation at a flow rate of 15 µL/min. In some embodiments, an average flow rate may be controlled by pulsing (e.g., periodic voltage and/or current pulsing). For example, flow rate may be controlled by pulsing over a period of about 4 days, about 3 days, about 2 days, about 1 day, about hourly, every about 50 minutes, every about 40 minutes, every about 30 minutes, every about 20 minutes, every about 10 minutes, every about 5 minutes, every about 2 minutes, every about 1 minute, every about 20 seconds. In some embodiments, an average flow rate of 0.13 µL/min may be obtained by applying 10 second pulses of 75 µA, every 15 minutes.

In some embodiments, an electroosmotic pump operates without an external power source. The current and voltage necessary to drive the flow are generated by the two electrodes at the two sides of the membrane. The two electrodes form a galvanic cell. Such could be the case, for example, when one electrode comprises silver, or copper, or zinc and the opposite electrode comprises $MnO_2$; or when one electrode comprises zinc and the opposite electrode comprises $Ag_2O$. Optionally, a resistor in the external electronic path between the two electrodes limits the current and thereby the flow rate. Also, the coulombic amount of the oxidizable metal on the anode limits the total charge to flow and thereby the total delivery amount.

In some embodiments, application of a current (or voltage) across electrodes of a pump may drive protons to the cathode, where they may be consumed by a cathodic reaction. Without being limited to any particular mechanism of action, protons may propagate rapidly at the polyanionic surface of a ceramic membrane dragging the proximal water sheet, which transfers momentum to the water-bulk causing its flow. In some embodiments, (e.g., where electroosmotic flow is driven by a fast proton flux at the surface of a sandwiched porous membrane and/or adsorption of an impurity on the membrane perturbs flux), it may be desirable to use pure protic liquids like water as a pump fluid.

In some embodiments, an electrososmotic flow is driven by a fast proton flux at the surface of a sandwiched porous membrane. In some embodiments, a delivery fluid is pushed by pumped water. In some embodiments, dilution of a delivery fluid solution by pumped water is avoided by a separator (i.e., an oil drop and/or a gas bubble) inserted between a water and delivery fluid. In some embodiments, to prevent a separator (e.g., oil drop) from reaching the subcutaneous tissue, the volume of a pump fluid (or pump fluid+pump chamber separator) may be less (e.g., about 0.5 mL less, about 0.2 mL less, and/or about 0.1 mL less) than that of delivery fluid (or delivery fluid+delivery chamber separator). In some embodiments, delivery fluid (e.g., water) in a delivery fluid chamber may become exhausted and separator (e.g., oil) may enter a pump, whereupon flow may be reduced and/or stopped. At that time, some delivery fluid may remain in a delivery fluid chamber. It may be desirable, in some embodiments, for the volume of delivery fluid remaining to be as small as possible or as small as possible without compromising safety.

In some embodiments, a separator may comprise a gas, a liquid and/or a solid. A gaseous separator, in some embodiments, may comprise an air bubble. In some embodiments, an example of a useful liquid separator may be a silicone oil or a glycerol mono or di-ester of a fatty acid. In some embodiments, solid separators may be plastic, ceramic or metallic. In some embodiments, a separator moves along a defined path when pushed by a pumped solution. In some embodiments, a solid separator may optionally also serve in stopping the flow when the delivery fluid is nearly or completely exhausted, for example, by plugging an orifice through which the delivery fluid enters the tubing connected to the body-inserted cannula. In some embodiments, for example, the downstream side of the plug can be conical, the tip of the cone penetrating the cannula or its upstream extension when the delivery fluid is exhausted. In some embodiments, combined volumes of a pumped solution and a delivery fluid may be minimized by making their volumes about similar, with the volume of a delivery fluid exceeding the volume of a pumped solution, so as to avoid delivery of only a pumped solution to the cannula.

FIGS. 10A-10C illustrate pump system 1000 in operation in which pump fluid chamber 1060 and delivery fluid chamber 1080 have been rendered, for illustration purposes, as coplanar with each other and with pump 1010 similar to the collinear arrangement shown in FIGS. 6A, 7A-7C, and 8A-8E. Pump fluid chamber 1060 and delivery fluid chamber 1080 may be configured as illustrated or may be configured such that pump fluid chamber 1060 substantially overlays delivery fluid chamber 1080 and the two together define, at least partially, an oval and/or a circle (e.g., as shown in FIGS. 4B-4D).

FIG. 10A illustrates a sectional view of pump system 1000 in which the chambers 1060 and 1080 are loaded and ready for use according to a specific example embodiment of the disclosure. FIG. 10B illustrates a sectional view of a pump system shown in FIG. 10A during operation according to a specific example embodiment of the disclosure. Upon application of a potential difference or current across pump 1010, pump fluid 1056a begins to flow through pump 1010 into delivery fluid chamber 1080. Separator 1057a moves in tandem with the distal edge of pump fluid 1056a and air is drawn into chamber 1060 through inlet 1078. As pump fluid 1056a moves to and accumulates in chamber 1080, the combined volume of 1056a and 1056b forces separator 1057b to move distally toward outlet 1099, which in turn, expresses delivery fluid 1058 through outlet 1099. FIG. 10C illustrates a sectional view of pump system 1000 near completion of operation according to a specific example embodiment of the disclosure. Flow may be slowed and/or stopped by reducing the potential difference and/or current applied to pump 1010 (e.g., to about zero). In FIG. 10C, flow is stopped with some delivery fluid still remaining in chamber 1080 and before an opportunity has arise for separator 1057b to be expressed through outlet 1099.

Pumping and/or delivery may be achieved in some embodiments by electrooxidizing at the anode of the electro-osmotic pump a water-soluble organic compound that passes through a pump. According to some embodiments, the concentration of a water-soluble organic compound is sufficient to reduce (e.g., undesirably reduce) pumping efficiency, necessitating application of higher voltages and/or currents. In some embodiments, protons are released in an electrooxidation reaction. Some examples of electrooxidized compounds include p-hydroquinone; catechol; salicylic acid; acetyl salicylic acid (Aspirin); cysteine; reduced glutathione; N-acetyl-p-aminophenol (Tylenol™) and ascorbic acid (Vitamin C) or its salt or salts. Some compounds may be characterized by being electrooxidized on a platinum electrode in a rapidly stirred solution at about a 0.1 M concentration at a current density of at least about 1 mA $cm^{-2}$ when the platinum electrode is poised at a potential of less than about 1 V, for example, less than about 0.5 V, and for example, about 0.3 V versus the potential of the Ag/AgCl (3 M KCl) reference electrode. In some embodiments, a proton releasing electrooxidized compounds may be generally non-toxic, and for example, include compounds that are safely ingested. For example, some embodiments may include ascorbic acid (Vitamin C) as an electrooxidized compound. In some embodiments, the pH of a pumped, organic compound containing, solution may be between about pH 1 and about pH 8, for example between about pH 2 and about pH 5, and for example between about pH 2 and about pH 4. An example of a solution is a solution of ascorbic acid of a concentration between about 5 mM and about 200 mM, or for example, between about 20 mM and about 100 mM, and for example, about 50 mM.

The flow rate of a 50 mM ascorbic acid containing solution, sustained with the electro-osmotic pump NFT (RP5A-RL-N610 made by NanoFusion Technology) is about 8 μL/min when pump is powered by a 1.4 V DCV alkaline zinc-manganese dioxide coin battery. In some embodiments, a cathode and an anode of an electro-osmotic pump may be made of non-corroding porous conductors through which a pumped solution flows. In some embodiments, the true area of an electrode may exceed (e.g., at least about tenfold) its footprint, i.e., its geometrical area. This pump may evolve hydrogen at its cathode.

In some embodiments, an electro-osmotic pump may comprise (i) one or more phosphorus-containing membranes (e.g., a phosphosilicic acid on silica membrane) and/or boron-containing membranes (e.g., a borosilicic acid on silica membrane), (ii) a non-gassing (e.g., absence of gas bubbles visible to the naked eye), electrooxidizable and proton-generating porous anode constituent (e.g., silver), and/or (iii) a non-gassing, hydroxide anion generating or proton-consuming cathode constituent (e.g., silver oxide). When operated at low voltages, where no gas evolution causing electrolysis takes place, a pump may provide, in some embodiments, sufficient flow rates for the delivery of drugs (e.g., prandial insulin) and/or pumping cooling fluids, for example, to cool electronic and/or optical devices. According to some embodiments, a low voltage is a voltage of less than about 3 V, for example less than 2.0 V, less than 1.5 V, less than 1.0 V, less than 0.8 V, less than 0.6 V, about 0.5 V or less.

According to some embodiments, a DC electro-osmotic pump may operate at a voltage of less than about 3 V (e.g., less than 1.23 V which is the thermodynamic voltage for the electrolysis of water) at about 25° C. For example, a pump may operate at about 0.5 V and drive about $1.3 \times 10^4$ water molecules per faradaically reacting proton and/or silver cation. The flow rate per $W\text{-}cm^2$ is 290 nth $min^{-1}$, the highest reported to the knowledge of applicants and a record 4.8 mL of water are pumped per joule. An anode of a pump may comprise, for example, a porous, readily electro-oxidizable metal, such as silver, copper or lead, or an electrooxidizable metal oxide, such as manganese oxide, particularly MnO (OH). A cathode of a pump may comprise, for example, an electroreducible metal oxide, such as silver oxide, particularly $Ag_2O$, a copper oxide, a lead oxide, particularly $PbO_2$, or a manganese oxide, particularly $MnO_2$. A pump may comprise, for example, a porous, phosphorus containing membrane, for example a membrane made of phosphosilicic acid coated, fused silica microspheres. Flow of deionized water may start at about 0.1 V and may increase about linearly with the applied current. In some embodiments, flow rate of deionized water for a pump having an about 0.3 $cm^2$ cross sectional area and built with a $Ag/Ag_2O$ anode, a $Ag/Ag_2O$ cathode, and a membrane made by fusing about 1 μm diameter phosphosilicic acid coated, fused silica microspheres, operating at about 24° C., at about 0.1 mA and at about 0.5 V may be about 14.5±1.5 μL $min^{-1}$. This flow rate may be sufficient, for example, for prandial insulin administration (e.g., bolus delivery).

FIG. 2 is a schematic depicting an electro-osmotic pump, its electrode reactions, and the transport processes, in accordance with certain exemplary embodiments: As depicted in FIG. 2, pump 210 may be formed as a sandwich of a ceramic membrane 220 (e.g., porous phosphosilicic acid on silica) between two electrodes (e.g., porous Ag/Ag$_2$O electrodes) 230 and 240. The pumped fluid may be water (e.g., de-ionized H$_2$O). At Ag/Ag$_2$O anode 230, silver (Ag) may be electrooxidized to silver oxide (Ag$_2$O) and a proton (H+) and/or silver cation (Ag+) flux may be generated without water being electrooxidized to O$_2$. Protons and/or silver cations may flow through membrane 220 to Ag/Ag$_2$O cathode 240 where Ag$_2$O may be electroreduced to Ag, without water being electroreduced to H$_2$. Accordingly, protons and/or silver cations may be consumed by combining with co-generated hydroxide anions.

In some embodiments, electrodes may be rotated (i.e., the anode becomes the cathode and vice versa) and/or charged to make the pump re-usable. In some embodiments, electrodes may be rotated electrochemically by reversing the current, so that the silver formed in the operating pump from silver oxide may be electro-oxidized upon re-charging the pump to silver oxide, and the silver oxide formed in the operating pump from silver is electro-reduced upon re-charging the pump to silver.

In some embodiments, an electroosmotic pump may operate without an external power source. The current and voltage necessary to drive the flow may be generated by two electrodes at the two sides of the membrane. The two electrodes may form, for example, when one electrode comprises silver, or copper, or zinc and the opposite electrode comprises MnO$_2$; or when one electrode comprises zinc and the opposite electrode comprises Ag$_2$O. In some embodiments, a resistor in the external electronic path between the two electrodes may limit the current and thereby the flow rate. In some embodiments, the coulombic amount of an oxidizable metal on an anode may limit the total charge to flow and thereby the total delivery amount.

To control their blood sugar levels, Type 1 diabetic people need about 0.8 insulin units/kg/day. There are about 27 units in 1 mg of insulin, and fast acting insulin solutions contain typically about 100 units/mL. The dosings and timings of insulin vary from patient to patient. In the management of Type 1 diabetes, in some patients, about ¼ of the insulin, i.e., about 0.2 insulin units/kg/day, are continuously administered, and about 0.2 insulin units/kg are administered with each of the three daily meals. In the case of a person weighing 80 kg, about 16 units, i.e., about 160 μL of fast acting insulin are delivered with a meal. For a 20 minute delivery the required pumping rate is about 8 μL/min.

Allergen Diagnostics

According to the website of the NIH-National Institute of Allergic Diseases, allergies are the sixth leading cause of chronic disease in the United States. Their 2005 cost to the healthcare system was about $18 billion. About half of all Americans test positive for at least 1 of the 10 most common allergens: Ragweed, bermuda grass, rye grass, white oak, Russian thistle, alternaria mold, cat, house dust mite, German cockroach, peanut. Food allergy occurs in 6-8% of children younger than 6 and in 2% of adults. Common food allergens include: Cow's milk; eggs; shellfish; nuts. In 2005, 30 million people living in the United States had asthma, resulting in >480,000 hospitalizations and about 4,200 deaths.

Figure 11:
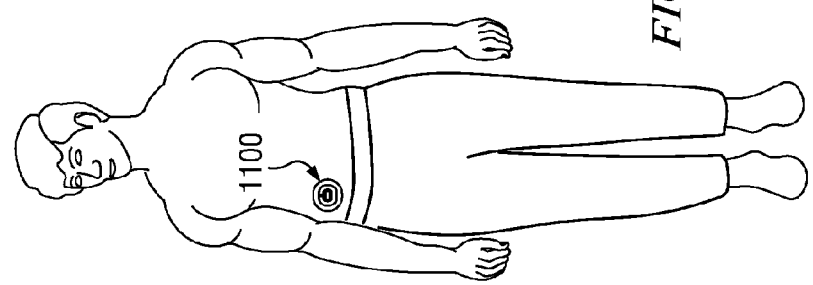
FIG. 11 illustrates a subject wearing a pump system according to a specific example embodiment of the disclosure.

According to some embodiments, a fluid delivery system (e.g., electroosmotic pumps) may also be used (e.g., advantageously used) in immunotherapy of allergies. According to present practice, a series of increasingly concentrated suspensions or solutions of the allergen or allergens to which the patient is sensitive are subcutaneously injected. The suspensions are administered over an extended period of time, typically several years. The injections are believed to reduce the level of IgE antibodies in the blood and to cause the body to make protective IgG antibodies. In present practice the patient needs to visit the office of the allergist, wait to be injected by a nurse or other health professional, then wait at least about 20 min to assure the absence of a severe allergic reaction to the administered dose. The dosing is usually suboptimal, because the allergist wishes to be reasonably certain that there will not be a severe allergic reaction. Gradual delivery of the suspension or solution over a period longer than about 5 minutes (e.g., longer than about 10 min, longer than about 30 min, longer than about 1 hour, longer than about 3 hours, and/or longer than about 6 hours) would allow a subject to remove a skin-adhered system containing an electroosmotic or other drug pump if he or she observes excessive reddening or swelling indicative of the start of an unwanted excessive allergic reaction. Such an allergy immunotheraphy system may have, other than the pump itself, two small compartments, of similar or different volumes. Each compartment may, independently, have a volume of, for example, less than about 2 mL, less than about 1 mL, less than about 0.5 mL, and/or less than about 0.2 mL. One compartment may contain a pumped solution, (e.g., de-ionized water or water containing less than about $10^{-2}$ moles per liter of a solute) and/or a second compartment may contain a suspension or solution of one or more allergens. The two compartments may be separated by a moving separator, which may be moved by a pumped solution (e.g., de-ionized water), and push an allergen-containing suspension. A system may also comprise means to attach it to the skin, such as a non-allergic two sided adhesive tape used by wearers of wigs and hairpieces, and a short hollow needle, which may be, for example, longer than about 0.1 cm and shorter than about 0.6 cm and/or longer than about 0.3 cm and shorter than about 0.5 cm. FIG. 11 illustrates a subject wearing a pump system an according to a specific example embodiment of the disclosure. A needle may be narrow (e.g., between about 24 and about 33 gauge and/or between about 26 gauge and about 30 gauge). A needle may be connected directly to the drug reservoir or it may be connected to the drug reservoir through tubing, for example plastic tubing. A pump may also be used to administer one or more vaccines.

Allergists now use skin tests to determine whether a person has IgE antibodies in the skin that react to a specific allergen. In these skin tests they inject subcutaneously, or apply to a scratch, series of about constant volumes of extracts of decreasingly diluted allergens, such as dust mites, pollens, or molds found in the area in which the patient lives or works. In a positive reaction, a small, raised, reddened wheal, with a surrounding flare, appears at the test site. The inverse of the dilution of the injected allergen extract, its volume and size of the wheal allow the allergist to gauge the relative sensitivity of a person to different allergens.

According to some embodiments of the disclosure, the tested allergen containing suspension or solution may be subcutaneously administered by pumping, for example by a system comprising the disclosed electroosmotic pump. It may be administered, for example, at a fixed flow rate (e.g., between about 0.1 μL min$^{-1}$ and about 10 μL min$^{-1}$ and/or between about 0.5 μL min$^{-1}$ and about 0.5 μL min$^{-1}$) until the positive reaction indicative flare or wheal or combination of flare and wheal is observed, when the flow would be stopped. The inverse elapsed timed between the start of the flow and the stopping of the flow would indicate the sensitivity to the tested allergen. Alternatively, the flow rate would be increased during the test, for example in 0.1 μL min$^{-1}$ increments, until the flare or wheal or combination of flare and wheal is observed and the flow is stopped, for example, by removing the system. The inverse number of increments between the starting of the flow and its stopping would indicate the sensitivity to the tested allergen. Alternatively, small boluses may be intermittently administered. Boluses may be of constant or increasing volume. In some embodiments, they would be larger than about 100 mL and smaller than about 10 µL. They may be delivered about every 2 minutes or less, for example every minute or less, for example every 30 s or less, for example every 10 s or less.

In a diagnostic system, the combined volumes of an allergen suspension or solution, a pumped aqueous solution and a pump itself may total, according to some embodiments, less than about 5 mL, less than about 2 mL, less than about 1 mL, and/or less than about 0.5 mL. In some embodiments, a system may have a generally circular and/or annular shape with a diameter of, for example, less than about 2 cm, less than about 1 cm, less than about 6 mm, less than about 4 mm. According to some embodiments, an electro-osmotic pump system may be skin-attached, optionally off the site of the administration of the tested allergen, so as not to block the view of the expected wheal and flare. A system may be worn, in some embodiments, for a period longer than about 2 min, longer than about 5 min, longer than about 10 min, longer than about 30 min, and/or until a positive reaction indicative flare is observed. Flow may then be stopped and the system would be optionally removed from the skin. Optionally, the flow would be automatically stopped and the elapsed time or number of boluses measured when the flare or the wheal develop. For such automatic monitoring or control of flow, a system may also comprise a detector or multiple detectors, for example of reflected light or of temperature. Development of the flare may be tracked for example by reflectometry or thermometry. For example, the ratio of the reflected light of wavelengths between about 600 and about 900 nm to that reflected between about 400 nm and about 900 nm may be monitored to track the reddening. Alternatively, the decrease in the reflected flux of white or yellow light may be monitored; or the temperature difference between the core of the flare and a nearby skin site but off the flare may be monitored.

A diagnostic system may have, other than the pump itself, two small compartments, of similar or different volumes. Each compartment may, independently, have a volume of, for example, less than about 2 mL, less than about 1 mL, less than about 0.5 mL, and/or less than about 0.2 mL. A system may also comprise a hollow needle, which may be, for example, longer than about 2 mm and shorter than about 1 cm and/or longer than about 3 mm and shorter than about 6 mm. A needle may be narrow (e.g., between about 24 and about 33 gauge and/or between about 26 gauge and about 30 gauge). A needle may be connected, for example through plastic tubing, to an allergen suspension or solution containing reservoir. Tubing, part of which may be taped to the skin, may be long enough to permit subcutaneous delivery of the allergen suspension or solution at a site not covered by a reservoir and pump comprising system. In some embodiments, tubing may be longer than about 1 cm, longer than about 3 cm, and/or longer than about 5 cm. A needle may be inserted below the skin at an off-vertical angle for shallow penetration and delivery of the allergen optionally in the outer part of the dermis that is proximal to the epidermis. For example, a needle may be inserted at an angle (versus vertical) of at least about 50°, at least about 60°, at least about 70°, and/or at least about 80°.

In some embodiments, a system may also comprise a factory or health care professional programmed electronic system controlling the flow rate and monitoring the delivered dose of the allergen. This system may be optionally incorporated, as shown for example in FIG. 6C, in the skin attached package. Unlike a drug reservoir, pumped aqueous solution reservoir and/or an electro-osmotic pump of a system, which may be discarded after use, an electronic control and display system may be separable, removable, and/or reusable. An electronic control and display system may be electrically connected to an electroosmotic pump through contact pads, which both the re-used electronic control unit and the pump may have. Optionally, for safety, an electronic part of a system would provide a periodic alarm, alerting a patient or health care professional to check the inflammatory response such as the wheal or flare. It may discontinue flow of allergen solution or suspension unless a patient or health care confirms that the inspection did not show as yet sufficient inflammatory response. The periods between the alerts may be fixed and/or user-selectable. For example, the period between alerts may be less than about 20 min, less than about 10 min, less than about 5 min, and/or less than about 2 min.

Immunotherapy, typically involving weekly or twice-weekly subcutaneous allergen injections for three years, provides relief after 1 year to 85% of the patients. Inexpensive drug pumps in general and particularly single-use electroosmotic pumps may be advantageously used in the immunotherapy of allergies. According to the present practice of immunotherapy, a series of increasingly concentrated suspensions or solutions of the allergen or allergens to which the patient is sensitive is subcutaneously injected. The solutions or suspensions are administered over an extended period of time, typically several years. The injections are believed to reduce the level of IgE antibodies in the blood and to cause the body to make protective IgG antibodies. According to the present practice, the patient needs to visit the office of the allergist, wait to be injected by a nurse or other health professional, then wait at least about 20 min to assure the absence of a severe allergic reaction to the administered dose. The dosing is usually sub-optimal, because the allergist wishes to be reasonably certain that there will not be a severe allergic reaction. Delivery of the allergen suspension or solution over a period longer than about 5 min, for example longer than about 10 min, for example longer than about 30 min, for example longer than about 1 hour, for example longer than about 3 hours, for example longer than 6 hours would allow the patient to remove the skin-adhered system containing the electro-osmotic or other drug pump when he or she observes excessive response, such as excessive reddening or swelling.

An immunotherapy system of this disclosure is designed to deliver an about optimal and always safe dose of the allergen or allergens. Some, but not all components and functions may be similar to those of the diagnostic system. Because the delivery of the therapeutic doses may be generally in the dermis or in the tissue below the dermis, such as adipose tissue or connective tissue or muscle, the needle may be inserted about vertically to the skin, for example at an angle of at least about 60° versus the plane of the skin, for example at least about 70° versus the plane of the skin, for example at least about 80° versus the plane of the skin. The solution or suspension of the allergen or allergens may be administered for example until a sufficient but not excessive local inflammatory response is observed, exemplified by the appearance of a red, about circular, region, of a diameter typically greater than about 2 mm and less than about 2 cm, typically greater than about 4 mm and less than about 1 cm, or by local swelling, or by local itching. Flow rate may be adjusted such that the inflammatory response may be projected to appear more than about 5 min after the start of the flow, for example more than about 10 min, for example more than about 20 min, for example more than about 30 min, for example more than about 1 hour, for example more than about 2 hours, for example more than about 3 hours, for example more than about 6 hours. When the inflammatory response is observed, the delivery of the allergen comprising solution or suspension may be discontinued and the system may be removed from the skin.

A hollow needle 506 may be placed, as shown in FIG. 6C, below the skin attached system and covered by it. In some embodiments, a hollow needle may be placed in a region other than where the package is adhered to the skin, for example, to allow visual inspection for the appearance of a flare or wheal or for visual confirmation that the needle is properly implanted. A system may also comprise a hollow needle, which may be, for example, longer than about 2 mm and shorter than about 1 cm and/or longer than about 3 mm and shorter than about 5 mm. A needle may be narrow (e.g., between about 24 and about 33 gauge and/or between about 26 gauge and about 30 gauge). It may be connected to the allergen containing reservoir for example by a sufficiently long plastic tubing to allow easy observation of the evolution of the inflammatory response at the delivery site. An immunotherapy system may have, other than the pump itself, two compartments, of similar or different volumes. Each compartment may, independently, have a volume of, for example, less than about 2 mL, less than about 1 mL, less than about 0.5 mL, and/or less than about 0.2 mL.

A system may also comprise a factory or health care professional programmed electronic system controlling the flow rate and monitoring the delivered dose of the allergen. This system may be optionally incorporated, as shown for example in FIG. 6C, in the skin attached package. Unlike the drug reservoir, pumped aqueous solution reservoir and electroosmotic pump part of the system, which would be typically discarded after use, the electronic control and display system would be removable and reusable. It may be connected to the pump through contact pads, which both the re-used electronic control unit and the typically disposable solution and pump containing part would have. Optionally, for safety, the electronic part of the system may provide a periodic alarm, telling the patient or health care professional to inspect the extent of the wheal or flare. It may discontinue delivery of the allergen solution or suspension unless the patient or health care confirms the inspection. The periods between the alarms may be typically of about less than 20 min, for example less than 10 min, for example less than 5 min, for example less than 2 min.

As will be understood by those skilled in the art who have the benefit of the instant disclosure, other equivalent or alternative compositions, devices, methods, and systems for pumping a fluid (e.g., an active pharmaceutical ingredient, an allergen, a nutrient, a diagnostic agent) can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, the position and number of a pump, cathode, anode electrodes, tubing, PVC frames, PVC rings, reservoir, reservoir chambers, hairpins, curvatures, controller, air gaps, drug inlets, drug outlets, oil gaps, controller, processor, memory, power source, display, user interface, needle, adhesive, elastic band, and/or wires may be varied. In some embodiments, pump, cathode, anode electrodes, tubing, PVC frames, PVC rings, reservoir, reservoir chambers, hairpins, curvatures, controller, air gaps, drug inlets, drug outlets, oil gaps, controller, processor, memory, power source, display, user interface, needle, adhesive, elastic band, and/or wires may be interchangeable. In addition, the size of a device and/or system may be scaled up (e.g., to be used for adult subjects) or down (e.g., to be used for juvenile subjects) to suit the needs and/or desires of a practitioner. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated.

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each FIGURE disclosed (e.g., in one or more of the examples, tables, and/or drawings) may form the basis of a range (e.g., depicted value +/− about 10%, depicted value +/− about 50%, depicted value +/− about 100%) and/or a range endpoint. With respect to the former, a value of 50 depicted in an example, table, and/or drawing may form the basis of a range of, for example, about 45 to about 55, about 25 to about 100, and/or about 0 to about 100. Persons skilled in the art may make various changes in methods of preparing and using a composition, device, and/or system of the disclosure. For example, a composition, device, and/or system may be prepared and or used as appropriate for animal and/or human use (e.g., with regard to sanitary, infectivity, safety, toxicity, biometric, and other considerations).

All or a portion of a device and/or system for electroosmotic pumping may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the following claims.

EXAMPLES

Some specific example embodiments of the disclosure may be illustrated by one or more of the examples provided herein.

Example 1

Working Prototype with Platinum and Polyaniline Electrodes

In some anodic electrooxidation reactions, where dehydroascorbic acid and two protons are generated, an optional cathodic reaction, two protons are electroreduced to $H_2$. At the 2.7 pH of the ascorbic acid solution, dehydroascorbic acid, with a $pK_a$ of about 4, is not ionized, and readily permeates through the polyanionic fused silica or other cation exchange membrane.

When $H_2$ micro-bubbles are formed, these are formed only downstream of the membrane, and are not trapped by the membrane. Thus, they usually do not affect the pumping rate. A flow rate of about 7.6 µL/min is sustained already at about 1.4 V from an alkaline Zn-anode battery. As seen in Table 2, a flow rate of about 10.6±0.5 has been reproduced on the dates and times indicated, with a pump powered by a 1.6 V zinc-silver oxide battery.

TABLE 2

Day to Day Reproducibility of the Flow (in μL/min) at a Constant Applied Voltage

| $4^{th}$ 1810 | $5^{th}$ 0945 | $5^{th}$ 1020 | $5^{th}$ 1055 | $5^{th}$ 1130 | $5^{th}$ 1905 | $6^{th}$ 0910 | $6^{th}$ 1225 | $6^{th}$ 1615 | $9^{th}$ am | $9^{th}$ am | $9^{th}$ am | $9^{th}$ am | $9^{th}$ am | $9^{th}$ am | $9^{th}$ am | $9^{th}$ am |
|---|---|---|---|---|---|---|---|---|---|---|---|---|---|---|---|---|
| 10.9 | 11.1 | 10.8 | 10.9 | 10.5 | 10.5 | 10.4 | 11.0 | 10.7 | 9.8 | 11.8 | 10.9 | 10.3 | 9.8 | 10.8 | 10.1 | 9.9 |

Dosing may be monitored and/or controlled coulometrically. In some electro-osmotic pumps the flow rate scales in a predictable way, for example about linearly, with the current. If a constant current is maintained, then the pumped solution volume scales linearly with time and/or with the passed charge. In certain embodiments, the pumped volume scales about linearly with the passed charge also when the current varies, for example because of variation of the operating voltage or the temperature. This is seen in Tables 3 and 4 below. In the experimental results shown in Table 4, the pumped solution contained about 50 mM ascorbic acid and the pump operated at about 23° C. Irrespective of the variations in voltage or in the current, the ratio of the pumped volume to charge was about constant at about 0.410±0.008 μL/mC for this particular pump and pumped solution. In Table 4, it can be seen that the current and the flow rate increase by about 2% per ° C. when the other operating parameters are held constant. Nevertheless, the pumped solution to passed charge ratio is about constant at about 0.344±0.008 μL/mC across the about 20° C. temperature range between about 20° C. and about 40° C.

TABLE 3

Substantial Independence of the Pumped Volume/Charge Ratio of Voltage, Current and Flow Rate (50 mM Ascorbic Acid, 23° C.)

| | | Volume (μL/ 20 min) | Charge (mC) | Volume/Charge (μL/mC) | Avg. Flow Rate (μL/min) | Avg. current (μA) |
|---|---|---|---|---|---|---|
| 1.4 V | Test 1 | 15 | 36.24 | 0.414 | 7.6 | 302 |
| | Test 2 | 15.25 | 36.3 | 0.42 | | |
| | Test 3 | 15.15 | 36.36 | 0.417 | | |
| 1.5 V | Test 1 | 17 | 41.37 | 0.411 | 8.6 | 343 |
| | Test 2 | 17 | 41.44 | 0.41 | | |
| | Test 3 | 17.3 | 41.24 | 0.419 | | |
| 1.6 V | Test 1 | 19.5 | 46.19 | 0.422 | 9.5 | 383 |
| | Test 2 | 18.55 | 46.11 | 0.402 | | |
| | Test 3 | 18.5 | 45.97 | 0.402 | | |
| 1.7 V | Test 1 | 20.5 | 51.06 | 0.401 | 10.3 | 426 |
| | Test 2 | 20.6 | 51.14 | 0.403 | | |
| | Test 3 | 20.5 | 51.14 | 0.401 | | |

TABLE 4

Substantial Independence of the Pumped Volume/Charge Ratio of Temperature and Flow Rate (50 mM Ascorbic Acid; Applied Voltage 1.6 V)

| Temp. | | Test 1 | Test 2 | Test 3 | Avg. Flow Rate, μL/min |
|---|---|---|---|---|---|
| 20° C. | Volume in 10 min, μL | 65 | 62.5 | 62.5 | 6.3 |
| | Charge, mC | 187.4 | 183.3 | 183 | |
| | Volume/Charge, μL/mC | 0.347 | 0.341 | 0.342 | |
| 30° C. | Volume/10 min, μL | 83 | 77.5 | 75 | 7.9 |
| | Charge, mC | 231.4 | 229.2 | 228.5 | |
| | Volume/Charge, μL/mC | 0.359 | 0.338 | 0.328 | |
| 40° C. | Volume/10 min, μL | 95 | 97 | | 9.6 |
| | Charge, mC | 272.2 | 278.9 | | |
| | Volume/Charge, μL/mC | 0.349 | 0.348 | | |

In some embodiments, the dose of the drug, e.g. insulin, may be coulometrically controlled by setting the charge to be delivered and may be monitored by determining the charge passed.

FIG. 9B illustrates an electro-osmotic pump assembly (without cannula) in certain embodiments. As shown in FIG. 9B, the simple and low-cost electro-osmotic pump has two lead wires connecting the battery. In some embodiments, the OD may be about 6 cm. When the red and black terminals are connected to a 1.6 V zinc-silver oxide battery, the flow rate at ambient temperature is about 6 μL/min. When connected to a 3.0 V lithium anode coin cell the flow rate is about 30 μL/min. The drug compartment contains about 3 mL of the drug solution. The volume of the pumped solution is slightly less than about 3 mL of about 0.4% insulin.

Figure 12A:
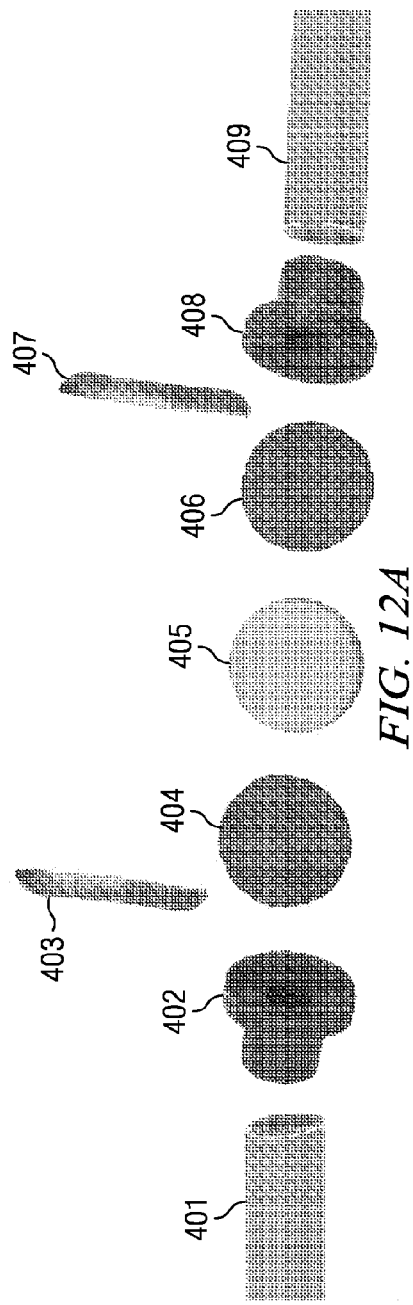
FIG. 12A illustrates a exploded view of a pump according to a specific example embodiment of the disclosure.
Figure 12B:
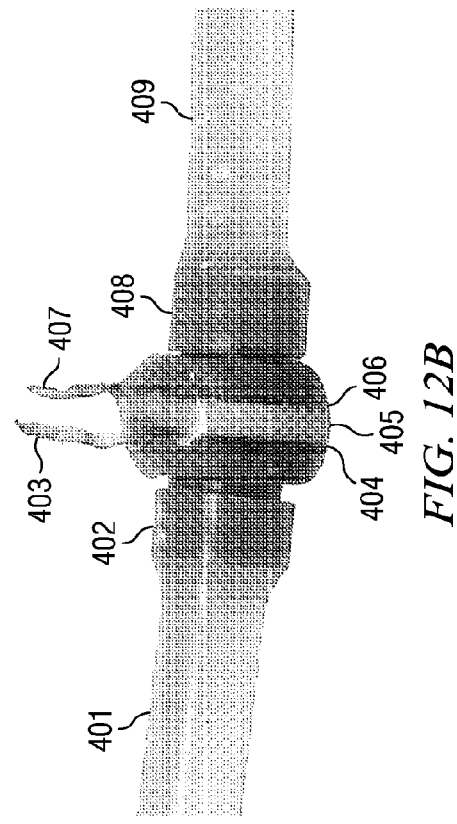
FIG. 12B illustrates the pump shown in FIG. 12A assembled according to a specific example embodiment of the disclosure.

FIG. 12A illustrates a exploded view of a pump shown in FIG. 12B according to a specific example embodiment of the disclosure. FIG. 12B illustrates the pump shown in FIG. 12A assembled according to a specific example embodiment of the disclosure, the about 8 mm OD pump is made of a membrane, 2 electrodes and a polyvinyl chloride frame. The OD of the active membrane is about 6 mm. The components, shown separately in FIG. 12A and assembled in FIG. 12B are silicone tubing 1235; polyvinyl chloride frame 1234; gold foil electrode for contacting 1233; platinum and polyanilines activated carbon cloth electrode 1230; ceramic membrane 1220; platinum and polyanilines activated carbon cloth electrode 1240; gold foil electrode for contacting 1243; polyvinyl chloride frame 1244; and silicone tubing 1245.

Figure 15:
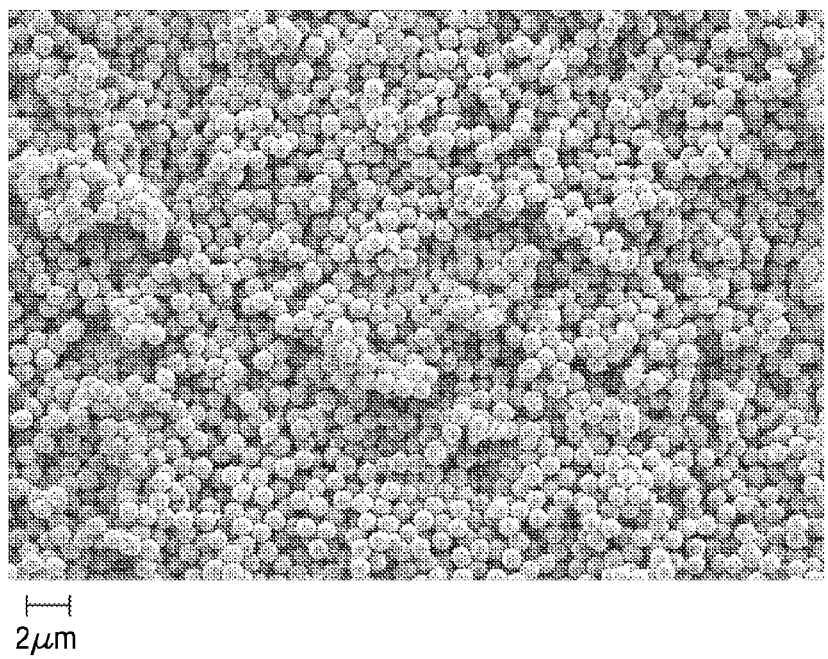
FIG. 15 is a scanning electron micrograph that illustrates a pump membrane according to a specific example embodiment of the disclosure.

The ceramic membrane 1220 was formed in a mold of about 1 μm OD silica monodisperse microspheres (Polysciences, Warrington, Pa., catalog number 24325-15) or of about 1 to 5 μm silica microparticles (Aldrich S5631) with about 80% of the about spherical particles being in the 1 to 5 μm range. About 5 mL of the about 10 weight % silica-containing aqueous solution was mixed with about 5 μL of 85% phosphoric acid and dried at about 65° C. overnight. Then about 65 mg of the dried silica was poured into an about 8 mm ID stainless steel mold, cold-pressed to form a pellet, which was fired for about 4 hours at about 700.° C. The preparation of the membranes was completed by their immersion for about 1 hour in boiling de-ionized water. The thickness of the resulting 8 mm OD membrane-pellets was about 1.3 mm when the about 1 µm silica monodisperse microspheres were used. A cross-sectional scanning electron micrograph of the membrane is shown in FIG. 15.

The electrodes 1230 and 1240 of FIG. 12A were formed by coating platinum on Toray carbon paper (TGP-H-090) which is about 280 µm thick. The pore fraction in of the membrane is about 78%. The surface was cleaned by exposure to an about 20 torr oxygen plasma for about 1 hour. A polyaniline film was formed on the plasma-cleaned carbon paper by immersing it in a solution of about 0.1 M aniline in about 0.5 M HCl and cycling the potential 4 times between about 0.0 V and about 0.815 V versus Ag/AgCl at a rate of about 50 mV/s. Then the electrode was rinsed with de-ionized water and immersed in about 5 mM $K_2PtCl_6$ in about 1.0 M $H_2SO_4$ and sweeping the applied potential ten times between about 0.5 V versus Ag/AgCl and about –0.2 V versus Ag/AgCl at a rate of 5 mV/s for 10. The Pt particles are deposited about uniformly with some aggregation and the average size of the deposited Pt particles was about 100-200 nm as seen in the scanning electron micrograph below. The resulting electrode catalyzed the electrooxidation of ascorbic acid and the evolution of $H_2$. A cyclic voltammograms at a scan rate of 20 mV/sec showed ascorbic acid electrooxidation and hydrated proton electroreduction to $H_2$ using 12.5 mm×22.5 mm Toray carbon paper electrodes, activated by plasma cleaning and platinum and 50 mM ascorbic acid. Prior to its incorporation in the pump, the electrocatalyst coated carbon paper was cut into 8 mm OD discs.

Figure 13B:
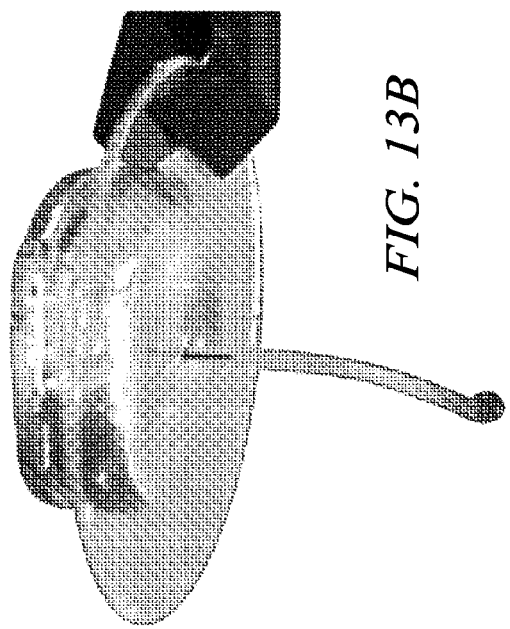
FIG. 13B illustrates a generally isometric view of the pump system shown in FIG. 13A in operation such that fluid has begun to move through drug outlet according to a specific example embodiment of the disclosure.
Figure 13D:
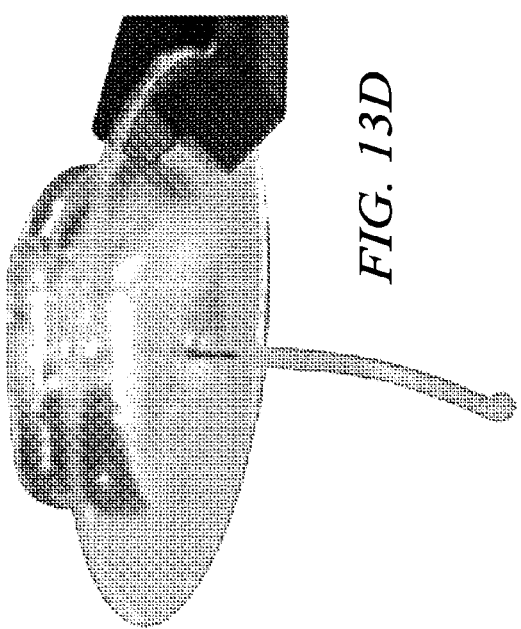
FIG. 13D illustrates a generally isometric view of the pump system shown in FIGS. 13A-13C in which fluid movement through drug outlet has been stopped according to a specific example embodiment of the disclosure.
Figure 13A:
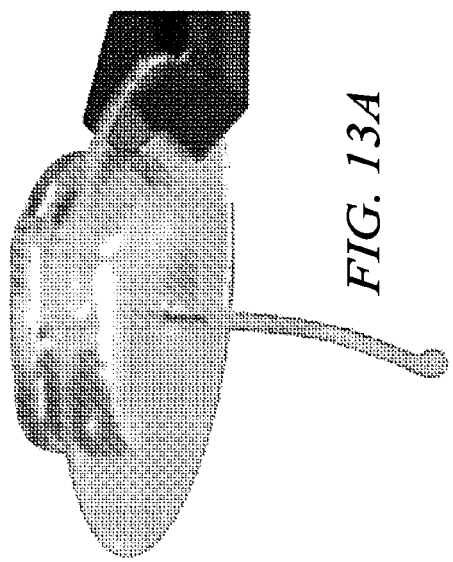
FIG. 13A illustrates a generally isometric view of a pump system according to a specific example embodiment of the disclosure.
Figure 13C:
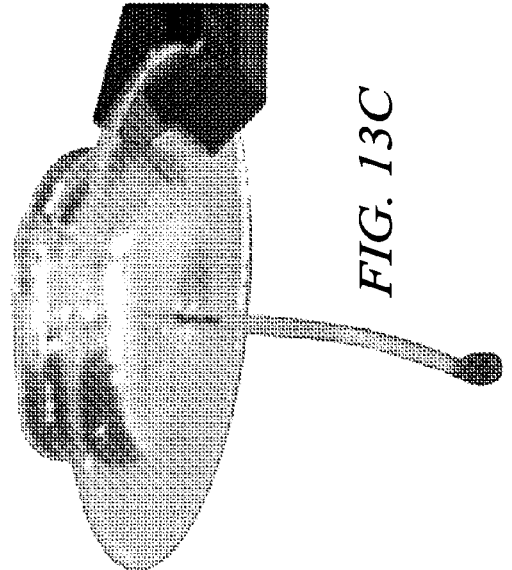
FIG. 13C illustrates a generally isometric view of the pump system shown in FIGS. 13A-13B in which fluid continues to move through drug outlet according to a specific example embodiment of the disclosure.

The membrane and electrodes were installed in a reservoir having a two-compartment configuration as shown in FIG. 4A to form a pump system as shown in FIG. 6B. Referring to FIG. 13A, the pumped ascorbic acid solution is colorless and a drug mimic dyes the solution red. FIGS. 13A-13D illustrate a pumping sequence of a drug pump in one embodiment of the present disclosure. Referring to FIGS. 13A-13D, the pump is powered by a 1.6V zinc-silver oxide battery. The flow rate is about 5 pt/min FIG. 13A illustrates four stages in the release of a drop of the red drug-mimic solution: at about 1 minute, FIG. 13B; at about 18 minutes, FIG. 13C; at about 23 minutes, and FIG. 13D at about 24 minutes after connecting the pump to a 1.6V battery.

Figure 14:
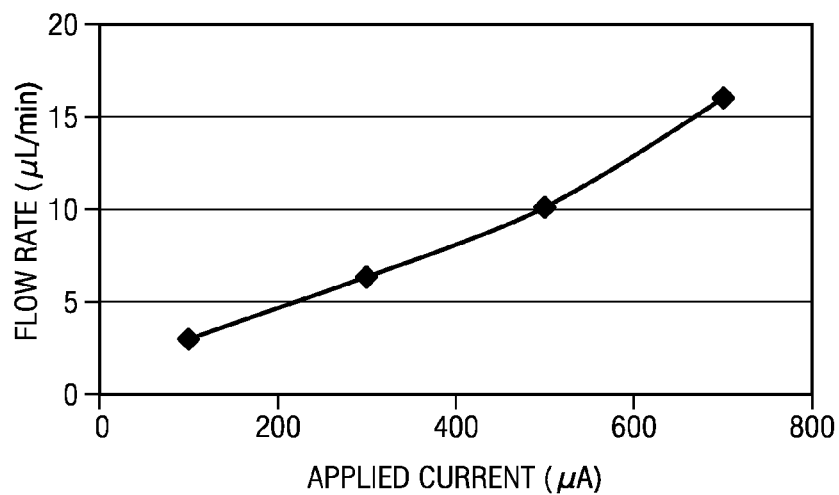
FIG. 14 illustrates variation of flow rate with applied current according to a specific example embodiment of the disclosure.

FIG. 14 is a graph illustrating the relationship between the flow rate and applied current of a pump in certain embodiments. Referring to FIG. 15, in certain embodiments, the flow rate can be controlled by controlling the applied current. When the applied current is increased from about 100 µA to about 300 µA, the flow rate increases from about 3 µL/min to about 6.4 µL/min; when the applied current is then increased to about 500 µA, the flow rate increases to about 10.2 µL/min; and when the applied current is further increased to 700 µA, the flow rate increases to about 16.2 µL/min.

Flow rates of pumps made with similarly made membranes may stabilize eventually at about the same flow rates when a particular current is applied, however the initial flow rates, particularly in the first minute, may differ, according to some embodiments. The initial minute and subsequent flow rates can be made, however, about the same by exposing the membrane and/or electrodes of the electro-osmotic pump in about 50 mM ascorbic acid overnight.

Example 2

Porous Phosphosilicic Acid Membrane Construction

To make a membrane comprising porous phosphosilicic acid for use in an exemplary embodiment, monodisperse fused microspheres of about 1 µm diameter (e.g., Polysciences, Warrington, Pa., Cat. #24326-15) may be coated by adding about 5 µL of about 85 wt. % $H_3PO_4$ to about 5.0 mL of a suspension of microspheres (about 10 weight %), and evaporating the water at about 65° C. Next, about 65 mg of the resulting dried powder may be placed in an about 8 mm ID stainless steel die, which may be pressed to form a pellet. Next, the pellet may be fired for about 4 h at a temperature from about 700° C. to about 900° C. (e.g., at 700° C.). This process may be effective to produce about 8 mm OD phosphosilicic acid coated silica membranes that are about 1.3 mm thick, comprising of randomly packed microspheres. The void volume, determined by weighing the dry and wet membrane, may be about 47%. According to an alternative embodiment, a membrane may be similarly made with less expensive about 1-5 µm diameter poly-disperse microspheres (Sigma-Aldrich, St. Louis, Mo., S5631). Packing of the fused spheres may be random as seen in the scanning electron micrograph of FIG. 15.

Example 3

Silver/Silver Oxide Electrode Construction

In accordance with certain exemplary embodiments, the $Ag/Ag_2O$ anode and cathode may be made of a sheet of carbon paper (e.g., about 3.8 cm×about 1.6 cm (about 6.5 $cm^2$), about 280 µm thick, about 78% porosity (e.g., Toray, TGP-H-090, Spectracorp, Spectracarb 2050-A)). The sheet may be (i) soaked for about 5 min in a solution containing about 1 part per volume colloidal tin oxide NYACOL® SN15 (Nyacol Nano-Technologies Inc., Ashland, Mass.) and about 6 parts per volume de-ionized water to which a solution containing 1% by volume Triton X-100 (Sigma-Aldrich, St. Louis, Mo., X100) is added, (ii) dried at ambient temperature (e.g., between about 18° C. and about 28° C.), and calcined at about 320° C. for about 20 min, resulting in a hydrophilic carbon paper.

Figure 16A:
FIG. 16A is a scanning electron micrograph that illustrates a top-down view of a silver-silver oxide coated-carbon paper electrode according to a specific example embodiment of the disclosure.
Figure 16B:
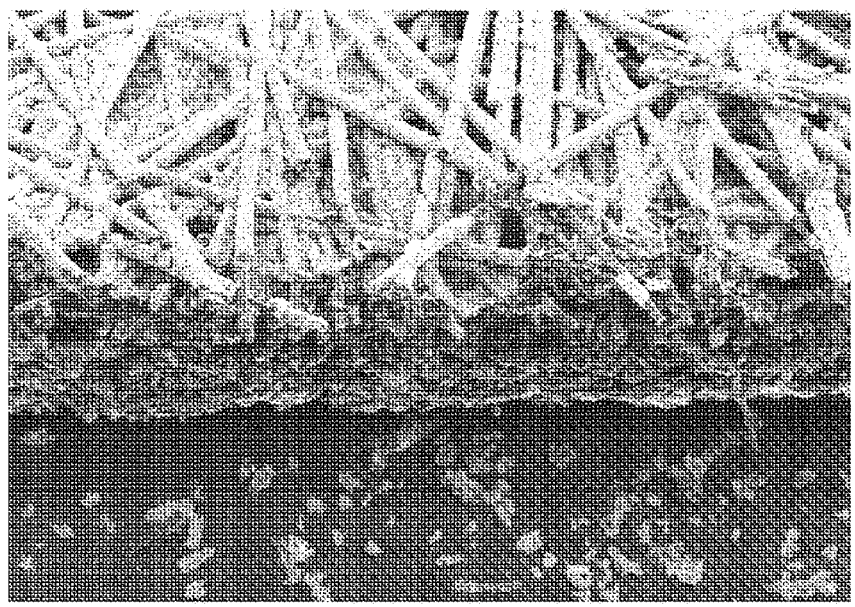
FIG. 16B is a scanning electron micrograph that illustrates a cross-sectional view of a silver-silver oxide coated-carbon paper electrode according to a specific example embodiment of the disclosure.

Next, silver may be plated on the hydrophilic sheet from a stirred solution of about 0.2 M $AgNO_3$, about 0.1 M $HNO_3$ and about 0.015 M citric acid at a constant current of about 5 mA for about 400 min, with about 120° C. (about 18.6 $C/cm^2$) passed. The $Ag_2O$ may then be formed by anodizing about half of the silver in about 1.0 M NaOH at about 5 mA for about 200 min. The scanning electron micrographs of FIG. 16A-B show the resulting $Ag/Ag_2O$ coated fibers of the carbon paper ((a) top-down view; (b) cross-sectional view).

Next, porous electrodes of about 8 mm diameter may be punched from the sheet. The $Ag_2O$ electrodes made according to the above exemplary embodiment may suffice for about 1 day continuous operation at about 20 µA, about 5 hours continuous operation at about 100 µA, and about 1 hour continuous operation at about 500 µA.

Example 4

Working Prototype #1 with Silver/Silver Oxide Electrode—Operation

In accordance with the exemplary embodiment system of FIG. 6C, the potential difference between the non-gassing $Ag/Ag_2O$ anode and the also non-gassing $Ag/Ag_2O$ cathode was measured to be about 0.5 V at a flow rate of about 50 µL $min^{-1} cm^{-2}$, well below the 3-400V operating voltage of other electro-osmotic pumps sustaining such a flow rate. In some embodiments, "per $cm^2$" or simply "/$cm^2$" or "$cm^{-2}$" mean per square centimeter of the water-contacting cross sectional area of the electroosmotic pump. At this voltage and rate, about 4.2 mL of water may be pumped per joule, the energy efficiency also exceeding that of other pumps, such as those of NFT (Nano Fusion Technologies, Tokyo, Japan) having uncoated silica membranes and gas-evolving Pt-electrodes instead of the non-gassing Ag/Ag$_2$O electrodes disclosed herein.

Figure 17A:
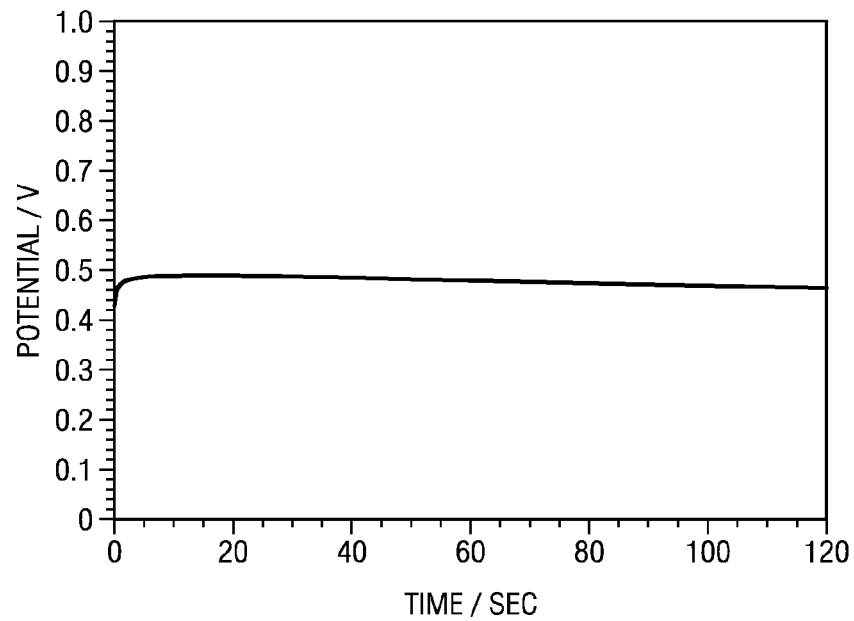
FIG. 17A illustrates time variation of voltage over time according to a specific example embodiment of the disclosure.

FIG. 17A depicts the time dependence of the voltage for the 0.8 cm OD Ag/Ag$_2$O//phosphosilicic acid on fused silica membrane// Ag/Ag$_2$O about 0.3 cm$^2$ active cross-sectional area pump operating at about 0.1 mA constant current at about 24° C., according to an exemplary embodiment.

As depicted in FIG. 17A for the about 0.8 cm OD Ag/Ag$_2$O//phosphosilicic acid on fused silica membrane// Ag/Ag$_2$O about 0.3 cm$^2$ active cross-sectional area pump, the voltage required to operate the about 0.3 cm$^{-2}$ active cross-sectional area pump at about 0.1 mA constant current at about 24° C. was about 0.5±0.1 V. The flow rate at these levels was about 14.5±1.5 µL min$^{-1}$. When the same voltage was applied across the same electrodes in an otherwise identical cell without the membrane, the flow, if any, was too small to be measurable.

Figure 17B:
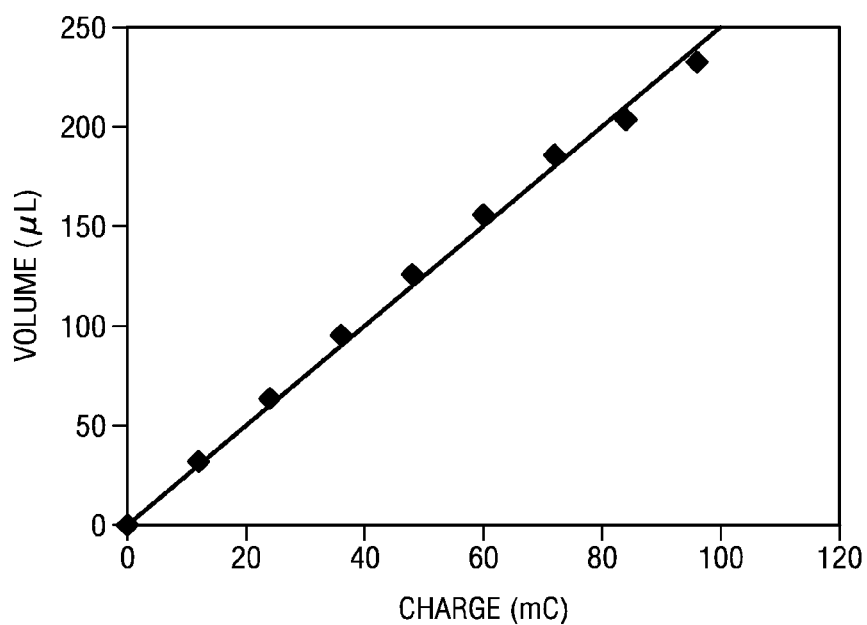
FIG. 17B illustrates variation of delivered volume with charge according to a specific example embodiment of the disclosure.

FIG. 17B depicts for the about 0.8 cm OD Ag/Ag$_2$O// phosphosilicic acid on fused silica membrane// Ag/Ag$_2$O about 0.3 cm$^2$ active cross-sectional area pump, the dependence of the delivered volume on the charge, according to an embodiment applying about 0.1 mA constant current at about 24° C., with a 0.3 cm$^2$ cross-sectional area pump.

According to some embodiments, the volume of the pumped water may increase linearly with the passed charge as depicted in FIG. 17B for the exemplary case of the about 0.8 cm OD Ag/Ag$_2$O//phosphosilicic acid on fused silica membrane// Ag/Ag$_2$O, about 0.3 cm$^2$ active cross-sectional area, pump. At constant current the delivered volume may increase linearly with the elapsed time.

Figure 17C:
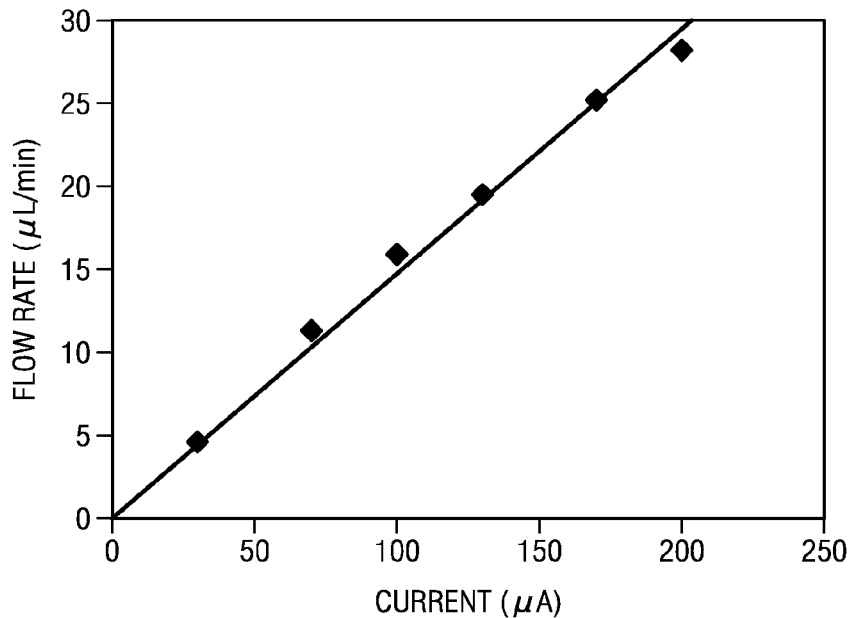
FIG. 17C illustrates variation of flow rate with current according to a specific example embodiment of the disclosure.

FIG. 17C depicts for the exemplary case of the about 0.8 cm OD Ag/Ag$_2$O//phosphosilicic acid on fused silica membrane// Ag/Ag$_2$O, about 0.3 cm$^2$ active cross-sectional area, pump the dependence of the flow rate on the applied current, at about 24° C., measured about 5 minutes after starting the pump.

Figure 17D:
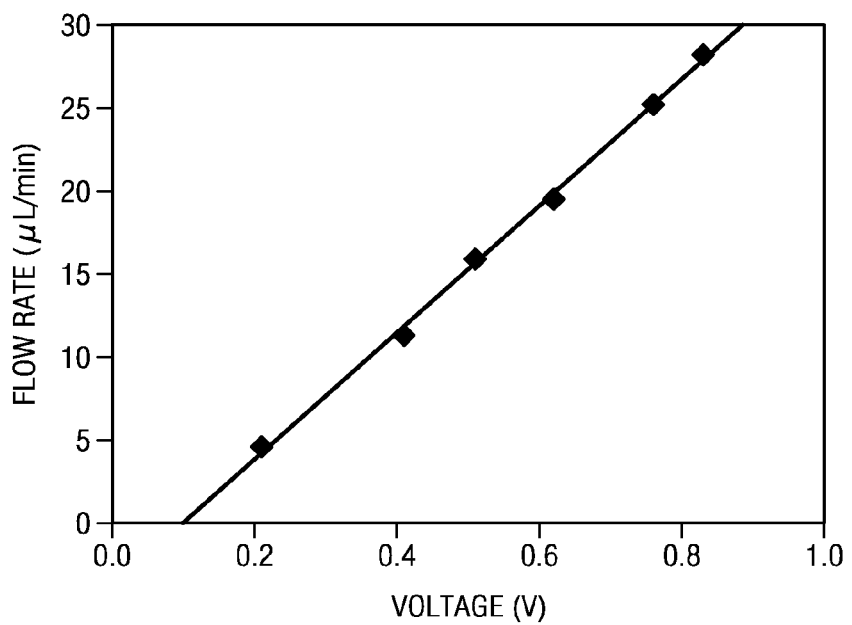
FIG. 17D illustrates variation of flow rate with voltage according to a specific example embodiment of the disclosure.

FIG. 17D depicts for the exemplary case of the about 0.8 cm OD Ag/Ag$_2$O//phosphosilicic acid on fused silica membrane// Ag/Ag$_2$O, about 0.3 cm$^2$ active cross-sectional area, pump the dependence of the flow rate on the operating voltage at about 24° C., measured about 5 minutes after starting the pump.

Figure 17E:
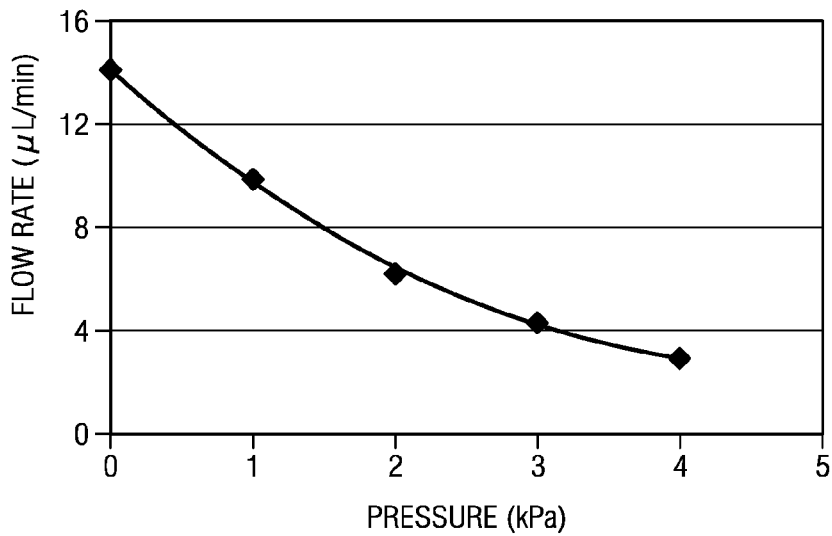
FIG. 17E illustrates variation of flow rate with pressure according to a specific example embodiment of the disclosure.
Figure 19A:
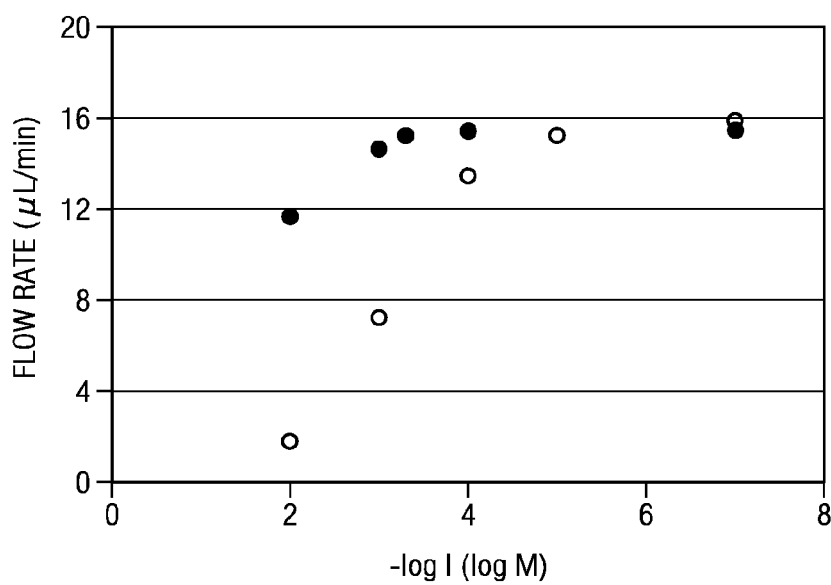
FIG. 19A illustrates variation of flow rate with ionic strength at about 0.1 mA constant current (empty dots) and about 0.6 V constant voltage (filled dots) according to a specific example embodiment of the disclosure.

As depicted in FIG. 17C, the flow rate varied about linearly with the applied current in the range of 0-200 µA. The current deviated from linearity at currents higher than about 200 µA. The slope was about 150 mL min$^{-1}$ A$^{-1}$, the line relating the flow to the current passing through the origin. Extrapolation of the line to zero flow rate showed a voltage threshold of about 0.1 V (FIG. 17D). The dependence of the current on the voltage is linear and the calculated resistance is about 3.6 kΩ, close to the actually measured AC impedance of 3.4 kΩ. The resistance varied from pump to pump, but it did not vary with the applied current or the flow-rate in the same pump. Significantly, the dependence of the flow rate on the voltage is also linear through the voltage range between about 0.2 V and about 1 V. Therefore, its measurement should tell the flow rate for a particular electroosmotic pump. Adding of salts that did react with the electrode components, such as KNO$_3$, decreased both the resistance (3.5 kΩ at 0.01 mM, 3.2 kΩ at 0.1 mM, 2.0 kΩ at 1 mM and 0.6 kΩ at 10 mM) and the flow rate at constant current. In 1 mM KNO$_3$, the operating voltage reduced to 0.35 V from 0.50 V at 0.1 mA (0.33 mA cm$^{-2}$) constant current and about halved the flow rate. FIG. 19A shows the dependence of the flow rate on the ionic strength at about 0.1 mA constant current (open circles) where the added electrolyte is KNO$_3$ (for the exemplary case of the about 0.8 cm OD Ag/Ag$_2$O//phosphosilicic acid on fused silica membrane// Ag/Ag$_2$O about 0.3 cm$^2$ active cross-sectional area pump at about 24° C.):

FIG. 17E shows the dependence of the flow rate on the on the pressure at 0.1 mA constant current (for the exemplary case of the about 0.8 cm OD Ag/Ag$_2$O//phosphosilicic acid on fused silica membrane// Ag/Ag$_2$O, about 0.3 cm$^2$ active cross-sectional area, pump at about 24° C.). Here, the operating voltage increased from about 0.45 V to about 0.55 V when the pressure was raised from nil to about 4 kPa. In 24 hour tests during which the pump was on with about 0.1 mA constant current applied and of for about 20 min a particular pump delivered reproducible boluses of about 130±6 µL.

Example 5

Working Prototype 1 with Silver/Silver Oxide Electrode—Observations

The flow rate per W-cm$^2$ for the Ag/Ag$_2$O//phosphosilicic acid on fused silica// Ag$_2$O/Ag electro-osmotic pump is about 290 mL min$^{-1}$, the highest reported to the knowledge of applicants. In the exemplary case of the about 0.8 cm OD Ag/Ag$_2$O//phosphosilicic acid on fused silica membrane// Ag/Ag$_2$O about 0.3 cm$^2$ active cross-sectional area pump at 24° C., the flow rate of about 14.5±1.5 µL min$^{-1}$ (0.24±0.024 s$^{-1}$) at about 0.1 mA (1.0×10$^{-9}$ Faradays s$^{-1}$) represents passage of about (1.3±0.1)×10$^{-5}$ cools of water. Thus (1.3±0.1)× 10$^4$ water molecules may be driven per transported proton. Because a 0.1 mA current may be maintained at about 0.5 V, about 0.05 mW may transport about 0.24 µL s$^{-1}$. Thus, about 4.8 mL min$^{-1}$ of water may be pumped per watt (about 4.8 mL per joule), over an order of magnitude more than by previously reported electro-osmotic pumps. This is seen, for example, in the comparison of the about 970 mL min$^{-1}$ W$^{-1}$ cm$^{-2}$ efficiency of the exemplary case of the about 0.8 cm OD Ag/Ag$_2$O//phosphosilicic acid on fused silica membrane// Ag/Ag$_2$O about 0.3 cm$^2$ active cross-sectional area pump at 24° C. disclosed herein, with the about 24 mL min$^{-1}$ W$^{-1}$ cm$^{-2}$ efficiency of an NFT pump of about similar dimensions and geometry.

The volume of the pumped water increased linearly with the passed charge in the exemplary case of about 0.8 cm OD Ag/Ag$_2$O//phosphosilicic acid on fused silica membrane// Ag/Ag$_2$O, about 0.3 cm$^2$ active cross-sectional area, pump at about 24° C. (FIG. 17B) showing that it may be coulometrically monitored and implying that, at constant current, it may be monitored by measuring the delivery time. The flow rate may vary linearly with the applied current (FIG. 17C) the slope being about 150 mL min$^{-1}$ A$^{-1}$. In some embodiments, flow may be induced upon application of any current as is evident from the passage of the line relating the flow to the current passes through the origin. The dependence of the flow rate on the operating voltage may also be linear but may have a threshold of about 0.1 V (FIG. 17D). The voltage threshold for flow results from proton-generation at the anode and hydroxide anion generation at the cathode, which may cause a difference in the reversible half cell potentials of the Ag/Ag$_2$O anode and cathode. In the example embodiment 0.3 cm$^2$ cross sectional area pump at about 0.1 mA applied current (0.33 mA cm$^{-2}$ applied current density) operating at about 0.5 V the flow rate of about 14.5±1.5 µL min$^{-1}$ (44 µL min$^{-1}$ cm$^{-2}$) suffices for prandial insulin delivery. The operating voltage is well below the thermodynamic 1.23 V threshold for water electrolysis at 25° C., and no hydrogen or oxygen is evolved.

The electrodes may be non-gassing and may generate and/or consume protons and/or silver cations. For example, the anode may generate highly mobile protons (Reaction 1), combining with the relatively sluggish hydroxide anions that may be generated (Reaction 2) at the cathode:

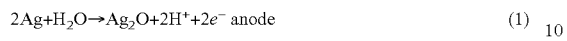

$$2Ag+H_2O \rightarrow Ag_2O+2H^+ +2e^- \text{ anode} \qquad (1)$$

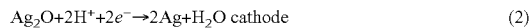

$$Ag_2O+2H^+ +2e^- \rightarrow 2Ag+H_2O \text{ cathode} \qquad (2)$$

Were it not for the small difference between the pH and/or silver cation concentration at the anode and at the cathode the two electrode potentials would have been the same at the threshold for flow (FIG. 17D).

Pumps with proton-generating and/or $O_2$-evolving Pt anodes on which water is electro-oxidized to $O_2$, or anodes that do not generate a proton-flux, like Ag/AgCl, where the Ag is electro-oxidized to AgCl may not be operable. For example, production of bubbles may be undesirable because the bubbles may foul the membrane and reduce flow volume and/or rate. According to some embodiments, a pump system with a Ag/Ag$_2$O anode may generate a proton flux (Reaction 1) and solid Ag$_2$O, not gaseous $O_2$, in the electrooxidation of Ag. Pumps systems with either proton-consuming and gaseous $H_2$-evolving Pt cathodes, on which water is electro-reduced to $H_2$, or cathodes that do not consume protons, like Ag/AgCl where AgCl is electro-reduced to Ag may not be operable. In contrast, at a Ag/AgO cathode, protons may be consumed and/or hydroxide anions may be produced, but solid Ag, not gaseous $H_2$, may be generated (Reaction 2) according to some embodiments.

Fast acting insulin solutions contain typically about 100 units mL$^{-1}$. In the management of Type 1 diabetes, about ¼ of the insulin, i.e., about 0.2 insulin units kg$^{-1}$ day$^{-1}$, is continuously administered, and about 0.2 insulin units kg$^{-1}$ are administered with each of the three daily meals. In the case of a person weighing 80 kg, about 16 units, i.e., about 160 µL of fast acting insulin are delivered with a meal. According to some embodiments, a pump of a cross sectional area of 1 cm$^2$ or less may produce, in the absence of a flow-opposing pressure, a continuous and adjustable flow of about 5 to about 100 µL/min. It could deliver, in some embodiments, a typical meal-associated insulin dose in less than about 30 minutes, less than about 20 minutes, less than about 15 minutes, less than about 10 minutes, less than about 5 minutes, and/or less than about 2 minutes. At a flow-opposing pressure of about 1 kPa, it could deliver a typical meal-associated insulin dose in less than about 30 minutes, less than about 20 minutes, less than about 15 minutes, less than about 5 minutes, and/or less than about 3 minutes when operating at about 0.3 mA cm$^{-2}$ current density at a voltage less than about 1 V, for example about 0.8 V, for example about 0.6 V, for example about 0.5 V. FIG. 17E.

In some embodiments, the delivery of a drug at the slow flow rate appropriate, for example, for the delivery of basal insulin, may be achieved with a pump that can also rapidly deliver large drug boluses, at the high flow rate appropriate for the delivery of prandial insulin doses. In this example, 10 sec long pulses of 0.075 mA were applied to the about 0.8 cm OD Ag/Ag$_2$O//phosphosilicic acid on fused silica membrane// Ag/Ag$_2$O, about 0.3 cm$^2$ active cross-sectional area pump, operating at about 24° C. When these small current pulses were applied, the potential difference between the anode and the cathode increased transiently from about nil to about 0.45 V, The current pulses were applied for 4 times per hour, or about every 15 min, for about 15 h. The flow rate was about 10 µL/min during the current pulse and the resulting delivery rate was about 6.7 µL/h, which is about 160 µL/day (i.e., 10 µL/min×1 minute/60 seconds×10 seconds/pulse×4 pulses/hour×24 hours/day).

Example 6

Working Prototype #2 with Silver/Silver Oxide Coated Electrodes

A programmable, skin-attached, 36×30×8 mm system for subcutaneous infusion of 1.2 mL of a drug solution is described. The system is intended to be replaced daily. It comprises a 20×14×8 mm electronic controller and power source, a 8 mm diameter 2 mm thick electroosmotic pump, a two compartment reservoir for a pumped water and a drug solution, an adhesive tape for attachment to the skin, and a 6 mm long 27 gauge needle. Its removable electronic controller programs the dose rate and dose and is re-used. The electroosmotic pump consists of a porous ceramic membrane sandwiched between a pair of Ag/Ag$_2$O plated carbon paper electrodes. It operates below 1.23 V, the thermodynamic threshold for water electrolysis without gassing. The flow rate can be adjusted between 4 µL min$^{-1}$ and 30 µL min$^{-1}$ by setting either by the voltage (0.2-0.8 V) or the current (30-200 µA). For average flow rates below 4 µL min$^{-1}$ the pump is turned on and off intermittently. For example, a flow rate of 160 µL day$^{-1}$ i.e. 0.13 µL min$^{-1}$ for basal insulin infusion in Type 1 diabetes management is obtained when 10 s pulses of 75 µA are applied every 15 min. High flow rates, of 10-30 µL min$^{-1}$, required for prandial insulin administration, are obtained when the pump operates at 50-200 µA. To prevent fouling by the drug, only pure water passes the pump; the water pushes a drop of oil, which, in turn, pushes the drug solution.

Ambulatory continuous or semi-continuous parenteral administration requiring skin-traversing drugs are now delivered by inexpensive skin-adhered patches, such as 24 h transdermal nitroglycerin, clonidine hydrochloride, rivastigmine, rotigotine and nicotine replacement patches. When drugs do not traverse the skin and when programmable delivery is of essence, they are infused, as is the case in the management of Type 1 diabetes, where fast-acting insulin is infused subcutaneously. Unlike the skin patches which deliver a particular dose over a defined time period, the most widely used remotely controlled programmable insulin infusion systems deliver both a semi-continuous basal flux and meal-associated boli. In the US they be priced between 500 and 5000 USD and require twice or three times weekly replaced components costing between 15 USD and 35 USD.

A system was designed for subcutaneous infusion of ~1 mL of a contained drug solution in 24 h then discarded, except for re-use of its electronic controller. FIG. 6B-C shows photographs of a skin-adhered 36×30×8 mm system designed to subcutaneously infuse 1.2 mL of a drug solution. Its electroosmotic pump is 8 mm OD and 3 mm thick (Shin et al. 2011). In addition to the drug solution (1.2 mL, dyed red) the system contains pure water (1.1 mL, transparent) for pumping the drug, a non-allergenic adhesive patch for attachment to the skin, a needle (6 mm long, 27 gauge) and a re-usable electronic module (20×14×8 mm). To assure that the drug will not affect the flow performance, the only fluid passing the electro-osmotic pump (the white and grey disc at the top-center of FIG. 5b) is pure water. The water displaces an oil-drop, which pushes the drug-solution into the needle.

The re-usable electronic module allows continuous or semi-continuous delivery i.e. the delivery of frequent small doses, programmed delivery of larger doses at particular times, or both. It comprises a home-built CPU-comprising constant current/voltage supply, an LCD display, and a 3 V Li coin cell. The flow, i.e. dose-rate, is set by either the applied current or by the applied voltage, and the delivered dose is set by setting the starting time and the ending time of each constant current or constant voltage pulse and by counting the pulses.

The membrane (1.3 mm thick and 8 mm diameter) was made by pelletizing and firing phosphosilic acid coated 1 μm diameter monodisperse silica microspheres at 700° C. for 4 h. A similar membrane can be formed of polydisperse silica microparticles with 80% of the particles in the 1 to 5 μm range (Aldrich S5631). The anode and the cathode are identical, both made by electroplating silver on 280 μm thick 78% porosity carbon paper, then anodizing ½ of the silver to provide both the Ag and $Ag_2O$ coulombic capacities of 2.6 C.

The 8 mm OD pump was assembled by sandwiching the membrane between the flow-through $Ag/Ag_2O$-coated carbon paper electrodes as shown in FIG. 5A. Although the diameter of the membrane and the electrodes is 8 mm, the diameter of the active, water-contacting area is 6 mm because a PVC ring covers the 1 mm rim. Thus the area of the actual water pumping assembly is 0.3 $cm^2$. The assembled components, from left-to-right are a 1 mm thick, 8 mm OD, 6 mm ID PVC ring connecting the pump and the reservoir; a gold foil lip for the electrical connection; a 280 μm thick, 8 mm diameter $Ag/A_2O$-coated carbon paper anode; a 1.3 mm thick and 8 mm diameter ceramic membrane of fused phosphosilicic acid coated silica microspheres; a 280 μm thick and 8 mm diameter $Ag/A_2O$-coated carbon paper cathode; a gold foil lip for the electrical connection; and a 1 mm thick, 8 mm OD, 6 mm ID PVC ring connecting the pump and the reservoir. The pump is assembled, inserted into the 4 mm gap of the reservoir and sealed with an epoxy resin. In some embodiments, foil lips may be silver instead of gold for a potential cost savings.

A related 8 mm OD pump of the version shown in FIG. 5A was similarly assembled by sandwiching the membrane with two flow-through $Ag/Ag_2O$-coated carbon paper electrodes. Its components, shown in FIG. 5A, were the same as those of the pump shown in FIG. 3A.

Like other electroosmotic pumps, that of the disclosed infusion system has no moving parts and is small. It costs, however, much less than other pumps delivering similar flow rates because their porous platinum electrodes are replaced by carbon paper electrodes on which Ag is plated and partially anodized to $Ag_2O$. The pumps are also simpler, because no flow-sensing and controlling feedback loops are required.

The flow determining characteristics of ceramic membrane surfaces and of electrodes are affected by the pumped drugs. For this reason, the pumps necessitate indirect pumping and the infusion systems are built with two-compartment reservoirs, one for the clean pumped water and the other for the drug solution.

The pumps are built of a pair of identical, porous $Ag/Ag_2O$ plated carbon paper electrodes sandwiching a ceramic membrane. Application of a current (or a voltage) across the electrodes of pump drives protons, produced in the anodic reaction $2Ag(s)+H_2O \rightarrow Ag_2O(s)+2H^++2e^-$, to the cathode, where they are consumed by the cathodic reaction $Ag_2O(s)+2H_2O+2e^- \rightarrow 2Ag(s)+2OH^-$. Without being limited to any particular mechanism of action, protons may propagate rapidly at the polyanionic surface of the ceramic membrane dragging the proximal water sheet, which transfer momentum to the water-bulk causing its flow. In some embodiments, (e.g., where electroosmotic flow is driven by a fast proton flux at the surface of a sandwiched porous membrane and/or adsorption of an impurity on the membrane perturbs flux), it may be desirable to use pure protic liquids like water as a pump fluid. The drug solution is pushed by the pumped water. Dilution of the drug solution by the pumped water is avoided by an oil drop and/or air bubble positioned between the water and the drug solution. To prevent the oil drop from reaching the subcutaneous tissue, the volume of the water-reservoir is 0.1 mL less than that of the drug solution. This assures that when the water is exhausted and oil entering the pump stops the flow, there still remains some drug solution.

The reservoirs are adhered to the skin with a non-allergenic double-sided adhesive tape, commonly used for adhering a toupee to the bald scalp. Use of a subcutaneously inserted plastic cannula is avoided to reduce the cost. The short 27 gauge needle is finger-pressed into the abdominal dermal or sub-dermal tissue. Little or no pain is felt during the insertion and during 1 day of wear.

Flow Control

The flow may be controlled by either the applied voltage or by the applied current. Previously reported, as well as presently manufactured, electroosmotic pumps are built with porous platinum electrodes, operating at water-electrolyzing voltages, typically >3.0 V. Because of the $O_2$ and $H_2$ bubbles produced are trapped in the porous electrodes and on the membrane, their liquid-contacted areas are reduced and the flow is irregular. For this reason, pumps are sold with flow-sensors and electronic feedback loops adjusting the applied voltage so as to keep the flow constant (NFT 2010). The need for sensors and feedback loops is obviated by operating the pump below the 1.23 V, the thermodynamic voltage threshold for water electrolysis at 25° C. Operation at a low voltage (0.2-0.8 V) of the present system is enabled by use of $Ag/Ag_2O$ electrodes.

Figure 18A:
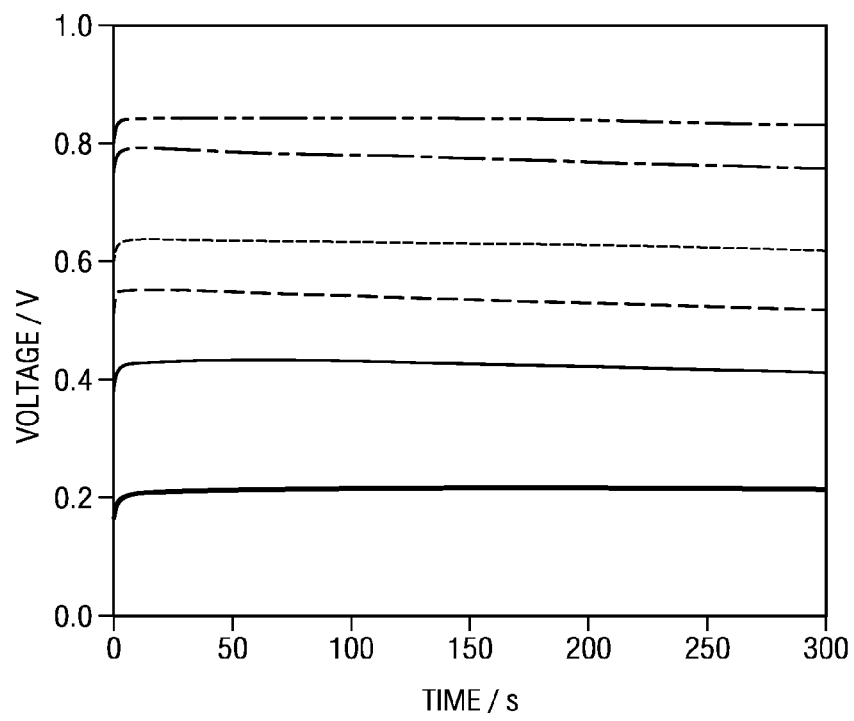
FIG. 18A illustrates variation of flow rate with voltage or current and time delivery of intended drug dose according to a specific example embodiment of the disclosure.

FIG. 18A shows voltages measured across the pump at applied currents of 30 (bottom), 70, 100, 130, 170, and 200 μA (top), resulting in respective flow rates of 5, 11, 15, 19, 25, and 28 μL $min^{-1}$. As shown, when the applied current is raised from 30 μA to 200 μA at 24° C., the voltage across the pump increases linearly from 0.2 V (at 30 μA) to 0.8 V (at 200 μA). The flow rate increases, also linearly, from 5 μL $min^{-1}$ to 28 μL $min^{-1}$. Because the flow scales linearly with either the current or the voltage, it can be controlled by either. When a constant current is applied, the intended dose is set by programming the start and end times. The actually delivered dose can be coulometrically monitored, irrespective of the constancy of the current because the flow rate scales linearly with the current.

Average flow rates of less than 4 μL $min^{-1}$ are conveniently obtained by pulsing the current (or the voltage). For example, in Type 1 diabetes management a typical average flow rate of 0.13 μL $min^{-1}$ (160 μL $day^{-1}$) of fast acting insulin is sought in a person weighing 75 kg to sustain the "basal" insulin level. Such a slow flow rate is conveniently produced by applying every 15 min 10 s long pulses of 75 μA.

Consumption of the anode's Ag or the cathode's $Ag_2O$ allows ~7 hours continuous operation at 100 μA applied current, where the flow rate is 15 μL $min^{-1}$. Thus the maximum infused volume of the drug solution is ~6 mL. It can be delivered semi-continuously over 24 h, or intermittently, in a series of programmed dose-pulses that can be similar or can differ. The capacity of the 38 mAh CR1220 coin cell used in the electronic module suffices for 16 days of operation.

The flow rate scales linearly with the active area of the pump, i.e. increases with the square of its diameter. Thus a 12 mm OD, 10 mm diameter active area pump would deliver 42 µL min$^{-1}$ at 0.5 V and 280 µA applied current versus the 15 µL min$^{-1}$ flow rate of the here-described 8 mm OD, 6 mm diameter pump operating at 0.5 V and 100 µA. Although the reservoir volumes scale with the cube of their linear dimensions, it is preferred for skin adhered systems not to increase the thickness beyond about 12 mm in order to avoid excessive stress that could cause separation of the infusion system from the skin. Exemplary projected dimensions and drug reservoir volumes for systems of 8 mm thickness are 36×30×8 mm, 1.0 mL; 53×47×8 mm, 2.7 mL; 78×72×8 mm, 7.0 mL. At 12 mm thickness, the volume would be 20 mL for a 78×72×12 mm system. However, the simple skin-adhered system is usually not appropriate for the infusion of large volumes and is best for the delivery of small volumes of concentrated drugs solutions.

In the exemplary case of fast-acting insulin, there is a need for basal and prandial deliveries at very different flow rates. Fast acting insulin solutions contain typically about 100 units mL$^{-1}$. In the management of Type 1 diabetes, about ¼ of the insulin, i.e. about 0.2 insulin units kg$^{-1}$ day$^{-1}$, are semi-continuously administered, and about 0.2 insulin units kg$^{-1}$ are administered prandially, i.e. with each of the three daily meals, in about 10 min. In the case of a person weighing 70 kg, about 14 units, i.e., about 140 µL of fast acting insulin, need to be delivered with a meal in about 10 min. The pump delivers this dose in about 9 min. The delivery time can be shortened to 5.5 min simply by increasing to the applied current to 200 µA. For the delivery of basal insulin, 4 current pulses of 75 µA and of 15 sec duration are hourly applied for a flow rate of 10 µL min$^{-1}$ during the current pulse, and for a daily rate of 144 µL day$^{-1}$.

Figure 18B:
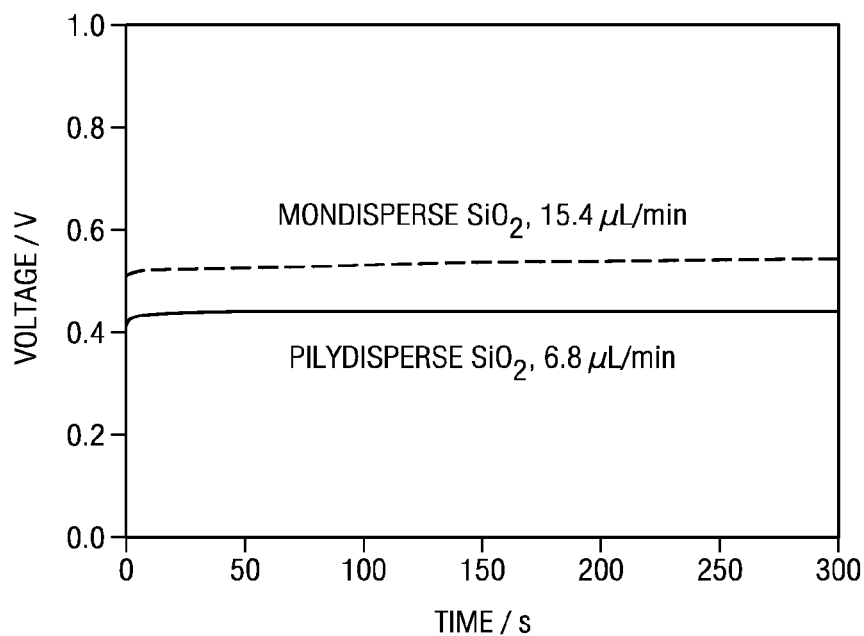
FIG. 18B illustrates the flow rate and operating voltage of pump made with 1 µm monodisperse microspheres and 1-5 µm polydisperse microparticles according to a specific example embodiment of the disclosure.

The disclosed system has no parts costing more than a few cents. The cost of preparing monodisperse microspheres may be reduced by replacing the monodisperse microspheres by polydisperse microspheres, though their use halves the flow rates FIG. 18B. Flow rates and operating voltages of pumps made with 1 µm monodisperse microspheres (dot) and made with 1-5 µm polydisperse microparticles (line) at 100 µA applied current.

The skin-adhered 36×30×8 mm, disposable and programmable subcutaneous infusion system built with an electroosmotic pump having Ag/Ag$_2$O/carbon paper electrodes infuses 1 mL of a drug solution at a rate of 4-30 µL min$^{-1}$ when operating at 0.2-0.8 V and 30-200 µA. A slower flow rate is obtainable by current pulsing. The system's characteristics allow fast-acting insulin delivery in Type 1 diabetes management and could be used for the programmed infusion of small volumes of concentrated solutions of other drugs.

Example 7

Working Prototype #3 with Silver/Silver Oxide Electrode

The Ag/Ag$_2$O-ceramic membrane-Ag/Ag$_2$O electroosmotic pump, intended for use in daily or twice-weekly replaced two-compartment drug infusion systems, is simple, non-gassing and energy efficient. When a current or a voltage is applied across the membrane of the pump protons, produced in the anodic reaction $2Ag(s)+H_2O \rightarrow Ag_2O(s)+2H^+ +2e^-$ are driven to the cathode, where they are consumed by the reaction $Ag_2O(s)+2H_2O+2e^- \rightarrow 2Ag(s)+2OH^-$. Water is driven in the pump by the flux of a layer of protons at the surface of the ceramic membrane, transferring momentum to the proximal sheet of water, which induces the flow of bulk-water. About $10^4$ water molecules flow per reacted electron. In the presence of ions at concentrations in excess of $10^{-5}$ M in the water-bulk, the flow rate at constant applied current, declines. The cause of the decline is shunting of part of the current carried by the membrane-surface protons to ions moving in the water-bulk. In the Ag/Ag$_2$O-ceramic membrane-Ag/Ag$_2$O electroosmotic pump Ag$^+$ ions released from the electrodes increase the ionic conductivity of the water-bulk lowering the current efficiency, i.e. flow rate at constant current. Operation of the pump at constant voltage rather than at constant current improves the stability of the flow. The flow is further stabilized by NAFION®-coating the electrodes, as the NAFION® retains Ag$^+$ ions. The 20 µL min$^{-1}$ flow rate of 6 mm I.D. pumps with NAFION® coated electrodes operating at 1 V is stable for 1 month when the pumps are operated daily for 5 min; or for 70 hours when the pump is pulsed for 30 sec every 30 min, or for 2 hours when operating continuously.

The intended application of the Ag/Ag$_2$O-ceramic membrane-Ag/Ag$_2$O electroosmotic pump in drug-delivery differs from that of its cousins applied in analytical and bioanalytical Lab-on-a-Chip micro-systems. Unlike its cousins, the Ag/Ag$_2$O-ceramic membrane-Ag/Ag$_2$O pump, pumping is a few mL/day, is made of components that are produced for pennies. It is intended to be part of a skin-adhered patch, subcutaneously or intramuscularly delivering drugs that do not pass the skin. The system would allow programmed delivery, e.g. different doses and dose rates at different times. Like its trans-dermal skin patch counterpart, the infusion system and its few mL drug-reservoir would be daily or twice-weekly replaced. The daily or twice weekly replacement of the system permits use of consumed electrode materials, e.g. of Ag electrooxidized to Ag$^+$ at the anode (where the Ag$^+$ is precipitated as Ag$_2$O) and of Ag$_2$O electroreduced to Ag at the cathode.

The medical application of the pump necessitates strict control of the dose-rate, i.e. the flow rate, and of the dose, i.e. the delivered volume. In general, the flow rate in an ideal electro-osmotic pump varies linearly with the current or the voltage and is constant when the current or the voltage is held constant. In less ideally stable infusion system, the flow must be monitored and adjusted by a feed-back. While monitoring and adjustment by a feedback loop are practiced, they add to the cost and are to be avoided in a frequently replaced infusion system. The constancy of the flow in the Ag/Ag$_2$O-ceramic membrane-Ag/Ag$_2$O pump is affected by Ag$^+$ in the pumped water and that the combination of constant voltage operation and NAFION coating of the Ag/Ag$_2$O electrodes stabilizes the pump.

Pumps having and 8 mm OD and a 6 mm ID were made by sandwiching a phosphosilic acid coated silica membrane between two identical flow-through Ag/Ag$_2$O-coated carbon paper electrodes. The membrane was formed by pelletizing at 300 psi then firing phosphosilic acid coated 1 µm monodisperse silica microspheres at 700° C. for 4 h. The membranes were then thoroughly washed with water and stored in a water-filled bottle. The porous electrode was prepared by electroplating Ag on 200 µm thick carbon paper (Spectracarb 2050A-0850), then anodizing ½ of the plated Ag to Ag$_2$O, so as to provide a 1.3 C capacity of Ag and a 1.3 C capacity of Ag$_2$O. For preparing NAFION® coated Ag/Ag$_2$O electrodes, the electrodes were dipped for 10 s in 1% NAFION® solution in isopropanol, made by diluting the available 5% NAFION® solution (Aldrich 274704) and air dried, repeating the dipping and drying steps, then curing at 120° C. for 1 hr. The assembled pumps were kept water-filled until used, usually on the next day.

The flow rate was measured by monitoring the displacement of a calibrated micro-syringe connected to the outlet of the pump. The applied pressure opposing the flow was adjusted by changing the height of water-filled tubing connected to the outlet of the pump, e.g. to 10 cm for 1 kPa. The temperature, measured by a thermocouple located near to the pump, was controlled by a refrigerated circulator (Fisher Scientific 9101). A home-built CPU-controlled voltage/current supply having a data acquisition unit was used to operate the pump and to monitor its current and voltage.

Without being limited to any particular mechanism of action, flow of water in the $Ag/Ag_2O$-ceramic membrane-Ag/$Ag_2O$ electroosmotic pump may be caused by of the rapid flux of protons at the surface of the ceramic membrane in the electric field across the membrane. The protons are produced in the anodic reaction, $2Ag(s)+H_2O \rightarrow Ag_2O(s)+2H^++2e^-$ and are consumed by combining with $OH^-$ anions produced by the cathodic reaction, $Ag_2O(s)+2H_2O+2e^- \rightarrow 2Ag(s)+2OH^-$. The fast flux of protons induces the flow of the water-sheet proximal to the surface of the membrane, which transfers momentum to the water-bulk. About $10^4$ water molecules are transported per electron, i.e. proton. Ions in the water-bulk are detrimental, because they provide an alternative pathway for the flow of current. Their effect becomes noticeable, as seen in FIG. 19A, which shows dependence of the flow rate on the concentration of added $KNO_3$ for a pump with a 1.3 mm thick ceramic membrane operating at 24° C. (hollow dots, at 100 µA constant current; filled dots, at 0.6 V constant voltage), already at $10^{-5}$ M concentration. At a $10^{-3}$ M concentration, the ions halve the flow of the pump operated by applying a constant current. However, when the voltage is held constant, the flow rate remains nearly stable up to $10^{-3}$ M concentration.

Figure 19B:
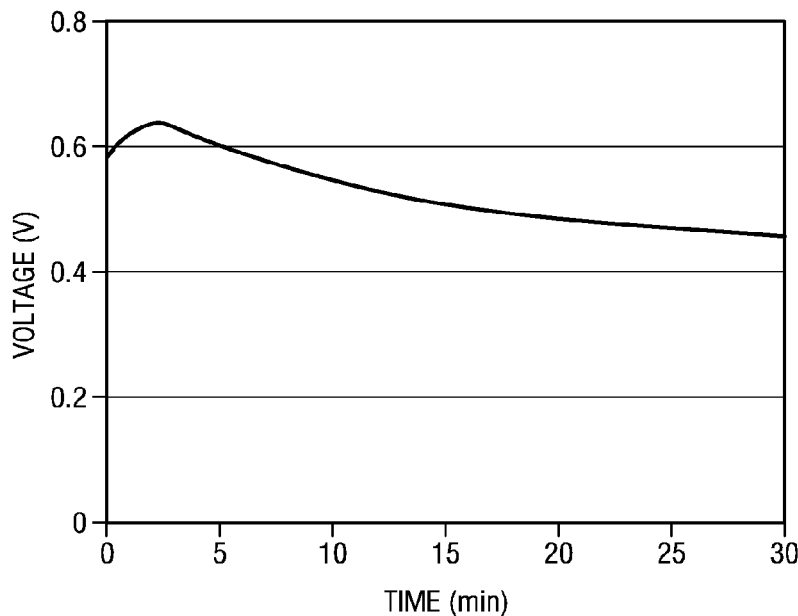
FIG. 19B illustrates variation of voltage with time according to a specific example embodiment of the disclosure.
Figure 19C:
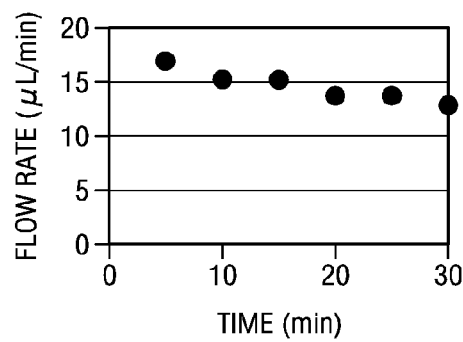
FIG. 19C illustrates variation of flow rate with time according to a specific example embodiment of the disclosure.
Figure 19D:
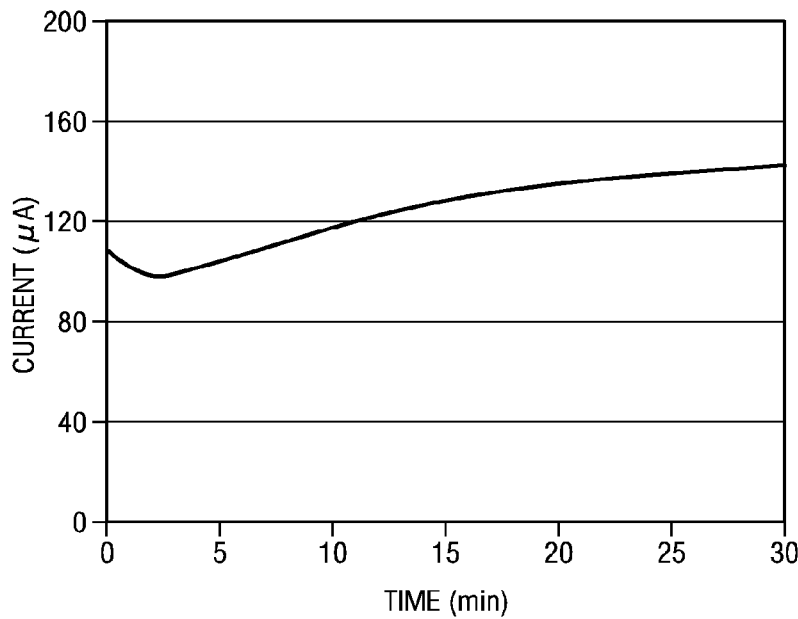
FIG. 19D illustrates variation of current with time according to a specific example embodiment of the disclosure.

Both $Ag/Ag_2O$ electrodes are potential Ag-cation sources. At the anode, most of the Ag+ formed in the electrooxidation $Ag \rightarrow Ag+e$ is precipitated as $Ag_2O$ by reacting with water $2Ag^++H_2O \rightarrow Ag_2O+2H^+$ unless the local pH is acidic. Unless the pH at the cathode is basic, $Ag_2O$ may dissolve to produce $Ag^+$, $Ag_2O+H_2O \rightarrow 2 Ag^++2 OH^-$.[4] The effect of the increase in the concentration of $Ag^+$ in the water bulk during the operation of the pump on the flow rate is similar to the effects of the purposely added $K^+$ and $NO_3^-$ ions in FIG. 19A. When a constant current is applied across the membrane, a flux of $Ag^+$ ions from the anode to the cathode carries part of the applied current, lowering the flow rate and the current efficiency. When the voltage is held constant, a current increase is a tell-tale sign of $Ag^+$ in the water. It implies that at constant applied current the flow rate has decreased. FIG. 19B depicts a time dependence of the voltage at 100 µA applied current. FIG. 19C show the time dependence of the flow rates. FIG. 19D depicts time dependence of the current at 0.6V applied voltage at 1.3 mm-membrane at 24° C.

Figure 21:
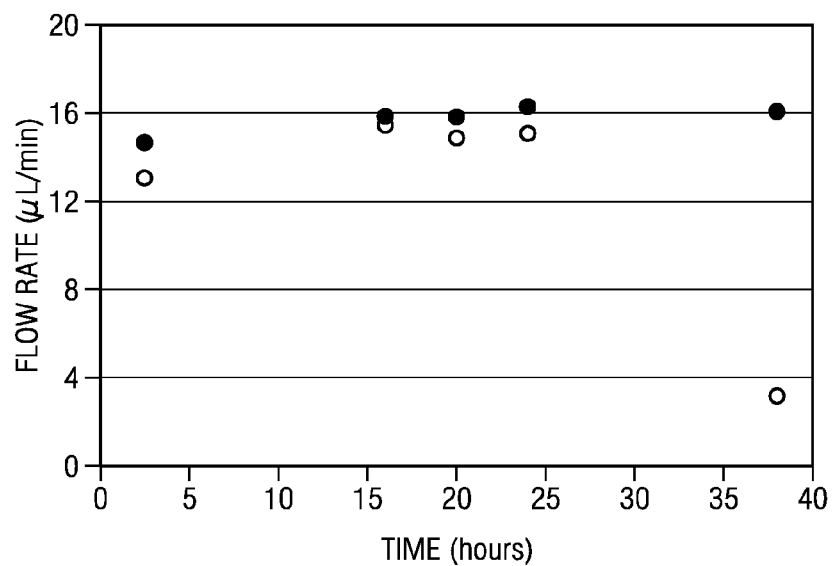
FIG. 21 illustrates variation of flow rate with time according to a specific example embodiment of the disclosure.

Stabilization by NAFION® Coating of the Electrodes. Coating the porous $Ag/Ag_2O$/carbon paper electrodes with NAFION® stabilizes the flow and long-term performance FIG. 21. FIG. 21 depicts stabilization of the flow rate and long-term performance by coating the electrodes with NAFION®. The pumps were pulsed at 0.6 V for 5 minutes 2, 16, 20, 24, and 36 hours after being filled with water. Hollow dots, uncoated, filled dots, NAFION® coated $Ag/Ag_2O$ electrodes. 1.3 mm thick membrane, 24° C.

As expected from studies of the photochromism of $Ag^+$ doped silicate glasses[5,6], the membrane-bound $Ag^+$ is photoreduced in daylight to Ag, readily seen by the naked eye. Both sides of the membranes were examined after finishing the operation. FIG. 22A-D depicts the silver-precipitation in the ceramic membranes from the pumps intermittently operated 5 times for 5 min at 0.6 V during 38 hours as shown in FIG. 21. FIG. 22A depicts the anode-facing side of the membrane with uncoated electrodes. FIG. 22B depicts the cathode-facing side of the membrane with uncoated electrodes. FIG. 22C depicts the anode-facing side of the membrane with NAFION® coated electrodes. FIG. 22D depicts the cathode-facing side of the membrane with NAFION® coated electrodes.

The hindrance of $Ag^+$ release by the NAFION®-coating is also seen when the pumps are operated continuously promptly after their assembly at for 30 minutes at 100 µA applied current. The membrane of the pump with NAFION® coated electrodes shows a lesser deposit of Ag (FIG. 21). There is more Ag on the side of the membrane facing the cathode, implying electroreduction of $Ag^+$ arriving from the anode. FIG. 21 depicts silver-precipitation in ceramic membranes of after applying 0.6 V for 30 min just after their assembly. As seen in FIG. 20A-D, comparing images of a membrane from a pump with NAFION® coated electrodes FIGS. 20A-B with images of membranes of a pump with uncoated electrodes, NAFION®-coating of the electrodes retards the incorporation of $Ag^+$ in the membrane FIGS. 20C-D. FIG. 20A depicts the anode-facing side of the membrane with uncoated electrodes. FIG. 20B depicts the cathode-facing side of the membrane with uncoated electrodes. FIG. 20C depicts the anode-facing side of the membrane with NAFION® coated electrodes. FIG. 20D depicts the cathode-facing side of the membrane with NAFION® coated electrodes.

Figure 23A:
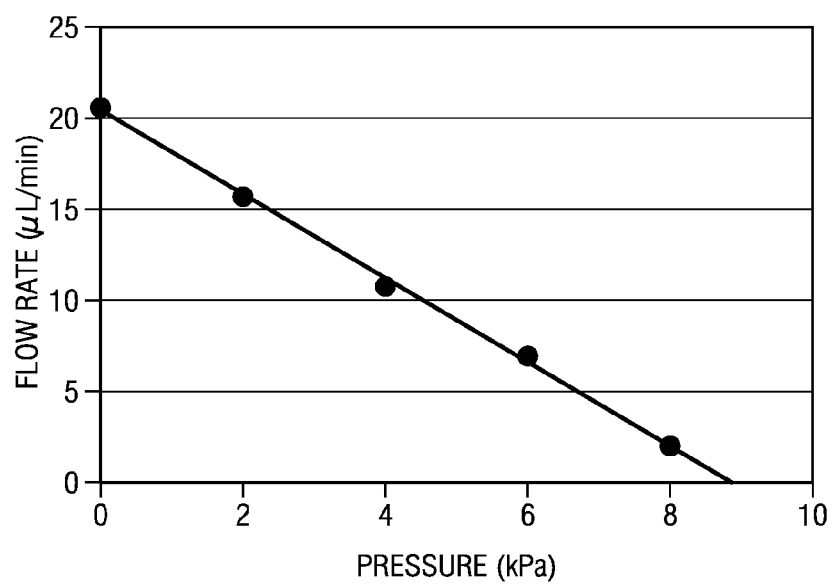
FIG. 23A illustrates variation of flow rate with pressure according to a specific example embodiment of the disclosure.
Figure 23B:
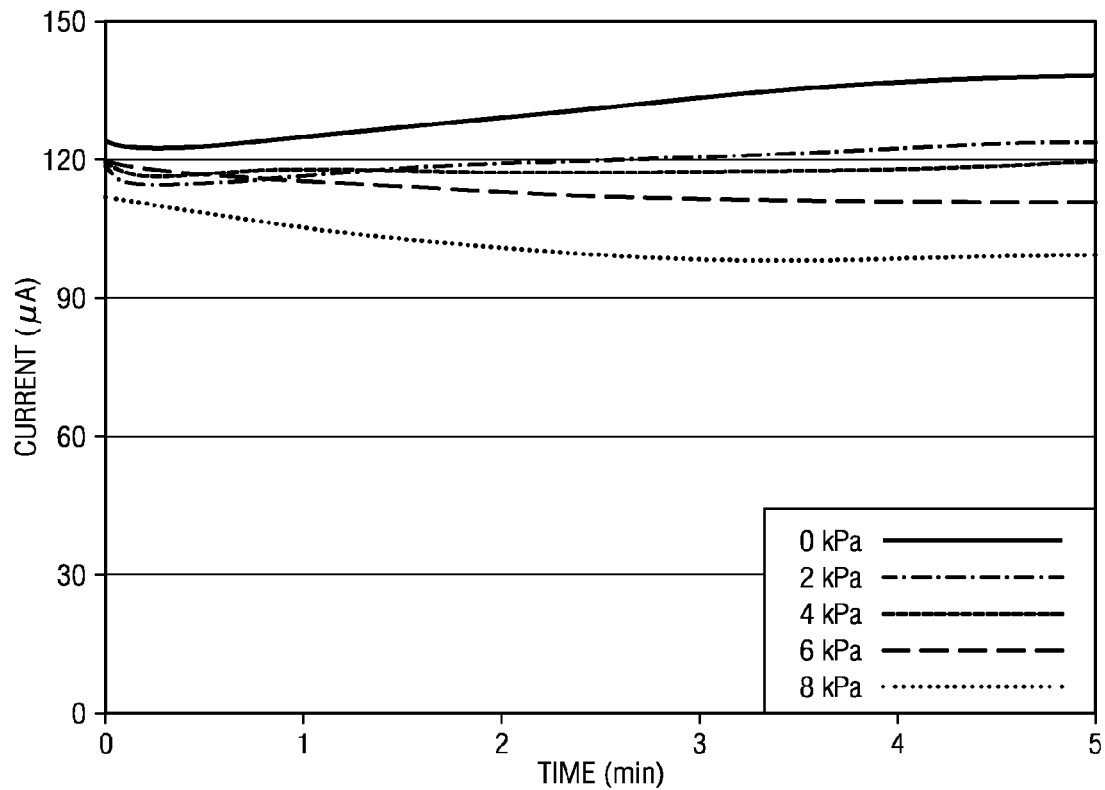
FIG. 23B illustrates variation of current with time according to a specific example embodiment of the disclosure.
Figure 23C:
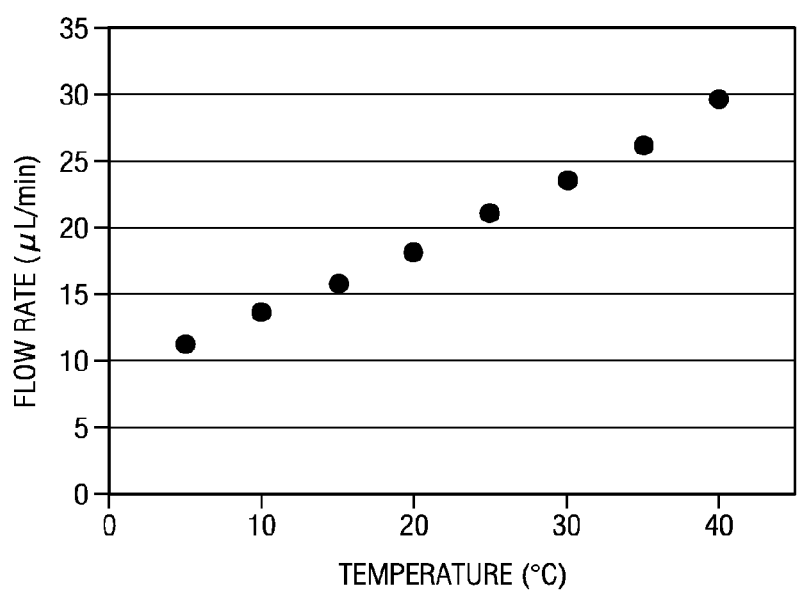
FIG. 23C illustrates variation of flow rate with temperature according to a specific example embodiment of the disclosure.
Figure 23D:
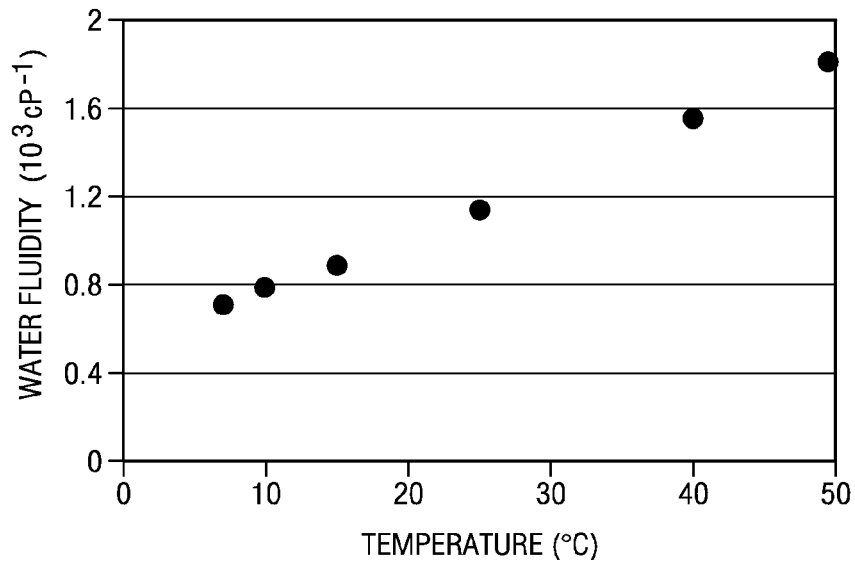
FIG. 23D illustrates variation of water fluidity with temperature according to a specific example embodiment of the disclosure.
Figure 24:
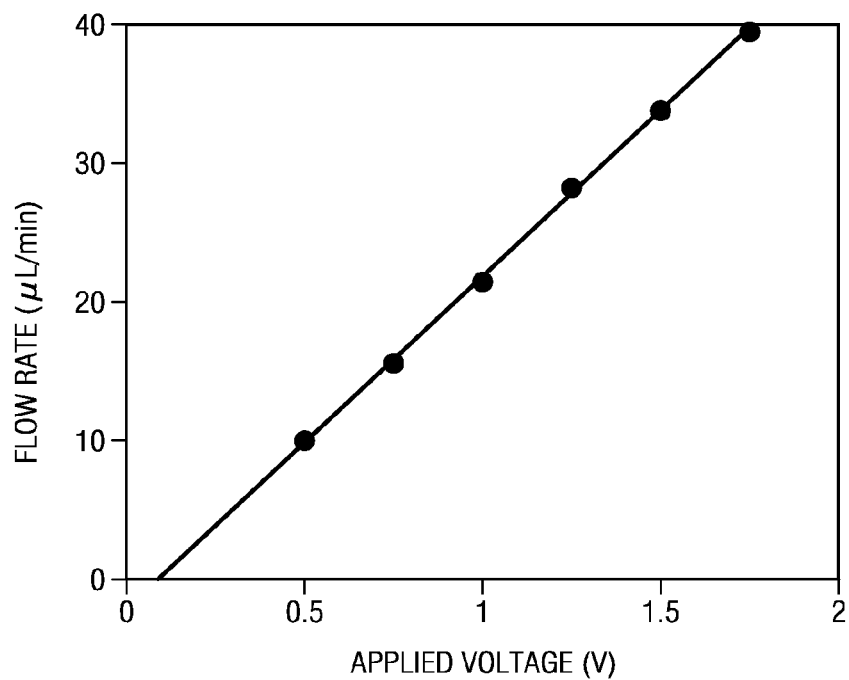
FIG. 24 illustrates variation of flow rate with voltage according to a specific example embodiment of the disclosure.

The variations of the flow rate with the flow-opposing pressure and with the temperature are shown for a pump operating at 1 V, having NAFION coated electrodes and a 2 mm thick membrane, in FIG. 23A-D. FIG. 23 depicts the dependence of the flow rate on the pressure FIG. 23A and temperature FIG. 23C at 1.0 V constant voltage operation. 2.0 mm thick membrane. FIG. 23B shows the currents for pressures of 0, 2, 4, 6, and 8 kPa (top to bottom). FIG. 23C shows the temperature dependence of the fluidity of water. In FIG. 23A the flow rate decreases linearly with the flow-opposing pressure, dropping to nil at 9 kPa. As the pressure increases, the current decreases. Because the drugs can be subcutaneously infused below 1 kPa, the loss in flow rate associated with subcutaneous infusion is expected to be less than 10%. A drop in current if the flow is blocked would warn the user of the malfunction. As seen in FIG. 23D, the temperature dependence of the flow rate tracks that of the fluidity of water.

Figure 25A:
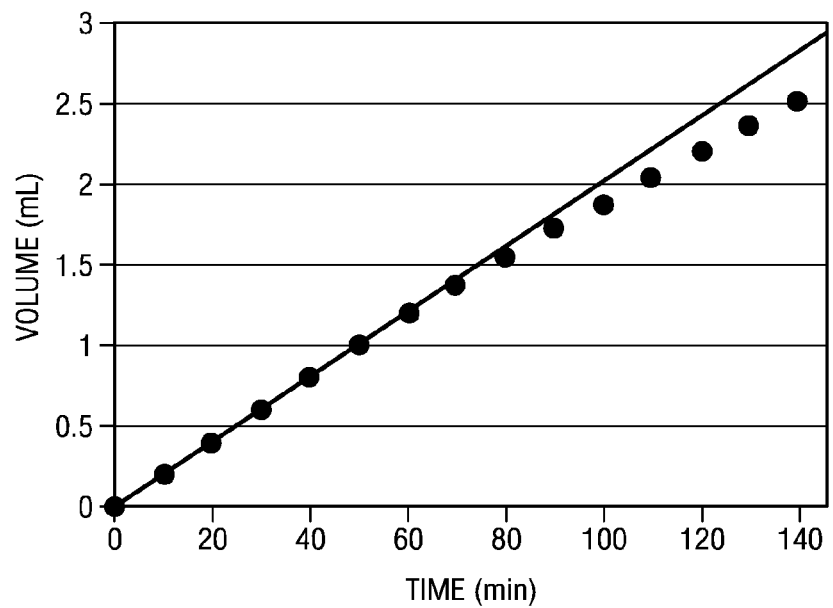
FIG. 25A illustrates variation of volume with time according to a specific example embodiment of the disclosure.
Figure 25B:
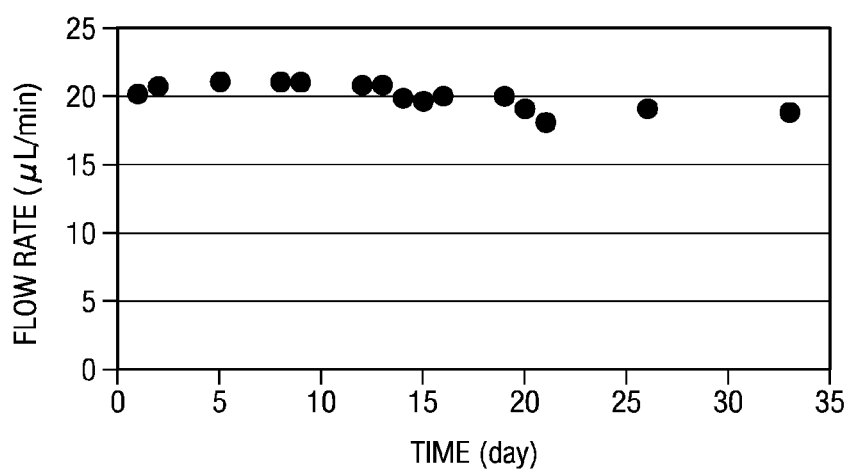
FIG. 25B illustrates variation of flow rate with time according to a specific example embodiment of the disclosure.

Operation at constant applied voltage rather than at constant applied current in combination with NAFION®-coating of the electrodes substantially extends the utility of the pump in its intended application in a skin-attached miniature drug pump, where constancy of flow rate is of essence. FIG. 25A depicts the dependence of the delivered volume on the elapsed time in continuous operation at 1.0 V constant voltage. The flow rate was measured at 10 min intervals. FIG. 25A shows, for a pump with a 2.0 mm thick membrane operating at 24° C., the constancy of the flow in a 140 min test of the continuously operating pump. During the first 80 min, in which 1.5 mL are delivered, the flow is constant. This volume exceeds more than twice the typically 0.7 mL daily volume of fast acting insulin used in the management of Type 1 diabetes. FIG. 25 B shows stable flow when the pump operates for about a month intermittently 15 times for 5 min. FIG. 25 B depicts month-long pulsed operation with 1 V applied daily for 5 min.

Figure 26:
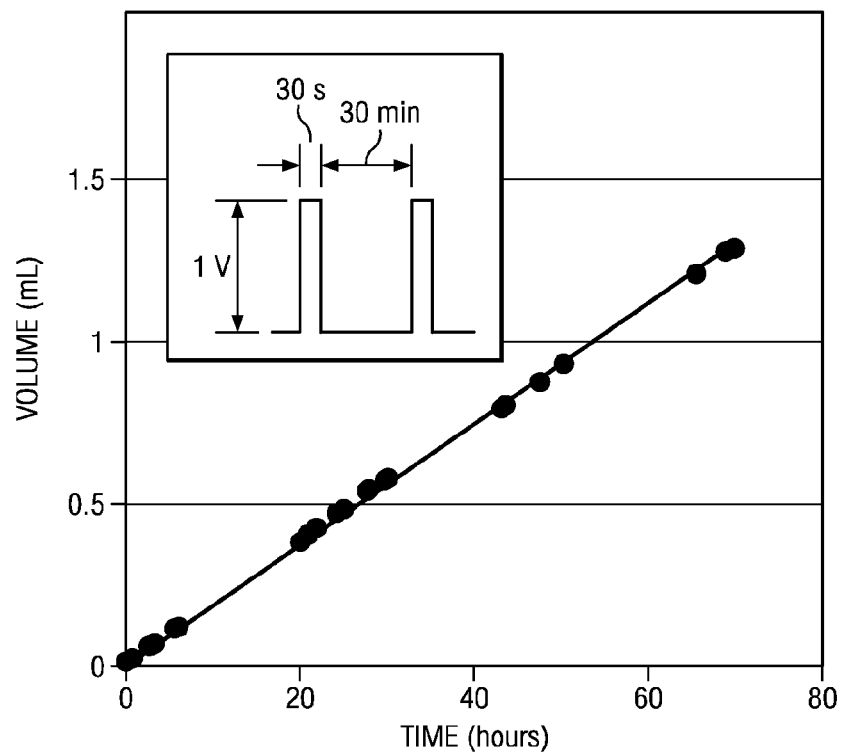
FIG. 26 illustrates variation of volume with time according to a specific example embodiment of the disclosure.
Figure 27:
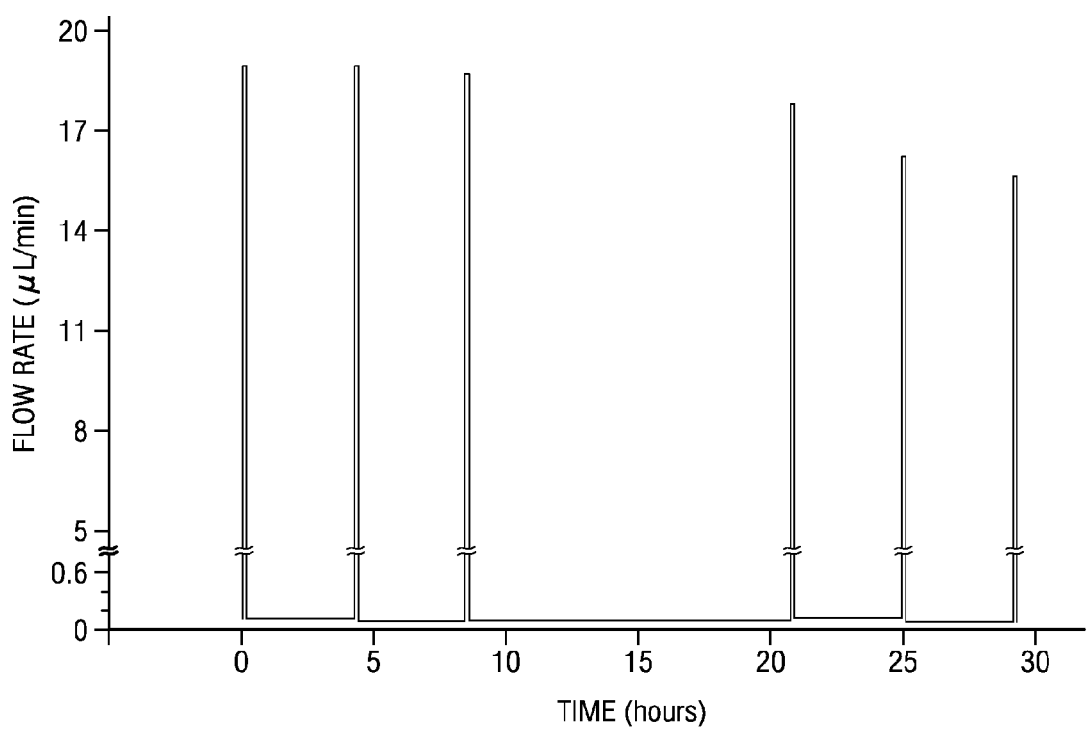
FIG. 27 illustrates variation of flow rate with time according to a specific example embodiment of the disclosure.

The constancy of the flow in pulsed operation, relevant to the delivery of sufficiently frequent, small drug doses for maintaining of a semi-constant level of the drug, the flow is stable for 70 hours when the pump is pulsed for 30 sec hourly twice. (FIG. 26). FIG. 26 depicts the dependence of the delivered volume on the elapsed time in pulsed operation at 1.0 V constant voltage for 30 sec every 30 min. Flow rate measured 3 times/day. 2.0 mm thick membrane, 24° C. In the combination of delivery of both maintenance doses and boli, as is required in the in the management of Type 1 diabetes where meal-associated doses of insulin are infused and a lesser steady level is maintained, the flow in both periods is about constant for 24 h. (FIG. 27). FIG. 27 depicts, for a pump having a 2.0 mm thick membrane operating at 24° C., mixed pumping of occasional large boli (a three 8 min long 1 V pulse was applied every 4 hours) and frequent small boli (5 s long pulses of 0.3 V are applied every 5 min).

The stability of the flow rate in the $Ag/Ag_2O$-ceramic membrane-$Ag/Ag_2O$ electroosmotic pump is improved by operating the pump at a constant voltage (rather than at a constant current) and by NAFION®-coating of electrodes. A steady flow rate of 20 $\mu L\ min^{-1}$ is maintained for 2 hours when the pump operates continuously or when it operates intermittently 15 times for 5 min over a one month period or when it is pulsed for 30 sec every 30 min for 70 hours.

What is claimed is:

1. A direct current electro-osmotic pump comprising:
   a porous, platinum-free, carbon-based cathode;
   a porous, platinum-free carbon anode; and
   a porous ceramic membrane between the cathode and the anode having a first surface and a second surface opposite the first surface,
   wherein the porous ceramic membrane comprises vitreous ceramic spheres from about 0.1 µm to about 10 µm in diameter selected from the group consisting of uncoated silica spheres, spheres comprising oxides of silicon and phosphorus, spheres comprising oxides of silicon and boron, and combinations thereof,
   wherein at least a part of the first surface of the membrane is in physical contact with the anode,
   and at least a part of the second surface is in physical contact with the cathode, and
   wherein the pump is configured to operate at a potential difference (V) between the anode and the cathode of V≤3 volts without producing bubbles visible to a naked eye.

2. A direct current electro-osmotic pump according to claim 1, wherein
   the potential difference (V) between the anode and the cathode is 0.1 volts<V≤3 volts at about 25° C.; and
   the electro-osmotic pump is configured to operate with a flow rate per $cm^2$ of liquid-contacted area of at least 10 $\mu L\ min^{-1}\ cm^{-2}$.

3. A direct current electro-osmotic pump according to claim 2, wherein the potential difference (V) between the anode and the cathode is 0.1 volts<V≤2 volts at about 25° C.

4. A direct current electro-osmotic pump according to claim 2, wherein the electro-osmotic pump is configured to coulometrically monitor a volume of a pumped solution.

5. A direct current electro-osmotic pump according to claim 1, wherein the porous ceramic membrane is from about 0.1 mm to about 3 mm thick and/or from about 1 mm to about 30 mm wide.

6. A direct current electro-osmotic pump according to claim 1, wherein the anode further comprises an electrically conducting polymer, the cathode further comprises the electrically conducting polymer, or both the anode and cathode further comprise the electrically conducting polymer.

7. A direct current electro-osmotic pump according to claim 6, wherein the electrically conducting polymer is selected from polyaniline and substituted polyaniline.

8. A direct current electro-osmotic pump according to claim 1, wherein the porous anode further comprises an anodic reactant and a cathodic reactant, the porous cathode further comprises the anodic reactant and the cathodic reactant, or both the porous anode and the porous cathode further comprises the anodic reactant and the cathodic reactant.

9. A direct current electro-osmotic pump according to claim 1, wherein the porous ceramic membrane has an outside diameter of 8 mm.

* * * * *